United States Patent [19]
Foulkes et al.

[11] Patent Number: 5,846,720
[45] Date of Patent: *Dec. 8, 1998

[54] METHODS OF DETERMINING CHEMICALS THAT MODULATE EXPRESSION OF GENES ASSOCIATED WITH CARDIOVASCULAR DISEASE

[75] Inventors: J. Gordon Foulkes, Huntington Station, N.Y.; Franz E. Liechtfried; Christian Pieler, both of Vienna, Austria; John R. Stephenson, Santa Cruz, Calif.; Casey C. Case, Lynbrook, N.Y.

[73] Assignee: Oncogene Science, Inc., Uniondale, N.Y.

[ * ] Notice: The term of this patent shall not extend beyond the expiration date of Pat. No. 5,580,722 and 5,589,722.

[21] Appl. No.: 700,757

[22] Filed: Aug. 15, 1996

Related U.S. Application Data

[63] Continuation of Ser. No. 832,905, Feb. 7, 1992, Pat. No. 5,580,722, which is a continuation-in-part of Ser. No. 555,196, Jul. 18, 1990, abandoned, which is a continuation-in-part of Ser. No. 382,712, Jul. 18, 1989, abandoned.

[51] Int. Cl.$^6$ .............. C12Q 1/68; C12P 19/34; C12N 15/85; C07H 21/04

[52] U.S. Cl. .............. 435/6; 435/69.8; 435/91.5; 435/320.1; 935/77; 935/78

[58] Field of Search .............. 435/6, 91.5, 69.8, 435/320.1; 935/77, 78

[56] References Cited

U.S. PATENT DOCUMENTS

| | | |
|---|---|---|
| 4,535,058 | 8/1985 | Weinberg et al. . |
| 4,601,978 | 7/1986 | Karin . |
| 4,699,877 | 10/1987 | Cline et al. . |
| 4,736,866 | 4/1988 | Leder et al. . |
| 4,738,922 | 4/1988 | Haseltine et al. . |
| 4,740,461 | 4/1988 | Kaufman . |
| 4,740,463 | 4/1988 | Weinberg et al. . |
| 4,761,367 | 8/1988 | Edgell et al. . |
| 4,761,371 | 8/1988 | Bell et al. . |
| 4,806,463 | 2/1989 | Goodchild et al. . |

(List continued on next page.)

FOREIGN PATENT DOCUMENTS

| | | |
|---|---|---|
| 117058 | 8/1984 | European Pat. Off. . |
| 332104 | 9/1989 | European Pat. Off. . |
| WO8902472 | 5/1989 | WIPO . |

OTHER PUBLICATIONS

Andersen, R. et al. (1990) "Metal–Dependent Binding of A Nuclear Factor to the Rat Metallothionein–I Promoter," Nucleic Acids Research 18(20):6049–6055.

Angel, P. et al., (1987 A) "Phorbol Ester–Inducible Genes Contain A Common Cis Element Recognized by An TPA–Modulated Trans–Acting Factor," Cell 49:729–739.

Angel, P. et al., (1987 B) "12–O–Tetradecanoyl–Phorbol–13–Acetate Induction of the Human Collagenase Gene Is Mediated by an Inducible Enhancer Element Located in the 5'–Flanking Region," Molecular and Cellular Biology, 7:2256–2266.

(List continued on next page.)

*Primary Examiner*—Stephanie W. Zitomer
*Attorney, Agent, or Firm*—John P. White; Cooper & Dunham LLP

[57] ABSTRACT

The invention provided for a method of transcriptionally modulating the expression of a gene encoding a protein of interest associated with treatment of one or more symptoms of a cardiovascular disease. Further provided is a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. Screening methods, including methods of essentially simultaneously screening molecules to determine whether the molecules are capable of directly and specifically transcriptionally modulating one or more genes encoding proteins of interest associated with treatment of one or more symptoms of a cardiovascular disease, are also provided.

7 Claims, 42 Drawing Sheets

U.S. PATENT DOCUMENTS

| | | |
|---|---|---|
| 4,810,643 | 3/1989 | Souza. |
| 4,827,079 | 5/1989 | Evans et al.. |
| 4,861,709 | 8/1989 | Ulitzer et al.. |
| 4,885,238 | 12/1989 | Reddel et al.. |
| 4,935,363 | 6/1990 | Brown et al.. |
| 4,981,783 | 1/1991 | Augenlicht. |
| 4,981,790 | 1/1991 | Haseltine et al.. |
| 5,070,012 | 12/1991 | Nolan et al.. |
| 5,071,773 | 12/1991 | Evans et al.. |
| 5,075,229 | 12/1991 | Hanson et al.. |
| 5,262,300 | 11/1993 | Evans et al.. |

OTHER PUBLICATIONS

Bickel, M. et al., (1988) "Granulocyte–Macrophage Colony–Stimulating Factor Regulation in Murine T Cells and Its Relation to Cyclosporin A," Ex. Hematol. 16:691–695.

Blumberg, P., (1988) "Protein Kinase C as the Receptor for the Phorbol Ester Tumor Promoters: Sixth Rhoads Memorial Award Lecture," Cancer Research 48:1–8.

Brasier, A. et al., (1989) "Optimized Use of the Firefly Luciferase Assay as a Reporter Gene in Mammalian Cell Lines," BioTechniques 7(10):1116–1122.

Brenner C. et al., (1989) "Message Amplification Phenotyping (MAPPing): A Technique to Simultaneously Measure Multiple mRNAs from Small Numbers of Cells," BioTechniques 7(10):1096–1103.

Cao, T., (1989) "A Simple and Inexpensive System to Amplify DNA by PCR," BioTechniques 7(6):566–567.

Cohen, P. and Foulkes, J.G. eds., (1991) *The Hormonal Control of Gene Transcription*, 92–93, 235–236.

Comb, M. et al. (1986) "A Cyclic AMP– and Phorbol Ester–Inducible DNA Element," Nature 323:353–356.

Connelly, C. et al., (1989) "The Role of Transgenic Animals in the Analysis of Various Biological Aspects of Normal and Pathologic States," Experimental Cell Research 183:257–276.

Cybulsky, M. et al., (1991) "Gene Structure, Chromosomal Location, and Basis for Alternative mRNA Splicing of the Human VCAM1 Gene," Proc. Natl. Acad. Sci. USA 88:7859–7863.

Das, H. et al., (1988) "Cell Type–Specific Expression of the Human ApoB Gene Is Controlled by Two Cis–Acting Regulatory Regions," Journal of Biological Chemistry 263(23):11452–11458.

de Wet et al., (1987) "Firefly Luciferase Gene: Structure and Expression in Mammalian Cells," Molecular and Cellular Biology 7(2):725–737.

Emmel, E. et al., (1989) "Cyclosporin A Specifically Inhibits Function of Nuclear Proteins Involved in T Cell Activation," Science 246: 1617–1620.

Engebrecht, J. et al., (1985) "Measuring Gene Expression with Light," Science 227: 1345–1347.

Giguere et al. (Mar. 15, 1985) Nature 330: 624–629.

Gunter, K. et al., (1989) "Cyclosporin A–Mediated Inhibition of Mitogen–Induced Gene Transcription Is Specific for the Mitogenic Stimulus and Cell Type," Journal of Immunology 142:3286–3291.

Higuchi, K., et al., (1988) "Tissue–Specific Expression of Apolipoprotein A–I (ApoA–I) Is Regulated by the 5'–Flanking Region of the Human ApoA–I Gene," Journal of Biological Chemistry 263(34): 18530–18536.

Holbrook, N. et al., (1984) "T–Cell Growth Factor: Complete Nucleotide Sequence and Organization of the Gene in Normal and Malignant Cells," Proc. Natl. Acad. Sci. USA 81:1634–1638.

Hsu, M. et al., (1991) "Inhibition of HIV Replication in Acute and Chronic Infections in Vitro by a Tat Antagonist," Science, 254: 1799–1802.

Ishii, S. et al., (1985) "Characterization and Sequence of the Promoter Region of the Human Epidermal Growth Factor Receptor Gene," Proc. Natl. Acad. Sci. USA 82: 4920–4924.

Kaushansky, K. et al., (1985) "Genomic Cloning, Characterization, Multilineage Growth–Promoting Activity of Human Granulocyte–Macrophage Colony–Stimulating Factor," Proc. Natl. Acad. Sci. USA 83: 3101–3105.

Kawasaki, E. et al., (1985) "Molecular Cloning of a Complementary DNA Encoding Human Macrophage–Specific Colony–Stimulating Factor (CSF–1)," Science 230: 291–296.

Knott, T. et al., (1986) "Complete Protein Sequence and Identification of Structural Domains of Human Apolipoprotein B," Nature 323: 734–738.

Kronke, M. et al., (1984) "Cyclosporin A Inhibits T–Cell Growth Factor Gene Expression at the Level of mRNA Transcription," Proc. Natl. Acad. Sci. USA 81: 5124–5218.

Ladner, M. et al., (1987) "Human CSF–1: Gene Structure and Alternative splicing of mRNA Precursors," The EMBO Journal 6 (9): 2693–2698.

Lamb, P. et al., (1986) "Characterization of the Human p53 Gene," Molecular and Cellular Biology 6(5): 1379–1385.

Lee, M–T. et al. (1990) Biol. Abstr. 89(10): AB–100645.

Lefevre, C. et al., (1987) "Tissue–Specific Expression of the Human Growth Hormone Gene Is Conferred in Part by the Binding of a Specific Trans–Acting Factor," The EMBO Journal 6(4): 971–981.

Lim, K. et al., (1989) "A Simple Assay for DNA Transfection by Incubation of the Cells in Culture Dishes with Substrates for Beta–Galactosidase," BioTechniques 7(6): 576–579.

Lin, F. et al., (1985) "Cloning and Expression of the Human Erythropoietin Gene," Proc. Natl. Acad. Sci. USA 82: 7580–7584.

Majesky, M. et al., (1990) "PDGF Ligand and Receptor Gene Expression during Repair of Arterial Injury," Journal of Cell Biology 111: 2149–2158.

Maniatis, T. et al., (1987) "Regulation of Inducible and Tissue–Specific Gene Expression," Science 236: 1237–1245.

Mayo, K. et al., (1982) "Altered Regulation of the Mouse Metallothionein–I Gene Following Gene Amplification or Transfection," (in *Gene Amplification*) Schimke, R.T. ed., 67–73.

McCall, C. et al., (1989) "Biotherapy: A New Dimension in Cancer Treatment," Bio/Technology 7:231–240.

Metzler, D., (1977) *Biochemistry: The Chemical Reactions of Livings Cells*, 116–117.

Munjaal, R. et al., (1989) "In Situ Detection of Progesterone Receptor mRNA in the Chicken Oviduct Using Probe–on Slides," BioTechniques 7(10): 1104–1108.

Myoken, Y. et al., (1991) "Vascular Endothelial Growth Factor (VEGF) Produced by A–431 Human Epidermoid Carcinoma Cells and Identification of VEGF Membrane Binding Sites," Cell Biology 88: 5819–5823.

Nagata, S. et al., (1986) "The Chromosomal Gene Structure and Two mRNAs for Human Granulocyte Colony–Stimulating Factor," The EMBO Journal 5(3): 575–581.

Neuhold et al. (1986) DNA 5(5): 403–411 abstract.

Nimer, S. et al., (1988) "Serum Cholesterol–Lowering Activity of Granulocyte–Macrophage Colony–Stimulating Factor," JAMA 260(22): 3297–3300.

Nishizuka, Y., (1986) "Studies and Perspectives of Protein Kinase C," Science 233:305–312.

Paul, W. (1984) *Fundamental Immunology*, 275–276.

Pons, M. et al., (1990) "A New Cellular Model of Response to Estrogens: A Bioluminescent Test to Characterize (Anti)Estrogen Molecules," BioTechniques 9(4): 450–459.

Rao, A. et al., (1990) "A Quantitive Assay for β–D–Glucuronidase (GUS) Using Microtiter Plates," BioTechniques 8(1):38–40.

Ratner, M., (1989) "Can the Antisense Message Be Delivered?," Bio/Technology 7:207.

Reisman, D. et al., (1989) "Two Promoters that Map to 5'–Sequences of the Human p53 Gene Are Differentially Regulated during Terminal Differentiation of Human Myeloid Leukemic Cells," Biol. Abstr. 88(9): AB–673.

Rinkus, S. et al., (1980) "The Need for Both in Vitro and in Vivo Systems in Mutagenicity Screening," in *Chemical Mutagens*, de Serres et al. ed., 6: 365–473.

Roesler, W. et al., (1988) "Cyclic AMP and the Induction of Eukaryotic Gene Transcription," Journal of Biological Chemistry 263 (19): 9063–9066.

Sambrook, J. et al., (1989) "Strategies for Studying Gene Regulation," *Molecular Cloning: A Laboratory Manual*, 2nd Ed., 16.56–16.58.

Sequin, C. et al., (1987) "Regulation in Vitro of Metallothionein Gene Binding Factors," Science 235: 1383–1387.

Singleton, P. et al., (1987) Dictionary of Microbiology and Molecular Biology, pp. 314 and 382.

Slack, J. et al., (1989) "Application of the Multiscreen System to Cytokine Radioreceptor Assays," BioTechniques 7(10): 1132–1138.

Standaert, R. et al., (1990) "Molecular Cloning and Overexpression of the Human FK506–Binding Protein FKBP," Nature 346:671–674.

Stanley, E. et al., (1985) "The Structure and Expression of the Murine Gene Encoding Granulocyte–Macrophage Colony Stimulating Factor: Evidence for Utilisation of Alternative Promoters," The EMBO Journal 4(10): 2569–2573.

Stinski, M. et al. "Activation of the Major Immediate Early Gene of Human Cytomegalovirus by Cis–Acting Elements in the Promoter–Regulatory Sequence and by Virus–Specific Trans–Acting Components," Journal of Virology 55(2): 431–441.

Tal, M. et al., (1987) "Human HER2 (neu) Promoter: Evidence of Multiple Mechanisms for Transcriptional Initiation," Molecular and Cellular Biology 7(7): 2597–2601.

Tamura, R. et al. (1988) Chemical Abstracts 108 (15): AB–124167.

Tischer, E. et al., (1991) "The Human Gene for Vascular Endothelial Growth Factor," Journal of Biological Chemistry 266 (18): 11947–11954.

Tocci, M. et al. "The Immunosuppressanat FK506 Selectively Inhibits Expression of Early T Cell Activation Genes," Journal of Immunology 143(2): 718–726.

Vellenga, E. et al. (1988) "Independent Regulation of MCSF and G–CSF Gene Expression in Human Moncytes" Blood 71(6): 1529–1532.

Willingham, M. et al., (1990) "A Reversible Multi–Well Chamber for Incubation of Cultured Cells with Small Volumes: Application to Screening of Hybridoma Fusions Using Immunofluorescence Microscopy," BioTechniques 8(3): 320–324.

Wu, K. et al. "Aspirin Inhibits Interleukin 1–Induced Prostaglandin H Synthase Expression in Cultured Endothelial Cells" Proc. Natl. Acad. Sci. USA 88:2384–2397.

Yang, Y. et al. (1986) "Human IL–3 (Multi–CSF): Indentification by Expression Cloning of a Novel Hematopoietic Growth Factor Related to Muring IL–3" Cell 47:3–10.

Features of the Mammalian Vector
pUV102 with Inserted TK-NEO Cassette.

Figure 5 pUV1:
5'TCGACCCGGGGGCCGGCTGATCAGAACGTCGGGCCGGTACCGTGCACTACGTAAGATCTAAGCTT3' pUV2:
5'ACTAGTCTGCAGGCTAGCACTCTCTGGTCCCCACAGACTCAGAGAGAACCCACCATGA3' pUV3:
5'AGACGCCAAAAACATCAAGAAAAGGCCCGGCCATTCTATCCTCTAGAGGGGATCCAGCTG3' pUV4:
5'TAGATCTTACGTAGTGCACGGTACCGGCCCGACGTCGATCAGCGGCCGCCCGGG3' pUV5:
5'GGTGGGTTCTCTCTGAGTCTGTGGGACCAGAGAGTGCTAGCCTGCGACTAGTAAGCT3' pUV6:
5'AATTCAGCTGGATCCCCTCTAGAGGATAGAATGGCCGGGCCTTTCTTGATGTTTTTGGCGTCTTCCAT3'

Figure 10A

Oligo #1: 5'- AGCTTGGCCCCTAGGGCCACTAGTCTGCAGCTATGATGACACAA
ACCCCGCCCCAGCGGTCTTGTCATTGGCGA-3'

Oligo #2: 3'- ACCGGGGATCCCGGTGATCAGACTCGATACTACTGTGTTTGGGG
CGGGGTCGCAGAACAGTAACCGCTTAAGCT-5'

Oligo #3: 5'- ATTCGAACACGCAGATGCAGTCGGGGCGGCGCGGTCCGAGGTC
CACTTCGCATATTAAGGTGACGCGTGTGGG-3'

Oligo #4: 3'- TGTGCGTCTACGTCAGCCCCGCCGCGCCAGGCTCCAGGTGAAG
CGTATAATTCCACTGCGCACACCCGATC-5'

Figure 10B

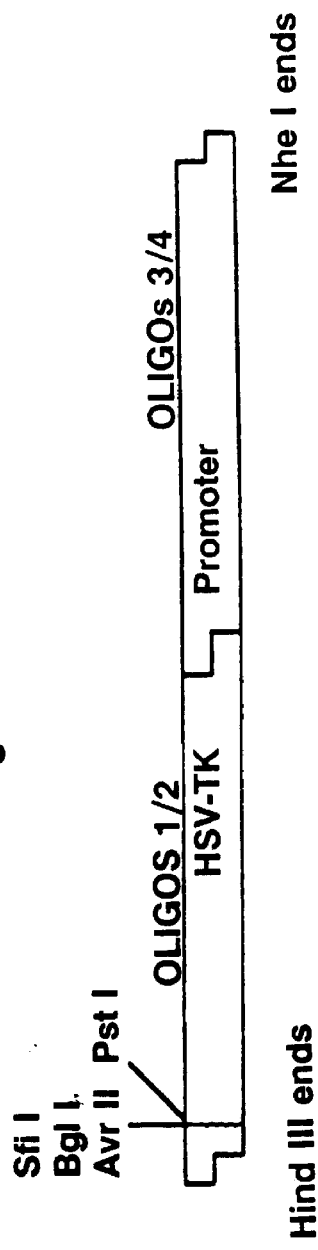

β-Fibrinogen

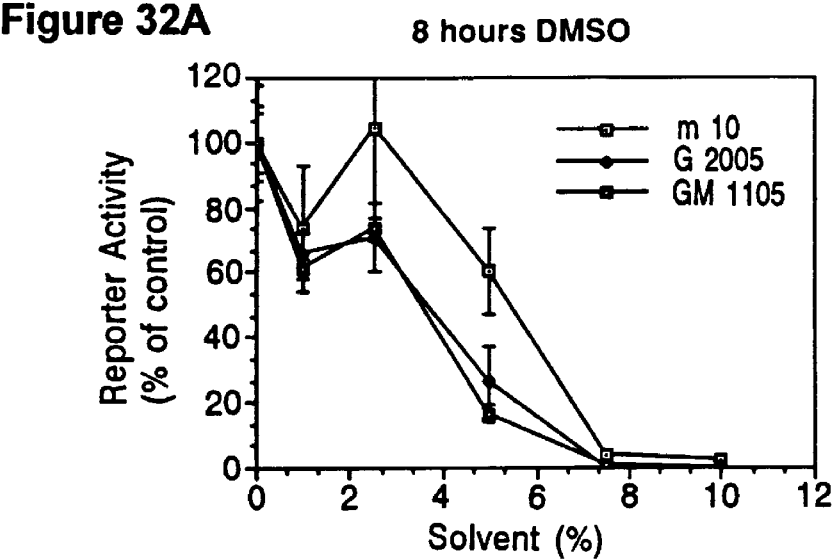
Figure 32A  8 hours DMSO
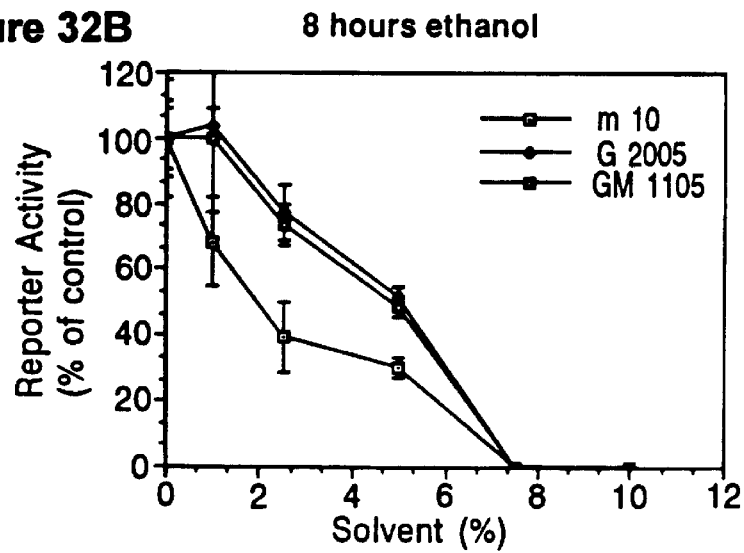
Figure 32B  8 hours ethanol
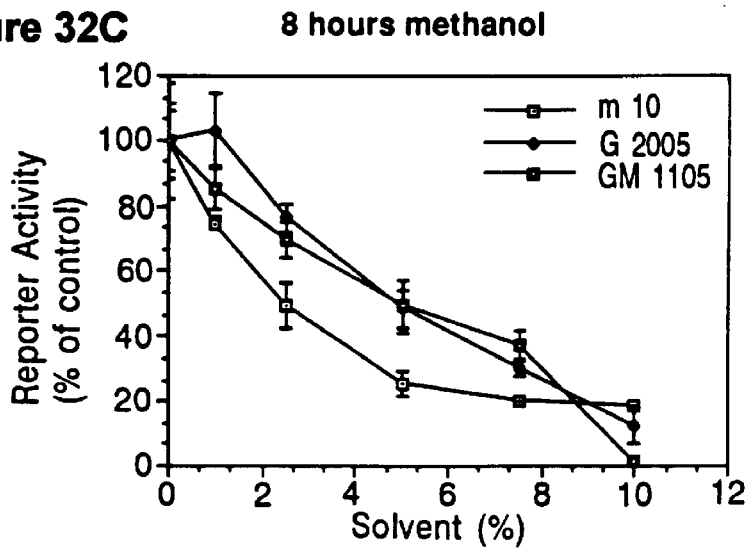
Figure 32C  8 hours methanol Average Negative RCOV
SP000011 - Avg. RCOV

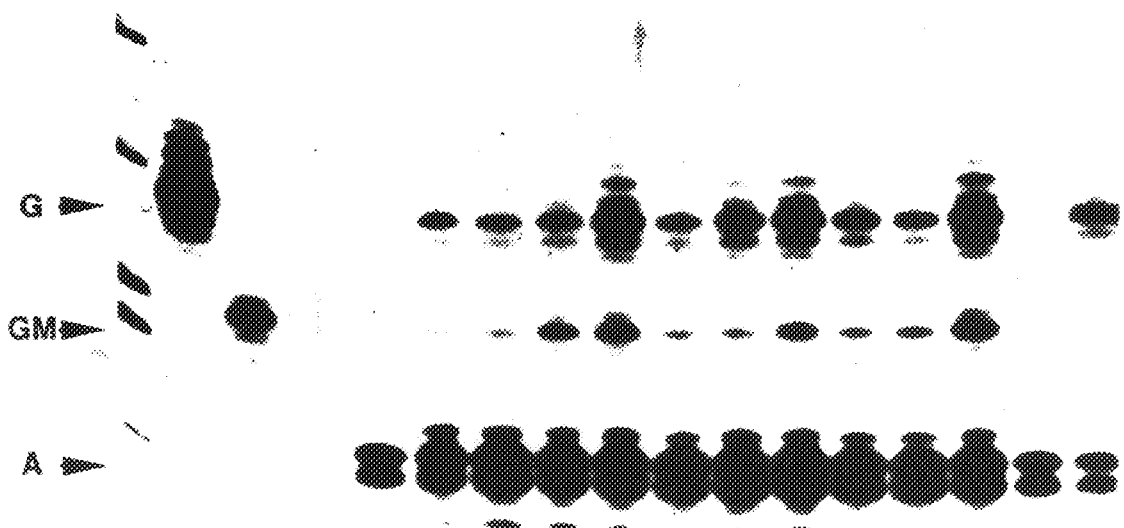

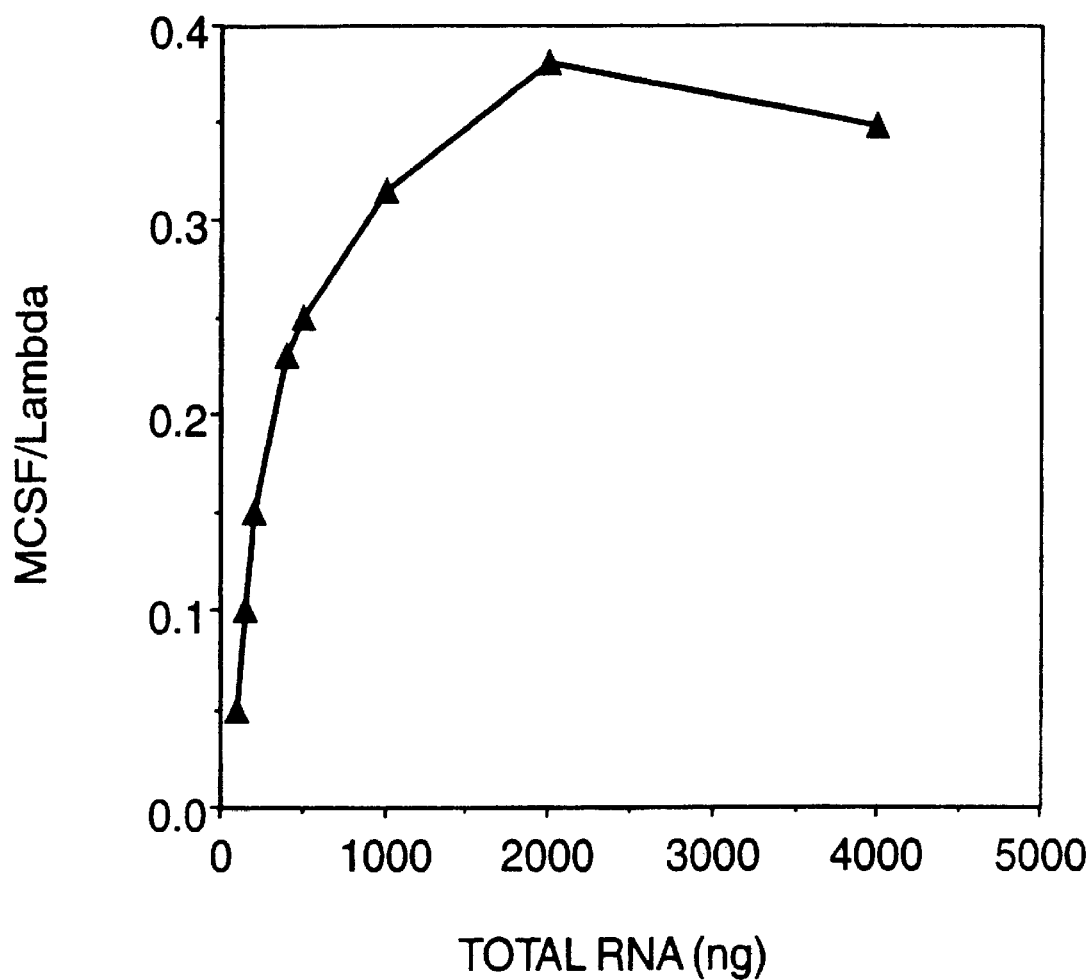

METHODS OF DETERMINING CHEMICALS THAT MODULATE EXPRESSION OF GENES ASSOCIATED WITH CARDIOVASCULAR DISEASE

This application is a continuation of U.S. Ser. No. 07/832,905, filed Feb. 7, 1992, now U.S. Pat. No. 5,580,722, which was a continuation-in-part of U.S. Ser. No. 07/555,196, filed Jul. 18, 1990, now abandoned, which was a continuation-in-part of U.S. Ser. No. 07/382,712, filed Jul. 18, 1989, now abandoned, and is related to PCT/US90/04021, now abandoned, the contents of which are hereby incorporated by reference into the present application.

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

1. Cardiovascular Disease

The two most prevalent causes of death in Western civilization, myocardial and cerebral infarctions, are primarily the result of atherosclerotic lesions. Atherosclerosis is a disease of artery walls, which typically affects the major arteries supplying the heart and brain with oxygen and nutrients. It causes a thickening of artery walls which can lead to restricted blood flow, thrombosis, and eventually myocardial infarction or stroke.

Angina is a common manifestation of the disease when it affects the vessels supplying the heart, and is caused by an imbalance in the cardiac blood supply and demand for oxygen, and vasoconstriction of the affected arteries.

Positive risk factors for the development of atherosclerosis, myocardial infarction and stroke include high serum cholesterol (in low density lipoprotein (LDL) or very low density lipoprotein (VLDL) particles), triglycerides, lipoprotein (a), or fibrinogen levels, hypertension, diabetes, smoking, age and a family history of cardiovascular disease. Negative risk factors include high density lipoprotein (HDL) cholesterol or apolipoprotein AI levels.

In advanced cases of the disease, the area of artery thickening, termed the atherosclerotic plaque, is characterized by a fibrous cap rich in connective tissue, a necrotic cholesterol-rich core, hyperproliferation of smooth muscle cells and macrophages, ulceration, intraplaque hemorrhage and thrombosis, and calcification.

The potential benefit from having effective inhibitors of atherosclerosis is enormous. About 900,000 people per year in the USA die from diseases caused by atherosclerosis (i.e. myocardial infarction, stroke), more than that from all cancers combined. The costs to society of this disease are estimated to be about $84 billion per year in the U.S.A. alone. Furthermore, in many parts of Europe the incidence of atherosclerosis-related disease is considerably higher than in the USA.

2. Atherosclerosis

Atherosclerotic lesions are typically characterized by the rapid local proliferation of vascular smooth muscle cells, deposition of intra- and extracellular lipid, and the accumulation of extracellular matrix components. Current evidence, largely from animal models and cellular studies, suggests the following pathway for atherogenesis; hypercholesterolemia is thought to result in increased levels of oxidized lipoproteins (e.g. oxidized LDL, possibly formed as a result of 15-lipoxygenase activity, (1), which can lead to abnormal localized expression of endothelial-monocyte cell adhesion molecules, and monocyte attachment to the endothelium and entry into the arterial wall (2, 3). These monocytes differentiate to macrophages and accumulate large quantities of cholesterol esters to become 'foam cells' (4). It is these cells which predominate in the 'fatty streak' lesion characteristic of this stage. Macrophages, vascular smooth muscle cells (SMCs), endothelial cells, and probably at a later stage adhering platelets, are thought to release growth and chemotactic factors which stimulate the uncontrolled proliferation, differentiation or migration of cells at the site of the lesion, particularly SMCs (4). bFGF (5), interleukin-1 (IL-1) (6), PDGF (7), colony-stimulating factor-1 (CSF-1), G-CSF, GM-CSF, monocyte chemoattractant protein-1 (MCP-1, (3, 8) and other factors have all been implicated in this process, and it is possible that many of these could play a role during the process of atherogenesis, either directly or indirectly, through independent actions or synergistically, possibly at different times during plaque development, or on different cell types. Many of these factors and their receptors have been directly measured in atherosclerotic tissue and found to be present at elevated levels compared to healthy arterial tissue, e.g. PDGF-B, PDGF β-receptors (9, 10). Several of these factors are released from macrophages or endothelial cells in response to oxidized LDL, cytokines e.g. IL-1, CSF-1 (3), G-CSF (8, 11), GM-CSF, MCP-1. Early progenitor cells of the macrophage lineage have been found in atherosclerotic plaques (12), and their stimulation by these CSFs may be at least partially responsible for the accumulation of large numbers of macrophages at plaques.

In human atherogenesis the situation may be slightly more complicated. Here at least two types of early lesions can be identified: fatty streak lesions, characterized by numerous fat filled cells, and focal intimal thickening, characterized by edema, smooth muscle cell proliferation and little or no accumulation of lipid (13). These two lesion types can occur quite independently or together, as observed in the lower abdominal aorta. In addition, fatty deposits, although common in Western society, may be missing in populations where other risk factors such as hypertension, cigarette smoking, and diabetes are associated with increased incidence of the disease. In all situations, however, it is clear that uncontrolled cellular proliferation is a major factor in advanced plaque formation, regardless of the initiating event (s), and that control of this proliferation by pharmacological intervention should be beneficial in controlling or preventing plaque formation.

In the United States, it is estimated that 10 million people suffer from diabetes mellitus, 60 million from hypertension, and 3 million from the combination of the two. Diabetic hypertension is associated with non insulin-dependent diabetes mellitus (NIDDM) or type II diabetes. Other cardiovascular diseases, especially atherosclerosis are also associated with diabetes. It is thought that the control of hyperglycemia might help the cardiovascular pathology associated with diabetes. Reducing gluconeogenesis is one way of reducing hyperglycemia. Insulin regulates the amount of serum glucose by promoting clearance in the skeletal muscle and at the same time preventing glucose production by inhibiting hepatic gluconeogenesis and glycogenolysis. The rate limiting step of gluconeogenisis is catalyzed by the enzyme phosphoenolpyruvate carboxykinase (PEPCK) which converts pyruvate to oxaloacetic acid. PEPCK levels are determined by insulin control by insulin. In the NIDDM condition, even hyperinsulinemia fails to inhibit PEPCK transcription leading to hyperglycemia. Therefore, pharmacological downregulation of PEPCK transcription is of potential therapeutic value for the clinical management of diabetic hypertension or for other cardiovascular diabetic diseases.

3. Cholesterol and Hypocholesterolemic Drugs

One of the leading risk factors for atherosclerosis is chronic hypercholesterolemia. A causal link between hypercholesterolemia due to elevated plasma concentrations of low-density lipoproteins (LDL) and very-low-density lipoprotein (VLDL) remnants and the premature development of atherosclerosis in humans is well established (14). Patients with hereditary disorders such as familial hypercholesterolemia are predisposed towards premature coronary artery disease. Long-term effective hypolipidemic therapy aimed at reducing plasma concentrations of atherogenic lipoproteins can prove beneficial not only for these patients but also for those with persistent hypercholesterolemia attributable to secondary disorders such as the nephrotic syndrome. Lowering of plasma concentration of both total and low-density lipoprotein, either by diet or drug therapy, has provided conclusive evidence that hypocholesterolemic therapy given to patients with primary hypercholesterolemia significantly reduces cardiovascular morbidity and mortality.

There are conditions in which diet alone cannot control serum cholesterol levels, for example, patients with hereditary disorders attributable to defects in receptor mediated LDL catabolism (familial hypercholesterolemia), those with hypercholesterolemia due to overproduction of VLDL and LDL by the liver (familial combined hyperlipidemia), patients with secondary hypercholesterolemia due to the nephrotic syndrome, as well as many adult patients with type III hyperlipoproteinemia. The combination of a bile sequestrant with a drug that inhibits the hepatic synthesis of cholesterol, VLDL, or LDL has been used. However, this regimen unfortunately cannot be tolerated by all patients and is not consistently effective. The Consensus Conference on Cholesterol concluded that there was a need for newer hypocholesterolemic agents that are effective, safe and encourage patient compliance.

The HMGCoA reductase inhibitors, such as mevastatin and lovastatin, have provided a potential new mode of therapy for patients with significant hypercholesterolemia that does not respond adequately to diet therapy alone. These HMGCoA reductase inhibitors reduce the rate of formation of mevalonic acid which leads to a depletion of the cellular pool of cholesterol. This, in turn, results in an increased number of hepatic LDL receptors which yields a further decrease in serum cholesterol level (15). Drugs such as lovastatin seem to be relatively effective, particularly when used in combination with bile sequestering compounds such as cholestyramine, but they are not without side effects. Gastrointestinal disturbances, including flatulence, diarrhea, constipation and nausea are the most frequently reported side effects. Abdominal pain, cramps, insomnia, rash and headache are also reported. Paradoxically, increased levels of HMGCoA reductase have been reported in animals treated with high doses of mevinolin. While there is no published data to indicate that this will happen in humans there is the possibility that prolonged treatment of hypercholesterolemia with an HMGCoA reductase inhibitor will lead to increased enzyme levels and ultimately to resistance to the drug. Changes in liver function tests have also lead to withdrawal of patients from lovastatin treatment and there is some concern over the development of cataracts. The use of cholesterol-lowering drugs is projected to increase significantly, and thus there is a continuing need for safe and effective drugs.

Two of the colony-stimulating factors, CSF-1 and GM-CSF, have been observed to exert profound decreases in serum cholesterol levels (16, 17) equal to or greater than that observed with inhibitors of HMGCoA reductase like lovastatin. For GM-CSF average decreases of 37%. were observed. Although the mechanism of these effects has yet to be determined, these factors could be potentially useful in the treatment of hypercholesterolemia and thus atherosclerosis.

There is increasing evidence that high levels of high density lipoproteins (HDL) are anti-atherogenic (18), probably due to their role in 'reverse cholesterol transport' which mediates the movement of cholesterol from the peripheral tissues back to the liver. Proteins involved in this process include apolipoproteins AI and AII (18, 19), lecithin-cholesterol acyl-transferase (LCAT)(20), cholesteryl ester transfer protein (CETP)(21), and HDL receptors (22). These proteins are all potential targets for pharmacological intervention. Other proteins involved in cholesterol metabolism such as acetyl CoA-cholesterol acyl transferase (23), cholesterol 7α-hydroxylase (24), and AMP-activated protein kinase and kinase kinase (25) are also likely targets for future drugs.

4. Hypertension and Antihypertensive Drugs

Hypertension is another of the leading risk factors for atherosclerosis (26), although the molecular mechanisms involved in its stimulation of atherogenesis have yet to be elucidated. The increased expression of PDGF β-receptors but not PDGF a-receptors in arterial smooth muscle cells in response to hypertension (27), and the increased PDGF-B transcription in endothelial cells in response to increased shear forces (28) may be involved in this process. Atherosclerotic arteries have also been observed to be defective in EDRF (Endothelial-Derived Relaxation Factor) mediated vasodilation (29). Studies with specific inhibitors of EDRF synthesis have indicated that the entire circulation is in a constant state of vasodilation due to the continuous release of this factor from endothelial cells. Some antihypertensives (e.g. β-blockers, nifedipine) have been demonstrated to be efficacious in preventing atherosclerosis from developing, but not necessarily in inducing regression of lesions that are already present.

Although treatment of high blood pressure has been successful in reducing the arteriolar complications such as brain hemorrhage from rupture of microaneurisms, lacunar strokes from occlusion of arterioles by fibrinoid necrosis or adrenal failure from hypertensive nephropathy, atherosclerotic complications such as myocardial infarction are not uniformly prevented by such treatment (26). Antihypertensive drugs have different effects on factors that might adversely affect atherosclerosis. For example, they can have adverse effects on lipoprotein profiles or hemodynamic factors that influence the occurrence of blood flow disturbances (26). It has been estimated that the magnitude of this adverse effect can be enough to completely offset the benefit of treating mild hypertension. Many antihypertensives also have other undesirable side effects. There is thus a continuing need for new antihypertensives for the treatment of cardiovascular disease.

The Calcitonin/Calcitonin gene-related peptide (CGRP) gene encodes the calcium lowering hormone Calcitonin (CCPI), the vascular relaxant neuropeptide, CGRP and a calcitonin carboxy-terminal peptide (CCPII) of unknown function (92).

The regulation of calcitonin gene expression is controlled at multiple levels. At the level of transcription, the expression of the calcitonin gene is enhanced by phorbol esters, cAMP analogues, 1,25-dihydroxy vitamin $D_3$ and dexamethazone (97). Glucocortoids enhance calcitonin mRNA level while lowering CGRP mRNA.

CGRP is a potent endogenous vasodilator. The peptide is released from perivascular nerve endings and can normally be detected in the circulation. CGRP levels in patients with essential hypertension is lower than in normal subjects (98). The decrease of CGRP is closely related with the severity of hypertension. CGRP has also been shown to modulate the vasopressor effects of norepinephrine and angiotensin II (99).

5. Stenosis and Restenosis

Invasive cardiovascular surgical procedures, such as percutaneous translumenal coronary angioplasty (PTCA, using a balloon catheter) and aorto-coronary bypass surgery (ACBS), that are currently employed in treating the coronary stenosis or occlusion caused by atherosclerosis represent a major therapeutic advance for managing coronary heart disease (CHD). However, the cellular proliferative response and associated intimal hyperplasia that can follow the damage to blood vessels that occurs with these procedures leads to complications which cannot be effectively controlled by presently available drugs, and can be more detrimental than the original condition. The development of these complications, termed restenosis (in the case of PTCA) or stenosis (in the case of ACBS), has similarities to the development of atherosclerosis. After vascular injury and the resulting de-endothelialization, one of the initial events in the development of stenosis is platelet adherence to the damaged area (30). There is good evidence from animal models that the accumulation of neointimal smooth muscle cells (SMC) which leads to restenosis is due to the chemotactic properties of platelet-derived PDGF (7, 31) (possibly via induction of a bFGF autocrine loop). Polyclonal antibodies specific for PDGF-AB inhibit restenosis. PDGF β-receptors are upregulated in SMCs at the stage in restenosis when they are migrating from the media to the intima (32). Basic FGF is an effective mitogen for vascular smooth muscle cells in the medial layer of the artery wall (5), but once they have migrated to the intima the major mitogenic signal is, as in atherogenesis, unknown.

The potential benefit of having effective inhibitors of stenosis or restenosis is considerable since 190,000 coronary angioplasties and about 330,000 aorto-coronary bypass surgeries are carried out each year in the USA alone. Stenosis or restenosis is a severe problem in about a third of these procedures, often requiring multiple surgeries, which at $7,500 for angioplasty and $30,000–40,000 for bypass surgery is an expensive process. An effective antistenotic drug might be one that prevents platelet adhesion to the site of injury (e.g. by stimulating EDRF-dependent guanylate cyclase or down-regulating cell adhesion molecules), stimulates re-endothelial growth (e.g. by stimulating VEGF production by vascular smooth muscle cells) or inhibits smooth muscle cell migration ( e.g. by down-regulating vascular smooth muscle cell PDGF receptors) or proliferation (e.g. by down-regulating vascular smooth muscle cell FGF receptors). A combination of such drugs would probably be most effective. Platelet inhibitors like aspirin, which can limit platelet aggregation but cannot inhibit platelet-endothelial adhesion, reduce restenosis rates slightly.

6. Thrombosis

It has been known for some time that thrombosis is just as important as atherogenesis in causing ischemic heart disease. Several studies have shown strong relationships between high levels of factor VII coagulant activity and fibrinogen, and subsequent risk of clinically manifest ischemic heart disease (33). In the prospective Northwick Park Heart Study high levels of fibrinogen were associated with mortality from all causes and the relationship between fibrinogen and incidence of coronary heart disease was stronger than that for cholesterol (34). High levels of fibrinogen are likely to predispose to thrombosis, since fibrinogen/ fibrin are constituents of atherosclerotic plaques, fibrinogen concentration is an important determinant of blood viscosity, and elevated levels of fibrinogen lead to an increase in platelet aggregation. Regarding the role of factor VII in heart disease, it is probably also not a coincidence that factor VII is the only clotting factor zymogen which has some biological activity, all of the others requiring to be activated before they can exert any functional effect. High levels of plasminogen activator inhibitor (PAI-1) have also been associated with myocardial infarction (35). There is an extensive literature indicating the efficacy of antithrombolytic treatment (e.g. aspirin, tPA, streptokinase, nitroglycerin) in reducing both the morbidity and mortality due to angina and myocardial infarction.

There are several mechanisms by which atherosclerotic plaques can become thrombogenic. Many of the substances produced by cells at plaques can stimulate the production of activators of coagulation, or inhibitors of fibrinolysis. For example, IL-1 and TNF-α produced by macrophages can stimulate the endothelial cell surface accumulation of tissue factor. Rupture of plaques at an advanced stage of formation also results in the release of tissue factor. Macrophage or platelet derived TGFβ, or macrophage-derived IL-1 and TNF-α also stimulate the production of PAI-1 in endothelial cells (36). Increased PAI-1 synthesis is also stimulated in vascular smooth muscle cells by PDGF-Bβ and TGFβ (37), which is particularly relevant to situations involving vascular injury where adhering platelets produce these factors.

7. Transcriptional Regulation—General

Pharmaceuticals which increase or decrease the expression of genes associated with cardiovascular diseases will have important clinical application for the treatment of a variety of diseases and conditions, including myocardial infarction, angina, stroke, hypertension, hypercholesterolemia, restenosis and diabetes. This invention includes a method for discovery of compounds which modulate the expression of these genes and describes the use of such compounds. The general approach is to screen compound libraries for substances which increase or decrease expression of genes associated with cardiovascular diseases.

Examples of such genes would include those for apolipoprotein (a), the protein component of the 'atherogenic' Lipoprotein (a) which is specific to this particle (38); apolipoprotein AI, the major protein component of high density lipoproteins (HDL), the 'antiatherogenic' lipoprotein component of serum (18); apolipoprotein B, the main protein component of LDL (39); LDL receptor, the major hepatic receptor for LDL which removes LDL from the circulation (40); scavenger receptor, a major receptor for the uptake of oxidized LDL by macrophages at atherosclerotic plaques (41); cholesterol 7α-hydroxylase, the rate-limiting enzyme in the hepatic conversion of cholesterol to bile acids, and thus its clearance from the body (24); vascular endothelial growth factor (VEGF), a potent and specific growth factor for endothelial cells, whose production by vascular smooth muscle cells may lead to repair of vascular damage (e.g. after angioplasty) (42); β-fibrinogen, the major precursor protein involved in the formation of thrombi (43); colony stimulating factor-1, the major factor involved in stimulating viability, proliferation and differentiation of cells in the mononuclear phagocyte series (e.g. monocytes, macrophages) (41); and monocyte chemoattractant protein-1 (MCP-1), a protein produced by vascular endothelial and smooth muscle cells in response to a variety of stimuli (e.g. oxidized LDL, IL-1), and postulated to be involved in stimulating migration of monocytes/macrophages into atherosclerotic plaques (3). In order to reduce atherosclerosis, or restenosis after balloon angioplasty, and thus alleviate the symptoms of cardiovascular disease, one would search for compounds which down-regulate the expression of the genes for apolipoprotein (a), apolipoprotein B, MCP-1, CSF-1, β-fibrinogen and scavenger receptor, and compounds which upregulate the expression of the genes for apolipoprotein AI, hepatic LDL receptor, cholesterol 7α-hydroxylase and VEGF.

Similarly, one would search for compounds which inhibit the expression of genes involved in the oxidation of LDL, such as 15-lipoxygenase (1); inhibit the expression of genes involved in smooth muscle cell proliferation or migration to the intima, such as PDGF or basic FGF (5, 7); inhibit the expression of genes involved in the biosynthesis of cholesterol such as HMGCOA reductase (25); inhibit the expression of cell adhesion molecule genes (e.g. VCAM-1 (2), vitronectin receptor) involved in adhesion of cells like macrophages and platelets to the endothelium; inhibit the expression of genes involved in formation or inhibition of the breakdown of thrombi, such as plasminogen activator inhibitor; inhibit the expression of genes whose inhibition would cause a reduction of hypertension, such as preprorenin or angiotensinogen (44).

The expression of a specific gene can be regulated at any step in the process of producing an active protein. Modulation of total protein activity may occur via transcriptional, transcript-processing, translational or post-translational mechanisms. Transcription may be modulated by altering the rate of transcriptional initiation or the progression of RNA polymerase (45). Transcript-processing may be influenced by circumstances such as the pattern of RNA splicing, the rate of mRNA transport to the cytoplasm or mRNA stability. This invention concerns the use of molecules which act by modulating the in vivo concentration of their target proteins via regulating gene transcription. The functional properties of these chemicals are distinct from previously described molecules which also affect gene transcription.

Researchers have documented the regulation of transcription in bacteria by low molecular weight chemicals (46, 47). Extracellular xenobiotics, amino acids and sugars have been reported to interact directly with an intracellular proteinaceous transcriptional activator or repressor to affect the transcription of specific genes.

Transcriptional regulation is sufficiently different between procaryotic and eucaryotic organisms so that a direct comparison cannot readily be made. Procaryotic cells lack a distinct membrane bound nuclear compartment. The structure and organization of procaryotic DNA elements responsible for initiation of transcription differ markedly from those of eucaryotic cells.

The eucaryotic transcriptional unit is much more complex than its procaryotic counterpart and consists of additional elements which are not found in bacteria. Eucaryotic transcriptional units include enhancers and other cis-acting DNA sequences (48, 49). Procaryotic transcription factors most commonly exhibit a "helix-turn-helix" motif in the DNA binding domain of the protein (50, 51). Eucaryotic transcriptional factors frequently contain a "zinc finger" (51, 52), "helix-loop-helix" or a "leucine zipper" (53) in addition to sometimes possessing the "helix-turn-helix" motif (54). Furthermore, several critical mechanisms at the post-transcriptional level such as RNA splicing and polyadenylation are not found in procaryotic systems (55, 56).

In higher eucaryotes, modulation of gene transcription in response to extracellular factors can be regulated in both a temporal and tissue specific manner (57). For example, extracellular factors can exert their effects by directly or indirectly activating or inhibiting transcription factors (57, 58).

Modulators of transcription factors involved in direct regulation of gene expression have been described, and include those extracellular chemicals entering the cell passively and binding with high affinity to their receptor-transcription factors. This class of direct transcriptional modulators include steroid hormones and their analogs, thyroid hormones, retinoic acid, vitamin $D_3$ and its derivatives, and dioxins, a chemical family of polycyclic aromatic hydrocarbons (52, 59, 60).

Dioxins are molecules generally known to modulate transcription, however, dioxins bind to naturally-occurring receptors which respond normally to xenobiotic agents via transcriptionally activating the expression of cytochrome P450, part of an enzyme involved in detoxification. Similarly, plants also have naturally occurring receptors to xenobiotics to induce defense pathways. For example, the fungal pathogen Phytophthora megasperma induces an antifungal compound in soybeans. Such molecules which bind to the defined ligand binding domains of such naturally occurring. receptors are not included on the scope of this invention.

The clinical use of steroid hormones, thyroid hormones, vitamin $D_3$ and their analogs demonstrates that agents which modulate gene transcription can be used for beneficial effects, although these agents can exhibit significant adverse side effects. Obviously, analogs of these agents could have similar clinical utility as their naturally occurring counterparts by binding to the same ligand binding domain of such receptors.

Indirect transcriptional regulation involves one or more signal transduction mechanisms. The regulation typically involves interaction with a trans-membrane signal transducing protein, the protein being part of a multistep intracellular signaling pathway, the pathway ultimately modulating the activity of nuclear transcription factors. This class of indirect transcriptional modulators include polypeptide growth factors such as platelet-derived growth factor, epidermal growth factor, cyclic nucleotide analogs, and mitogenic tumor promoters (61, 62, 63).

It is well documented that a large number of chemicals, both organic and inorganic, e.g. metal ions, can non-specifically modulate transcription.

Researchers have used nucleotide analogs in methods to modulate transcription. The mechanism involves incorporating nucleotide analogs into nascent mRNA or non-specifically blocking mRNA synthesis. Similarly, researchers have used alkylating agents, e.g. cyclophosphamide, or intercalating agents, e.g. doxorubicin, to non-specifically inhibit transcription.

Moreover, chemical inhibitors of hydroxymethyl-glutaryl CoA reductase, e.g. lovastatin, are known to modulate transcription by indirectly increasing expression of hepatic low density lipoprotein receptors as a consequence of lowered cholesterol levels.

The best examples of promoters subject to pharmaceutical intervention are provided by those of the steroid responsive genes. Nolvadex (Tamoxifen), for example, regulates the expression of estrogen responsive genes in the control of breast cancer, while Eulexin (flutamide) demonstrates dramatic palliative efficacy in the treatment of prostatic carcinoma by blocking the action of the testosterone receptor. Similarly, steroid receptor agonists are used as anti-inflammatory agents, contraceptives, etc. It is now becoming increasingly apparent that a number of drugs whose mechanism was previously unknown, also act by specifically modulating the expression of various target genes. For example, the immunosuppressive agents cyclosporin A and FK506, both inhibit the transcription of several genes involved in T cell activation, in particular interleukin 2 (64, 65). The cellular receptors for these compounds are the proteins termed cyclophilins, which may act, at least in part, by inhibiting the $Ca^{2+}$/calmodulin-dependent protein phosphatase calcineurin. Altered phosphatase activity presumably modulates gene expression by altering the phosphorylation state of specific transcription factors, or transcription factor activity modulators. The anti-inflammatory action of aspirin has also recently been shown to be at least partly due to altered levels of gene expression.

Signal effector type molecules such as cyclic AMP, diacylglycerol, and their analogs are known to regulate a broad spectrum of genes at the transcriptional level by acting as part of a multistep protein kinase cascade reaction. These signal effector type molecules bind to domains on proteins which are thus subject to normal physiological regulation by low molecular weight ligands (67, 68).

The specific use of sterol regulatory elements from the LDL receptor gene to control expression of a reporter gene has recently been documented in PCT/US88/10095. One aspect of PCT/US88/10095 deals with the use of specific sterol regulatory elements coupled to a reporter as a means to screen for drugs capable of stimulating cells to synthesize the LDL receptor. PCT/US88/10095 describes neither the concept of simultaneously screening large numbers of chemicals against multiple target genes nor the existence of transcriptional modulators which (a) do not naturally occur in the cell, (b) specifically transcriptionally modulate expression of the gene encoding the protein of interest associated with cardiovascular disease, and (c) directly bind to DNA or RNA, or directly bind to a protein through a domain of such protein which is not a defined ligand binding domain of a nuclear, transcriptionally activating receptor which naturally occurs in the cell, the binding of a ligand to which ligand binding domain is normally associated with the defined physiological effect. The main focus of PCT/US88/10095 is the use of the sterol regulatory elements from the LDL receptor as a means to inhibit expression of toxic recombinant biologicals.

The use of molecules to directly and specifically modulate transcription of genes associated with cardiovascular disease as described herein has not previously been reported and its use will be considered novel since available literature does not propose the use of a molecule, as described, in a method to specifically modulate transcription. Instead, the available literature has reported methods which define domains of transcriptional regulating elements of a gene.

Further, the practice of using a reporter gene to analyze nucleotide sequences which regulate transcription of a gene-of-interest is well documented. The demonstrated utility of a reporter gene is in its ability to define domains of transcriptional regulatory elements of a gene-of-interest. Reporter genes which express proteins, e.g. luciferase, are widely utilized in such studies. Luciferases expressed by the North American firefly, Photinus pyralis and the bacterium, Vibrio. fischeri were first described as transcriptional reporters in 1985 (69, 70).

A method to define domains of transcriptional regulating elements of a gene-of-interest typically has also involved use of phorbol esters, cyclic nucleotide analogs, concanavalin A, or steroids, molecules which are commonly known as transcriptional modulators. However, available literature shows that researchers have not considered using a transcription screen to identify specific transcriptional modulators. Apparently, success would be unlikely in doing so, however, we have demonstrated previously that this is not the case.

There is utility in developing the method of transcriptional modulation of genes associated with cardiovascular disease by using such molecules as described herein. This method will allow the development of novel pharmaceuticals and circumvent many of the problems associated with the therapeutic use of recombinant biological factors where clinical use of protein factors is relevant.

Problems associated with the therapeutic use of recombinant biological factors include the technical difficulties of large scale protein purification, the high costs of protein production, the limited shelf-life of most proteins and in some cases a short biological half-life of the administered protein in the organism. Additionally, therapeutic delivery of proteins normally requires injection and frequently induces an immune reaction in situations where chronic administration is required. The method described herein provides a means of up-regulating the expression of proteins which are not readily amenable to administration as injectable biologicals.

Another potential advantage of transcriptional modulation over a biological would be the production of high localized concentrations of proteins. For example, a major application of vascular endothelial growth factor (VEGF) (42) as a biological would presumably be in wound healing. A major application in this area would be in the treatment of vascular wounding caused by balloon angioplasty or coronary bypass surgery. A small molecule drug upregulating VEGF gene expression would have advantages over the biological. Increased gene expression and secretion of VEGF by vascular smooth muscle cells which are present at the site of injury would lead to high local concentrations of VEGF. This would stimulate re-endothelialization, thus preventing platelet adhesion, and therefore stenosis or restenosis (43). Large doses of a biological would have to be given intravenously or intramuscularly to produce an effect similar to the locally produced paracrine-acting factor. There would thus be a greater likelihood of incurring side effects such as abnormal vascularization, or edema due to the vascular permeabilizing properties of VEGF.

Furthermore, chemical molecules specifically regulating the activity of one member of a group of closely related proteins are difficult to produce. Bioactive molecules, structurally related at the protein level, may possess distinct regulatory elements at the DNA level which control their expression. Thus, molecules such as the chemical transcriptional modulators defined herein can provide a greater opportunity for specifically modulating the activity of structurally related proteins. Finally, the molecules described herein may also serve to mimic normal physiological response mechanisms, typically involving the coordinated expression of one or more groups of functionally related genes. Therefore, determining whether a molecule can specifically transcriptionally modulate the expression of a gene involved in cardiovascular disease and the ultimate clinical use of the molecule provides a therapeutic advantage over the use of single recombinant biologicals, or drugs which bind directly to the final target protein encoded by the gene-of-interest.

There is considerable evidence from the literature to indicate that many of the genes involved in cardiovascular disease are regulated in vivo at the transcriptional level. For example modulation of the transcription of the gene coding for apolipoprotein AI can be achieved by thyroid hormone or cholesterol (71, 72). Similarly, LDL receptor gene expression can be modulated by cholesterol metabolites, cholesterol 7α-hydroxylase by bile acids (73), CSF-1 by gamma-interferon (74), MCP-1 by minimally-modified LDL, gamma-interferon, TNF-α or interleukin-1 (75), and β-fibrinogen by glucocorticoids and interleukin-6 (76).

SUMMARY OF THE INVENTION

The invention provides a method of directly and specifically transcriptionally modulating the expression of a gene encoding a protein of interest, the expression of which gene is associated with treatment of one or more symptoms of a cardiovascular disease in a human being. This method comprises contacting a cell, which is capable of expressing the gene, with a molecule at a concentration effective to transcriptionally modulate expression of the gene and thereby affect the level of the protein of interest encoded by the gene which is expressed by the cell. In this method the molecule (a) does not naturally occur in the cell, (b) specifically transcriptionally modulates expression of the gene encoding the protein of interest, and (c) directy binds to DNA or RNA, or directly binds to a protein at a site on such protein which is not a ligand-binding domain of a receptor which naturally occurs in the cell, the binding of a ligand to which ligand-binding domain is normally associated with a defined physiological or pathological effect.

This invention further provides a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a DNA sequence encoding a polypeptide other than the protein of interest, which polypeptide being capable of producing a detectable signal. The DNA sequence is coupled to, and under the control of, the promoter, under conditions such that the molecule, if capable of acting as a transcriptional modulator of the gene encoding the protein of interest, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the molecule as one which causes a change in the detectable signal produced by the polypeptide so expressed, and thus identifying the molecule as a molecule capable of directly and specifically transcriptionally modulating the expression of the gene encoding the protein of interest.

This invention still further provides a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a reporter gene, which expresses a polypeptide. The reporter gene is coupled to, and under the control of, the promoter, under conditions such that the molecule, if capable of acting as a transcriptional modulator of the gene encoding the protein of interest, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the molecule as one which causes a change in the detectable signal produced by the polypeptide so expressed, and thus identifying the molecule as a molecule capable of directly and specifically transcriptionally modulating the expression of the gene encoding the protein of interest.

This invention still further encompasses a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a DNA sequence transcribable into mRNA coupled to and under the control of, the promoter. The contacting is under conditions such that the molecule, if capable of acting as a transcriptional modulator of the protein of interest, causes a measurable difference in the amount of mRNA transcribed from the DNA sequence. This method allows for the quantitative determination of the amount of the mRNA produced. By comparing the amount so determined with the amount of mRNA detected in the absence of any molecule being tested or upon contacting the sample with any other molecule, one can thereby identify the molecule as one which causes a change in the detectable mRNA amount of, and thus identifying the molecule as a molecule capable of directly and specifically transcriptionally modulating the expression of the gene encoding the protein of interest.

A screening method is also provided. This screening method comprises separately contacting each of a plurality of substantially identical samples, each sample containing a predefined number of cells under conditions such that contacting is affected with a predetermined amount of each different molecule to be tested.

Also disclosed is a method of essentially simultaneously screening molecules to determine whether the molecules are capable of transcriptionally modulating one or more genes encoding proteins of interest which comprises essentially simultaneously screening the molecules against the genes encoding the proteins of interest according to the methods mentioned above.

A method for directly and specifically transcriptionally modulating in a multicellular organism the expression of a gene encoding a protein of interest, the expression of which is associated with treatment of one or more symptoms of a cardiovascular disease in a human being, is also provided. This method comprises administering to the human being a molecule at a concentration effective to transcriptionally modulate expression of the protein of interest and thus ameliorating the cardiovascular disease. In this method the molecule (a) does not naturally occur in a human being, (b) specifically transcriptionally modulates expression of the gene encoding the protein of interest, and (c) directy binds to DNA or RNA, or directly binds to a protein at a site on such protein which is not a ligand-binding domain of a receptor which naturally occurs in the cell, the binding of a ligand to which ligand-binding domain is normally associated with a defined physiological or pathological effect.

BRIEF DESCRIPTION OF THE FIGURES

FIG. 5 provides the nucleotide sequences of six oligonucleotides, pUV-1 through pUV-6, which were annealed, ligated, and inserted into the SalI/EcoRI sites of the plasmid pTZ18R.

FIGS. 10A–10B provide the nucleotide sequences of oligos 1–4 used for the construction of a synthetic HSV-thymidine kinase promoter and provides a diagrammatic representation of the HSV-TK promoter.

FIGS. 32A, 32B & 32C represent the inhibition of reporter activity at varying concentrations of commonly used solvents. Three solvents are tested against three cell lines.

FIG. 37 is an autoradiograph of a polyacrylamide gel illustrating an S1 nuclease protection analysis of increased mRNA production by the human bladder carcinoma cell line 5637 in response to lead chemicals #542, #1255, #1793 and #1904. "RNA" indicates the sources of the RNA preparations used in individual lanes. "Probe" indicates the mRNA-specificities of probes used in individual lanes. "Compound" lists the compounds with which the 5637 cells were treated prior to RNA extraction and loading on individual gel lanes ("Cyclo" means cycloheximide). "Conc" indicates three different compound concentrations used in the experiment (L=low, M=medium, H=high). G, GM and A indicate the correct sizes of G-CSF-, GM-CSF- and Actin-specific nuclease-protected mRNA/Probe hybrids.

FIG. 42 is an interpretation of the data presented in FIG. 41. Relative band intensity of the M-CSF band is plotted against the initial M-CSF concentration.

Figure 1:
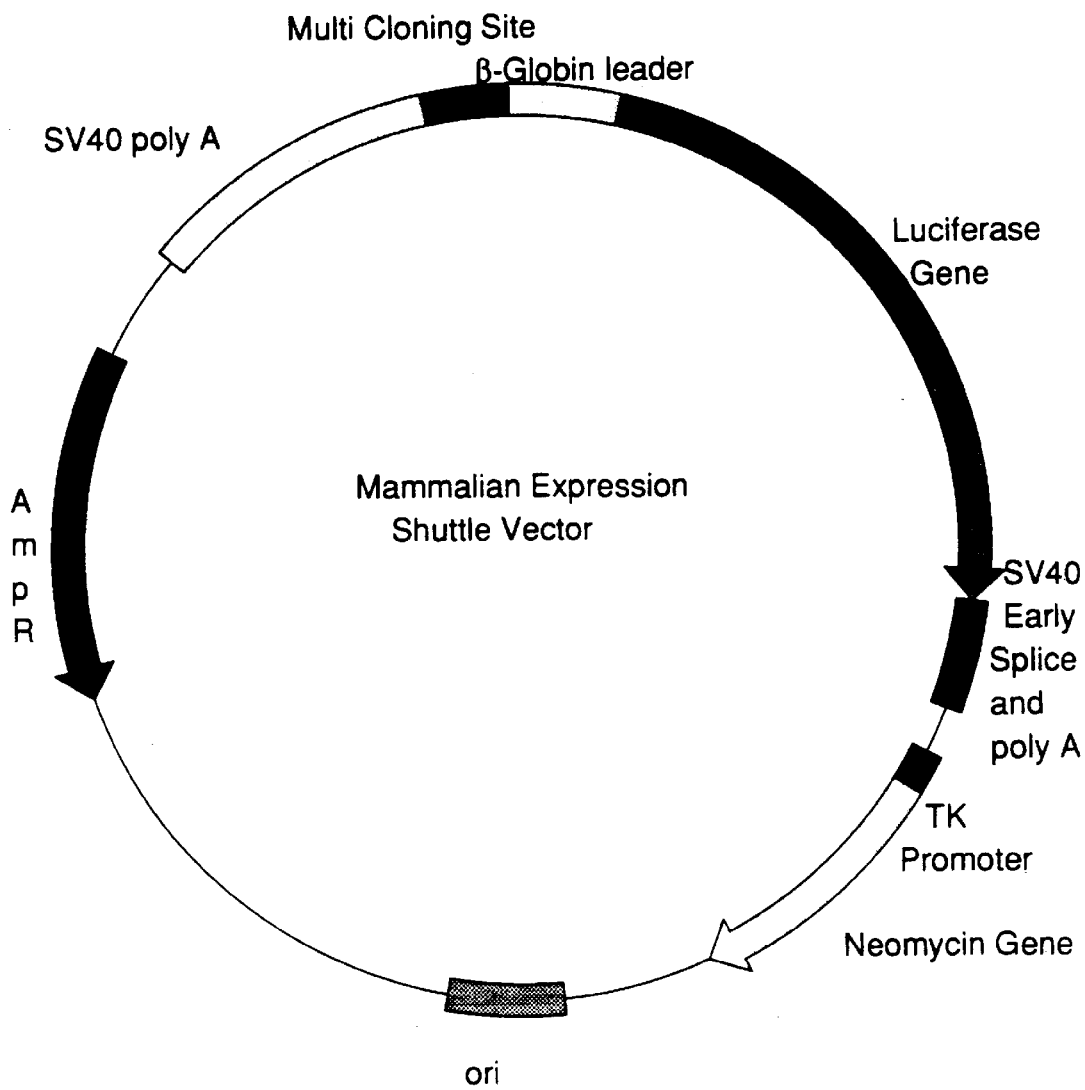
FIG. 1 is a view of the mammalian expression shuttle vector pUV102 with its features. The mammalian expression shuttle vector was designed to allow the construction of the promoter-reporter gene fusions and the insertion of a neomycin resistance gene coupled to the herpes simplex virus thymidine kinase promoter (TK-NEO).

* Abbreviations used in the figures: pGEM5Zf (+), PGEM7Zf(+)=Promega Riboprobe Gemini general purpose cloning vector. pUV102=OSI mammalian expression shuttle vector without the neomycin resistance gene. f1 ori=origin of replication for the filamentous bacteriophage f1. amp 4=ampicillin resistance gene. Col E1 ori=plasmid origin of replication. SV40 polyA+Simian Virus 40 polyadenylation signal. splice site=Simian Virus 40 early RNA splice site. lacZ=lacZ α-peptide coding region for complementation of the lacZ▲15 gene to produce functional β-galactosidase. neo=neomycin resistance gene. HSVTK=Herpes Simplex Virus thymidine kinase promoter. luciferase=firefly luciferase coding and 3' regions.

DETAILED DESCRIPTION OF THE INVENTION

As used in this application, the following words or phrases have the meanings specified.

Antisense nucleic acid means an RNA or DNA molecule or a chemically modified RNA or DNA molecule which is complementary to a sequence present within an RNA transcript of a gene.

Directly transcriptionally modulate the expression of a gene means to transcriptionally modulate the expression of the gene through the binding of a molecule to (a) the gene (b) an RNA transcript of the gene, or (c) a protein which binds to (i) such gene or RNA transcripts, or (ii) a protein which binds to such gene or RNA transcript.

A gene means a nucleic acid molecule, the sequence of which includes all the information required for the normal regulated production of a particular protein, including the structural coding sequence, promoters and enhancers.

Indirectly transcriptionally modulate the expression of a gene means to transcriptionally modulate the expression of such gene through the action of a molecule which cause enzymatic modification of a protein which binds to (a) the gene or (b) an RNA transcript of the gene, or (c) protein which binds to (i) the gene or (ii) an RNA transcript of the gene. For example, altering the activity of a kinase which subsequently phosphorylates and alters the activity of a transcription factor constitutes indirect transcript modulation.

Ligand means a molecule with a molecular weight of less than 5,000, which binds to a transcription factor for a gene. The binding of the ligand to the transcription factor transcriptionally modulates the expression of the gene.

Ligand binding domain of a transcription factor means the site on the transcription factor at which the ligand binds.

Modulatable transcriptional regulatory sequence of a gene means a nucleic acid sequence within the gene to which a transcription factor binds so as to transcriptionally modulate the expression of the gene.

Receptor means a transcription factor containing a ligand binding domain.

Specifically transcriptionally modulate the expression of a gene means to transcriptionally modulate the expression of such gene alone, or together with a limited number of other genes.

Transcription means a cellular process involving the interaction of an RNA polymerase with a gene which directs the expression as RNA of the structural information present in the coding sequences of the gene. The process includes, but is not limited to the following steps: (a) the transcription initiation, (b) transcript elongation, (c) transcript splicing, (d) transcript capping, (e) transcript termination, (f) transcript polyadenylation, (g) nuclear export of the transcript, (h) transcript editing, and (i) stabilizing the transcript.

Transcription factor for a gene means a cytoplasmic or nuclear protein which binds to (a) such gene, (b) an RNA transcript of such gene, or (c) a protein which binds to (i) such gene or such RNA transcript or (ii) a protein which binds to such gene or such RNA transcript, so as to thereby transcriptionally modulate expression of the gene.

Transcriptionally modulate the expression of a gene means to change the rate of transcription of such gene.

Triple helix means a helical structure resulting from the binding of one or more oligonucleotides to double stranded DNA.

The invention provides a method of directly and specifically transcriptionally modulating the expression of a gene encoding a protein of interest, the expression of which gene is associated with treatment of one or more symptoms of a cardiovascular disease in a human being. This method comprises contacting a cell, which is capable of expressing the gene, with a molecule at a concentration effective to transcriptionally modulate expression of the gene and thereby affect the level of the protein of interest encoded by the gene which is expressed by the cell. In this method the molecule (a) does not naturally occur in the cell, (b) specifically transcriptionally modulates expression of the gene encoding the protein of interest, and (c) directy binds to DNA or RNA, or directly binds to a protein at a site on such protein which is not a ligand-binding domain of a receptor which naturally occurs in the cell, the binding of a ligand to which ligand-binding domain is normally associated with a defined physiological or pathological effect.

Preferably, the cell contacted in accordance with the method identified above is a human cell.

This invention further provides a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a DNA sequence encoding a polypeptide other than the protein of interest, which polypeptide being capable of producing a detectable signal. The DNA sequence is coupled to, and under the control of, the promoter, under conditions such that the molecule, if capable of acting as a transcriptional modulator of the gene encoding the protein of interest, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the molecule as one which causes a change in the detectable signal produced by the polypeptide so expressed, and thus identifying the molecule as a molecule capable of directly and specifically transcriptionally modulating the expression of the gene encoding the protein of interest.

In the practice of the preceding method the polypeptide may be a luciferase, chloramphenicol acetyltransferase, $\beta$-glucuronidase, $\beta$-galactosidase, neomycin phosphotransferase, alkaline phosphatase or guanine xanthine phosphoribosyltransferase.

This invention still further provides a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a reporter gene, which expresses a polypeptide. The reporter gene is coupled to, and under the control of, the promoter, under conditions such that the molecule, if capable of acting as a transcriptional modulator of the gene encoding the protein of interest, causes a measurable detectable signal to be produced by the polypeptide so expressed. This allows for quantitative determination of the amount of the signal produced. By comparing the amount so determined with the amount of produced signal detected in the absence of any molecule being tested or upon contacting the sample with any other molecule, this method allows one to identify the molecule as one which causes a change in the detectable signal produced by the polypeptide so expressed, and thus identifying the molecule as a molecule capable of directly and specifically transcriptionally modulating the expression of the gene encoding the protein of interest.

In the foregoing methods the DNA sequence encoding the polypeptide may be inserted downstream of the promoter of the gene encoding the protein of interest by homologous recombination.

In certain embodiments of the invention the polypeptide so produced is capable of complexing with an antibody or is capable of complexing with biotin. In this case the resulting complexes may be detected.

This invention still further encompasses a method of determining whether a molecule not previously known to be a modulator of protein biosynthesis is capable of directly and specifically transcriptionally modulating the expression of a gene encoding a protein of interest associated with treatment of one or more symptoms of a cardiovascular disease. This method comprises contacting a sample which contains a predefined number of cells with a predetermined amount of a molecule to be tested. Each such cell comprises DNA consisting essentially of (i) a modulatable transcriptional regulatory sequence of the gene encoding the protein of interest, (ii) a promoter of the gene encoding the protein of interest, and (iii) a DNA sequence transcribable into mRNA coupled to and under the control of, the promoter. The contacting is under conditions such that the molecule, if capable of acting as a transcriptional modulator of the protein of interest, causes a measurable difference in the amount of mRNA transcribed from the DNA sequence. This method allows for the quantitative determination of the amount of the mRNA produced. By comparing the amount so determined with the amount of mRNA detected in the absence of any molecule being tested or upon contacting the sample with any other molecule, one can thereby identify the molecule as one which causes a change in the detectable mRNA amount of, and thus identifying the molecule as a molecule capable of directly and specifically transcriptionally modulating the expression of the gene encoding the protein of interest.

In a presently preferred embodiment of the mRNA is detected by quantitative polymerase chain reaction.

In each of the preceding methods the sample comprises cells in monolayers or cells in suspension. Preferably, such cells are animal cells, or human cells. In the presently preferred method the predefined number of cells is from about 1 to about $5 \times 10^5$ cells, or about $2 \times 10^2$ to about $5 \times 10^4$ cells. In these methods the predetermined amount or concentration of the molecule to be tested is typically based upon the volume of the sample, or be from about 1.0 pM to about 20 $\mu$M, or from about 10 nM to about 500 $\mu$M.

Typically the contacting is effected from about 1 to about 24 hours, preferably from about 2 to about 12 hours. Also the contacting is typically effected with more than one predetermined amount of the molecule to be tested. The molecule to be tested in these methods can be a purified molecule or a homogenous sample. Further, in the method of the invention and may consist essentially of more than one modulatable transcriptional regulatory sequence.

A screening method according to any of the methods discussed above is also claimed. This screening method comprises separately contacting each of a plurality of substantially identical samples, each sample containing a predefined number of cells under conditions such that contacting is affected with a predetermined amount of each different molecule to be tested.

In such a screening method the plurality of samples preferably comprises more that about $10^4$ samples, or more preferably comprises more than about $5 \times 10^4$ samples.

Also provided is a method of essentially simultaneously screening molecules to determine whether the molecules are capable of transcriptionally modulating one or more genes encoding proteins of interest according to the methods discussed above.

These methods are preferably carried out with more than about $10^3$ samples per week contacted with different molecules.

Pursuant to the provisions of the Budapest Treaty on the International Recognition of Deposit of Microorganisms For Purpose of Patent Procedure, the plasmid and the cell lines listed below have been deposited with the American Type Culture Collection ("ATCC"), 12301 Parklawn Drive, Rockville, Md. 20852, U.S.A.:

1. a plasmid designated pUV106, deposited under ATCC Accession No. 40946;
2. a human promylelocytic cell line HL60 transfected with pCSF1-102 and pTKNeo3, designated M2086, deposited under ATCC Accession No. CRL 10641;
3. a human bladder carcinoma cell line transfected with pGUV150, designated G1002, deposited under ATCC Accession No. CRL 10660;
4. a human bladder carcinoma cell line transfected with pGMLL103neo3, designated GM1073, deposited under ATCC Accession No. CRL 10664;
5. a NIH Swiss mouse embryo cell line, NIH 3T3, transfected with the MMTV reporter plasmid, designated M10, deposited under ATCC Accession No. CRL 10659; and
6. a GC rat pituitary cell line, transfected with the growth hormone reporter plasmid, designated 532, deposited under ATCC Accession No. CRL 10663.

A method for directly and specifically transcriptionally modulating in a multicellular organism the expression of a gene encoding a protein of interest, the expression of which is associated with treatment of one or more symptoms of a cardiovascular disease in a human being, is also provided. This method comprises administering to the human being a molecule at a concentration effective to transcriptionally modulate expression of the protein of interest and thus ameliorating the cardiovascular disease. In this method the molecule (a) does not naturally occur in a human being and (b) specifically transcriptionally modulates expression of the gene encoding the protein of interest, and (c) direcly binds to DNA or RNA, or directly binds to a protein at a site on such protein which is not a ligand-binding domain of a receptor which naturally occurs in the cell, the binding of a ligand to which ligand-binding domain is normally associated with a defined physiological or pathological effect.

In one embodiment of the methods above, the invention the molecule does not naturally occur in any cell of a lower eucaryotic organism such as yeast.

In the preferred embodiment, the molecule does not naturally occur in any cell, whether of a multicellular or a unicellular organism. In a presently more preferred embodiment, the molecule is not a naturally occurring molecule, e.g. it is a chemically synthesized entity.

In the methods above modulation of the transcription of the gene results in either upregulation or downregulation of expression of the gene encoding the protein of interest, depending on the identity of the molecule which contacts the cell.

In one embodiment of the inventions above the molecule binds to a modulatable transcription sequence of the gene. For example, the molecule may bind to a promoter region upstream of the coding sequence encoding the protein of interest.

In one embodiment of the methods of the invention above the molecule comprises an antisense nucleic acid which is complementary to a sequence present in a modulatable, transcriptional sequence. The molecule may also be a double-stranded nucleic acid or a nucleic acid capable of forming a triple helix with a double-stranded DNA.

In the methods described above the cardiovascular disease may be atherosclerosis or restenosis. The protein of interest may be involved in lipid transport or cellular uptake e.g. apolipoprotein (a, AI, AII, AIV, B, CI, CII, CIII or E), low density lipoprotein receptor (LDL-R), cholesterol ester transfer protein, hepatic TG lipase, lipoprotein lipase, high density lipoprotein receptor p110, LDL receptor like protein, ARP1, LDL-R protein kinase, apolipoprotein E receptor or oncostatin M. The protein of interest may be involved in the uptake of modified lipoproteins e.g. LDL-R, scavenger receptor, advanced glycosylated end-product receptor or macrophage FC receptor. The protein of interest may be involved in lipid metabolism e.g. AMP-activated protein kinase, AMP-activated protein kinase kinase, acetyl CoA cholesterol ester transferase, lecithin-cholesterol ester transferase, cholesterol 7α-hydroxylase, hormone sensitive-lipase/cholesterol ester hydroxylase or HMG CoA reductase. The protein of interest may be involved in lipid oxidation e.g. 15-lipoxygenase, IL-4, IL-4 receptor, superoxide dismutase or 12 lipoxygenase. The protein of interest may be involved in smooth muscle cell growth such as platelet derived growth factor (PDGF-A), PDGF-B, PDGF-α receptor, PDGF-β receptor, heparin-binding EGF-like growth factor, basic fibroblast growth factor (bFGF), aFGF, FGF receptor, IL-1, IL-1 receptor p80, IL-1 receptor protein kinase, interferon gamma, TGF-β1, TGF-β2, TGF-β3, TGF receptor, tumor necrosis factor-α (TNF-α), TNF-α receptor, α-thrombin, α-thrombin receptor, 9-hydroxyoctadeca-10, 12-dienoic acid (9-HODE) receptor, insulin-like growth factor, platelet factor-4, TGF-α, thromboxane $A_2$ receptor, 12-hydroxy-5,8,10,14-eicosatetraenoic acid (12-HETE) receptor, 13-hydoxyoctadeca-9,11-dienoic acid (13-HODE) receptor, IL-6, IL-6 receptor or EGF receptor. The protein of interest may be an endothelial cell growth factor or receptor (EGF) such as vascular EGF, VEGF receptor, bFGF, aFGF, FGF receptor or platelet-derived endothelial cell growth factor. The protein of interest may be associated with macrophage growth and chemotaxis e.g. CSF-1, CSF-1 receptor, monocyte chemoattractant protein-1 (MCP-1) or MCP-1 receptor. Lastly the protein of interest associated with atherosclerosis may be associated with endothelial cell adhesion such as VCAM-1, VLA-4 $α_4$ subunit, VLA-4 $β_1$ subunit, ELAM-1, ICAM-1, LFA-1 $α_L$ subunit, LFA-1 $β_2$ subunit, GMP-140 (PADGEM), neuropeptide Y, VLA-4 $α_1$ subunit, vitronectin receptor or 13-hydoxyoctadeca-9,11-dienoic acid (13-HODE) receptor. The protein of interest associated with the treament of cardiovascular disease or atherosclerosis may be PEPCK.

In the methods described above the cardiovascular disease may be associated with thrombosis. In these cases the protein of interest may be one of the following: fibrinogen, fibrinogen receptor subunit IIb, fibrinogen receptor subunit IIIa, fibrinogen receptor subunit $β_3$, fibrinogen receptor subunit $α_v$, von Willebrand factor (vWF), vWF receptor subunit Ibβ, vWF receptor subunit Ibα, vWF receptor subunit GPIX, plasminogen activator-1, platelet activating factor receptor, plasminogen, tissue plasminogen activator t-PA, u-PA, factor V, factor VII, factor VIII, factor IX, factor X, factor XI, factor XII, protein C, protein S, thrombomodulin, tissue factor, thrombospondin, CD36, kininogen, an eicosanoid receptor or an eicosanoid biosynthetic enzyme.

In addition the cardiovascular disease in the methods above may be hypertension. The protein of interest associated with hypertension includes: angiotensin, preprorenin, renin, angiotensin converting enzyme (ACE), atrial natriuretic peptide (ANP), brain natriuretic peptide, C natriuretic peptide, natriuretic peptide receptor-A, natriuretic peptide receptor-B, natriuretic peptide receptor-C, EDRF, nitric oxide synthase I ($Ca^{+2}$/calmodulin dependent), nitric oxide synthase II (inducible), nitric oxide-dependent guanylate cyclase α-subunit, nitric oxide-dependent guanylate cyclase β-subunit, α-adrenoceptors, endothelins, endothelin receptors, vasopressin, vasopressin receptor, serotonin (5-HT) receptors, adenosine receptors, $P_2$-purinoceptors, calcitonin gene-related peptide (CGRP), CGRP receptor, substance P, substance K, neurokinin B, tachykinin receptor, angiotensin II receptor $AT_1$, kininogen, tissue kallikrein, plasma kallikrein, an acetylcholine receptor, a voltage dependent calcium channel, an eicosanoid receptor, an eicosanoid biosynthetic enzyme, a β-adrenoceptor, $Na^+$, $K^+$— ATPase, vasoactive intestinal peptide, a histamine receptor, an aldosterone receptor or heart angiotensinogen kinase.

Additional cardiovascular diseases or diseases associated with the symptoms of cardiovascular diseases include congestive heart failure, angina, ischemic heart disease, diabetes mellitus, non-insulin-dependent diabetes, thrombophlebitis, stroke hypercholesteremia, familial hypercholesteremia, combined familial hypercholesteremia, hyperglycemia or diseases associated with calcium regulation or metabolism.

The administering discussed in the preceding methods may comprise topical contact or oral, transdermal, intravenous, intramuscular or subcutaneous administration. Methods of administration of molecules in the practice of the invention are well known to those skilled in the art as are methods of formulating the molecule for administration depending on the specific route of administration being employed.

This invention is illustrated in the Experimental Detail section which follow. These sections are set forth to aid in an understanding of the invention but are not intended to, and should not be construed to, limit in any way the invention as set forth in the claims which follow thereafter.

EXPERIMENTAL DETAILS

1. Cell Culture

All media and reagents used for routine cell culture were purchased from Gibco (Grand Island, N.Y.), Hazelton (Lenexa, Kans.), or Whittaker M. A. Biologicals (Walkersville, Md.). Fetal calf serum (FCS) was from Hyclone (Logan, Utah).

A murine embryonic fibroblast cell line, NIH3T3 (ATCC# CCL92), was used for the transfection of plasmids carrying the MMTV promoter (a control cell line). These cells were maintained on DMEM, supplemented with 10% FCS.

A human hepatocarcinoma cell line HepG2 (ATCC# HB 8065), is used for the transfection of plasmids carrying the promoter and regulatory elements of the genes for apolipoprotein (a), apolipoprotein AI, apolipoprotein B, LDL receptor, cholesterol 7α-hydroxylase and fibrinogen β-subunit. These cells are maintained in DMEM/MEM, 50:50, supplemented with 10% FCS.

Human monoblast U937 cells (ATCC# CRL 1593) are used for the transfection of plasmids carrying the promoter and regulatory elements of the gene for vascular endothelial growth factor (VEGF). These cells are maintained in DMEM/MEM/HAMS F12 supplemented with 10% FCS.

Human epidermoid carcinoma A431 cells (ATCC# CRL 1555) are used for the transfection of plasmids carrying the promoter and regulatory elements of the gene for VEGF. These cells are maintained in DMEM, supplemented with 10% FCS.

Human promyelocytic leukemia HL60 cells (ATCC# CCL 240) are used for the transfection of plasmids carrying the promoter and regulatory elements of the genes for VEGF and colony stimulating factor-1 (CSF-1). These cells are maintained in RPMI 1640 medium supplemented with 20% FCS.

Human monocytic THP-1 cells (ATCC# TIB 202) are used for the transfection of plasmids carrying the promoter and regulatory elements of the gene for the scavenger receptor. These cells are maintained in RPMI 1640 supplemented with 10% FCS.

Human fibroblastic WI38 cells (ATCC# CCL 75) are used for the transfection of plasmids carrying the promoter and regulatory elements of the genes for CSF-1 and monocyte chemoattractant protein-1 (MCP-1). These cells are maintained in DMEM supplemented with 10% FCS.

A human cervical carcinoma cell line HeLa S3 (ATCC# CCL 2.2), is used for the transfection of plasmids carrying the promoter and regulatory elements of the genes for apolipoprotein (a), apolipoprotein AI, apolipoprotein B and fibrinogen β-subunit. These cells are maintained in DMEM supplemented with 10% FCS 2. Construction of Luci Reporter Vector Unless otherwise indicated, molecular cloning procedures were performed essentially according to Maniatis et al. (77). Oligonucleotides were synthesized by the beta-cyanoethyl phosphoramidite method according to protocols provided by the manufacturer of the DNA-synthesizer (Model 380A, Applied Biosystems (Foster City, Calif.).

A mammalian expression shuttle vector was designed to allow the construction of the promoter-reporter gene fusions to be used in high-throughput screens to identify transcriptionally modulating chemicals. Features of the plasmid are shown in FIG. 1. The shuttle vector was constructed in several steps.

Figure 2:
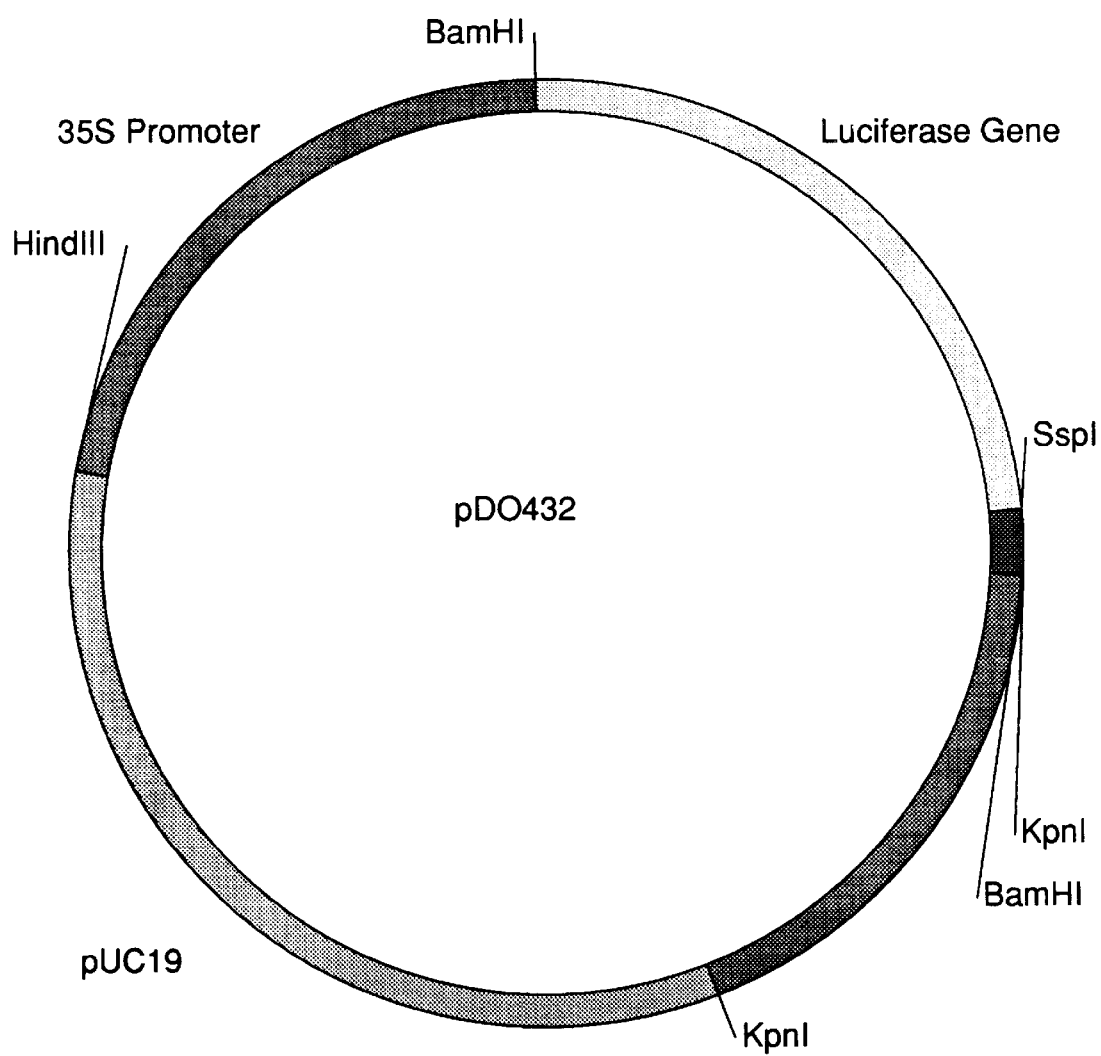
FIG. 2 is a partial restriction enzyme cleavage map of the plasmid pD0432 which contains the luciferase gene from the firefly, *Photinus pyralis*.
Figure 3:
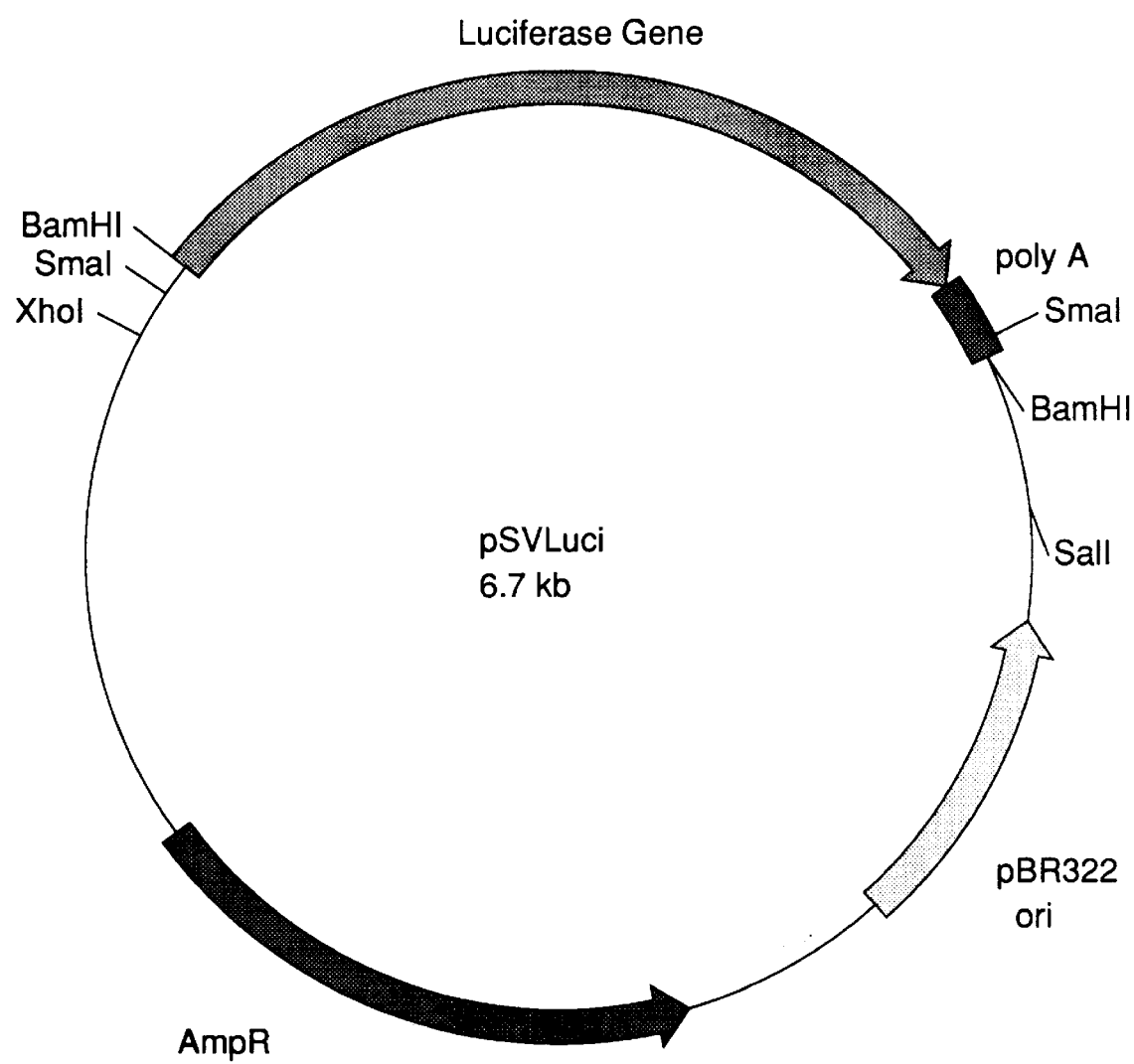
FIG. 3 is a partial restriction enzyme cleavage map of the plasmid pSVLuci which contains the luciferase gene from the firefly, *Photinus pyralis*.
Figure 4:
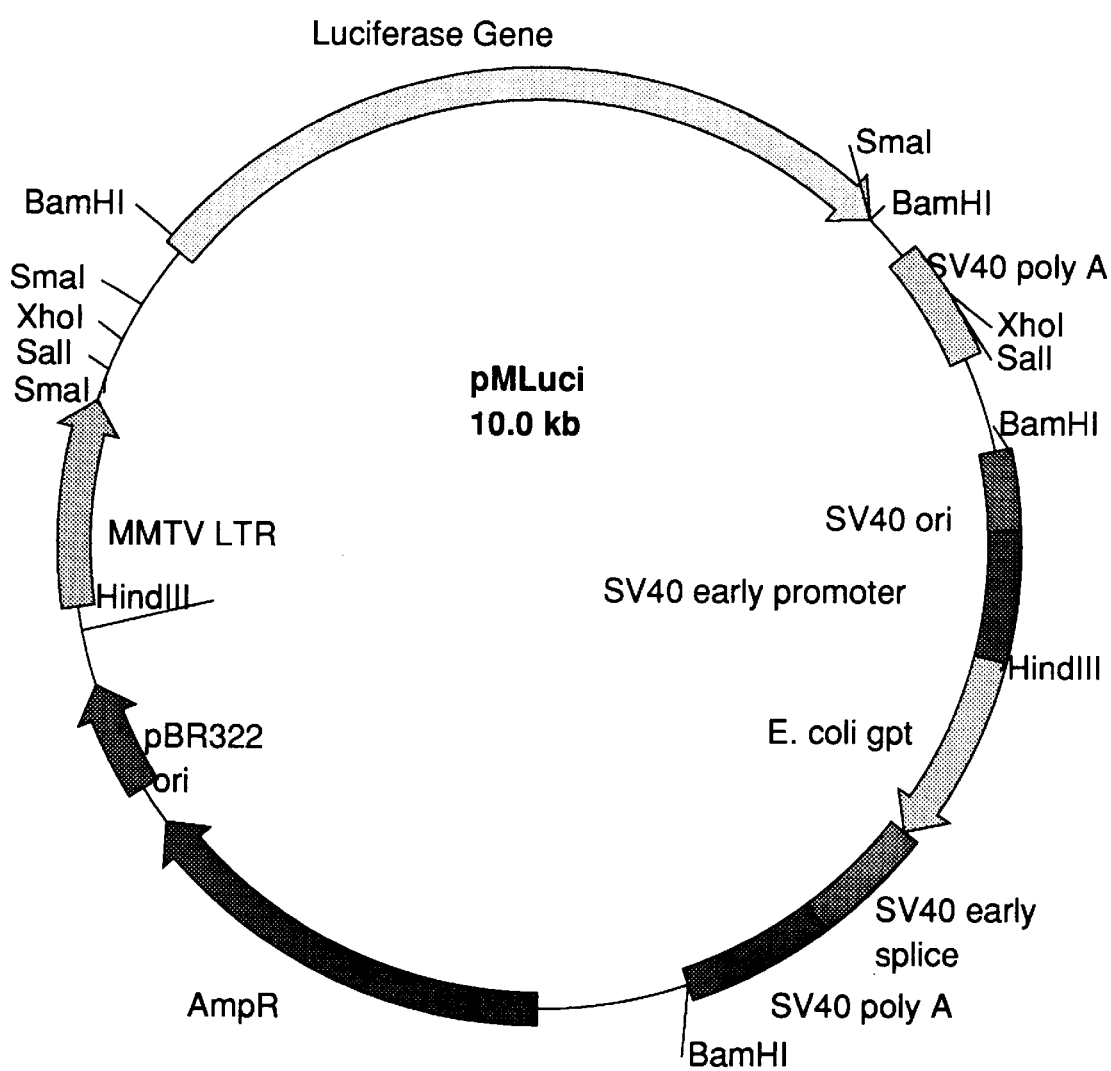
FIG. 4 is a partial restriction enzyme cleavage map of the plasmid pMLuci which contains the luciferase gene of the firefly, *Photinus pyralis* and the mouse mammary tumor virus long terminal repeat.

The firefly luciferase gene was removed from the plant expression plasmid pDo432 (78) (FIG. 2) as a 1.9 kb BamHI fragment and cloned into the BamHI site of pSVL (Pharmacia, Piscataway, N.J.), a mammalian expression vector containing the SV40 promoter. The resulting plasmid (pSVLuci; FIG. 3) was digested with XhoI and SalI to produce a 2.4 kb fragment containing the luciferase coding sequences and the SV40 late polyadenylation site. This fragment was inserted into the XhoI site of pMSG (Pharmacia, Piscataway, N.J.), a eucaryotic expression vector containing the MMTV promoter. The resulting MMTV promoter-luciferase fusion plasmid (pMLuci; FIG. 4) was used to transfect NIH/3T3 cells as described below. Similar constructs can be made using luciferase vectors from Clontech (Palo Alto, Calif.).

Figure 6:
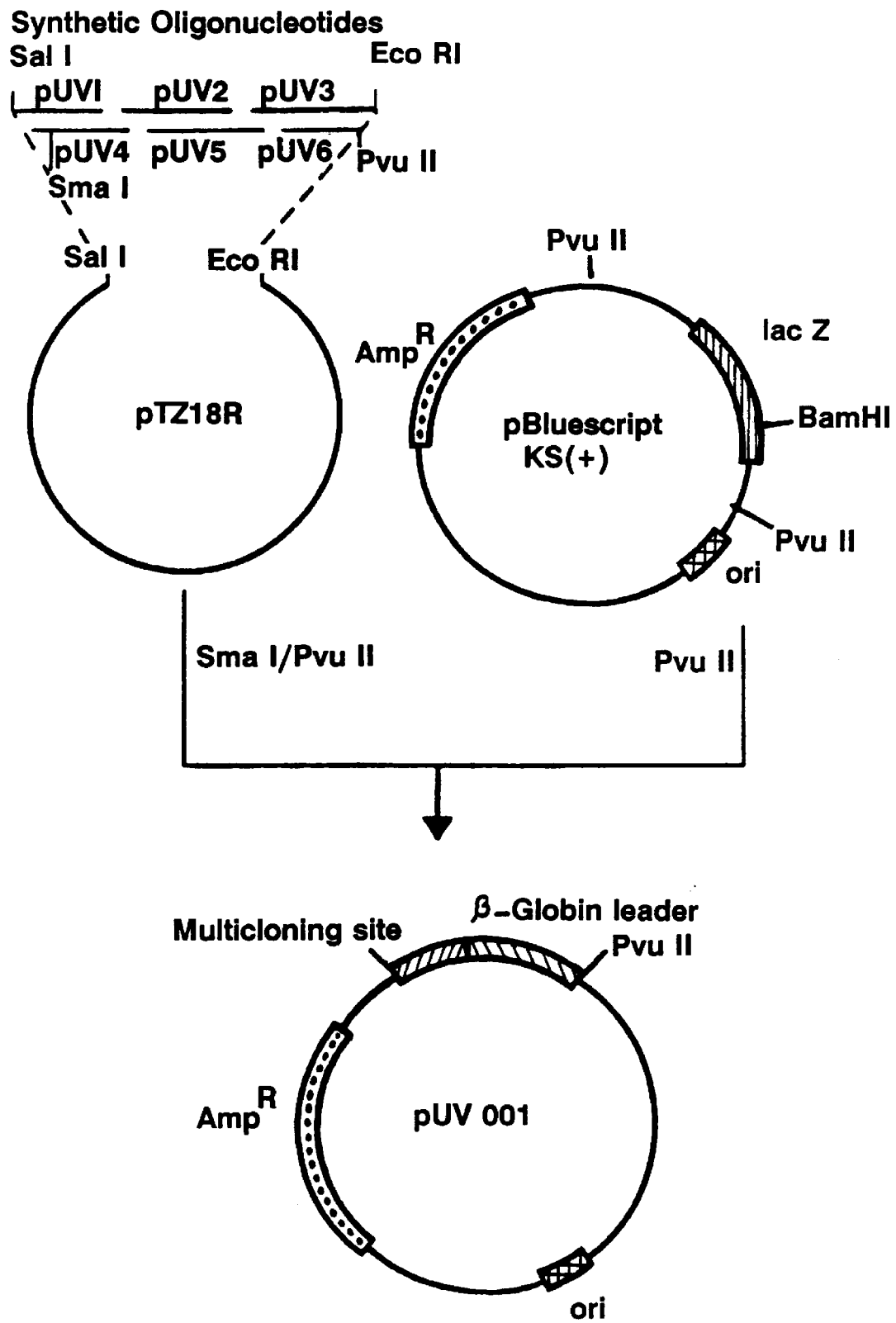
FIG. 6 is a diagrammatic representation of the construction of the plasmid pUV001 from the plasmids pTZ18R and pBluescript KS(+).
Figure 7:
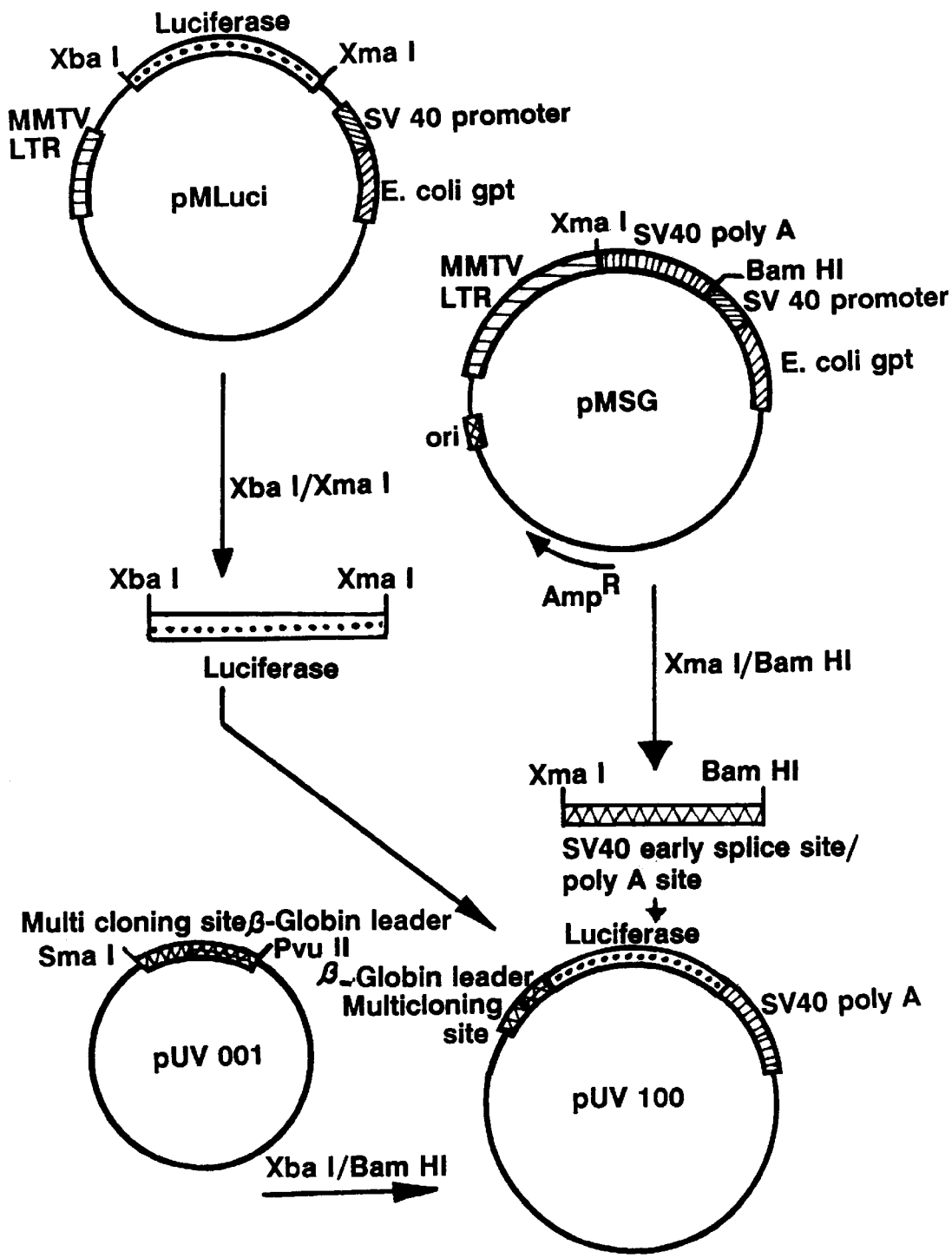
FIG. 7 is a diagrammatic representation of the construction of the plasmid pUV100 from the plasmid pUV001 and two DNA fragments, the XbaI/XmaI fragment from pMLuci and the XmaI/BamHI fragment from pMSG.

Six oligonucleotides (pUV-1 through pUV-6) (SEQ ID NO: 1–6) were synthesized (see FIG. 5 for sequence). The sequences of pUV-1, pUV-2 and pUV-3 correspond to a multicloning site, the beta-globin leader sequence and the first 53 bases of the firefly luciferase coding region. The sequences of pUV-4, pUV-5 and pUV-6 are complementary to the first three oligonucleotides. The pUV oligonucleotides were annealed, ligated and inserted into the SalI/EcoRI sites of pTZ18R (Pharmacia, Piscataway N.J.) (FIG. 6). The resulting vector was then digested with SmaI/PvuII and the oligonucleotide containing fragment was cloned into the pBluescriptKS(+) plasmid (Stratagene, La Jolla, Calif.), previously digested with PvuII, to yield pUV001 (FIG. 6). Several fragments were ligated into pUV001 to create pUV100. The luciferase coding sequences (except first 53 bases) and polyadenylation site were obtained as a 1.8 kilobase XbaI/XmaI fragment from pMLuci (section B-1, FIG. 4). The SV40 early splice site and the SV40 late polyadenylation site were obtained as an 871 bp XmaI/BamHI fragment from pMSG (Pharmacia, Piscataway N.J., FIG. 7). Both DNA fragments were cloned into pUV001, previously digested with XbaI/BamHI to yield pUV100 (FIG. 7).

Figure 8:
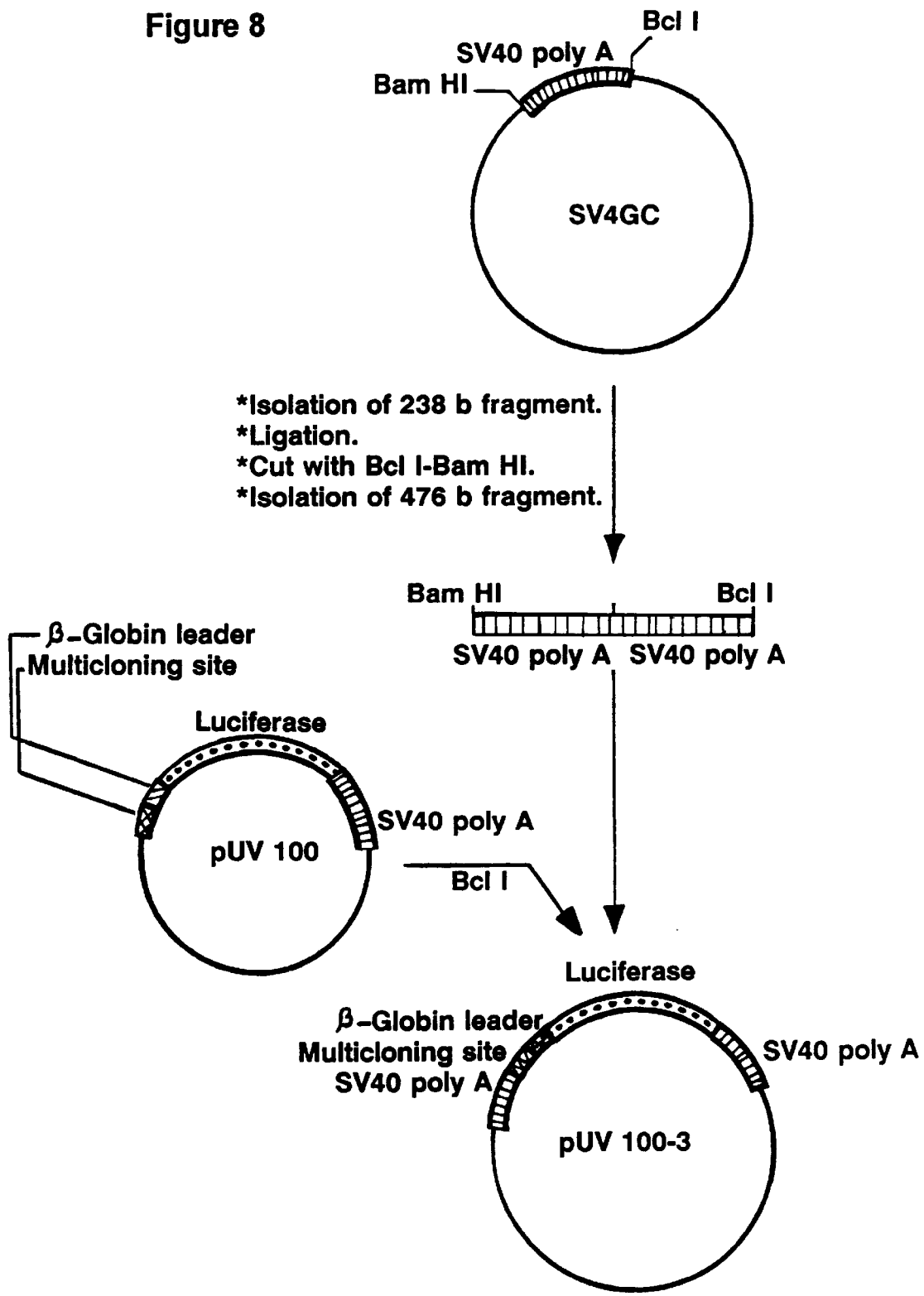
FIG. 8 is a diagrammatic representation of the construction of the plasmid pUV100-3 from the plasmid pUV100 and a 476 b fragment containing a dimeric SV40 polyadenylation site.

A 476 b fragment containing a dimeric SV40 polyadenylation site was then cloned into the BclI site of pUV100 (FIG. 8). To do this, a 238 bp BclI/BamHI fragment was obtained from SV40 genomic DNA (BRL), ligated, digested with BclI/BamHI, gel isolated, and inserted into pUV100, resulting in the vector pUV100–3 (FIG. 8). Linkers containing one SfiI and one NotI restriction site were then cloned into the PvuII/BamHI sites of pUV100-3. Two sets of linkers were synthesized containing the SfiI site in opposite orientations (oligonucleotides D-link1 and D-link2 and oligonucleotides R-link1 and R-link2). The sequences of the oligonucleotides (SEQ ID NO: 7–10) were:

5' GATCGGCCCCTAGGGCCGCGGCCGCAT 3'   (D-link1)

5' ATGCGGCCGCGGCCCTAGGGGCC 3'   (D-link2)

5' GATCGGCCCTAGGGGCGGCCGCAT 3'   (R-link1)

5' ATGCGGCCGCGGCCCCCTAGGGCC 3'   (R-link2)

Figure 9:
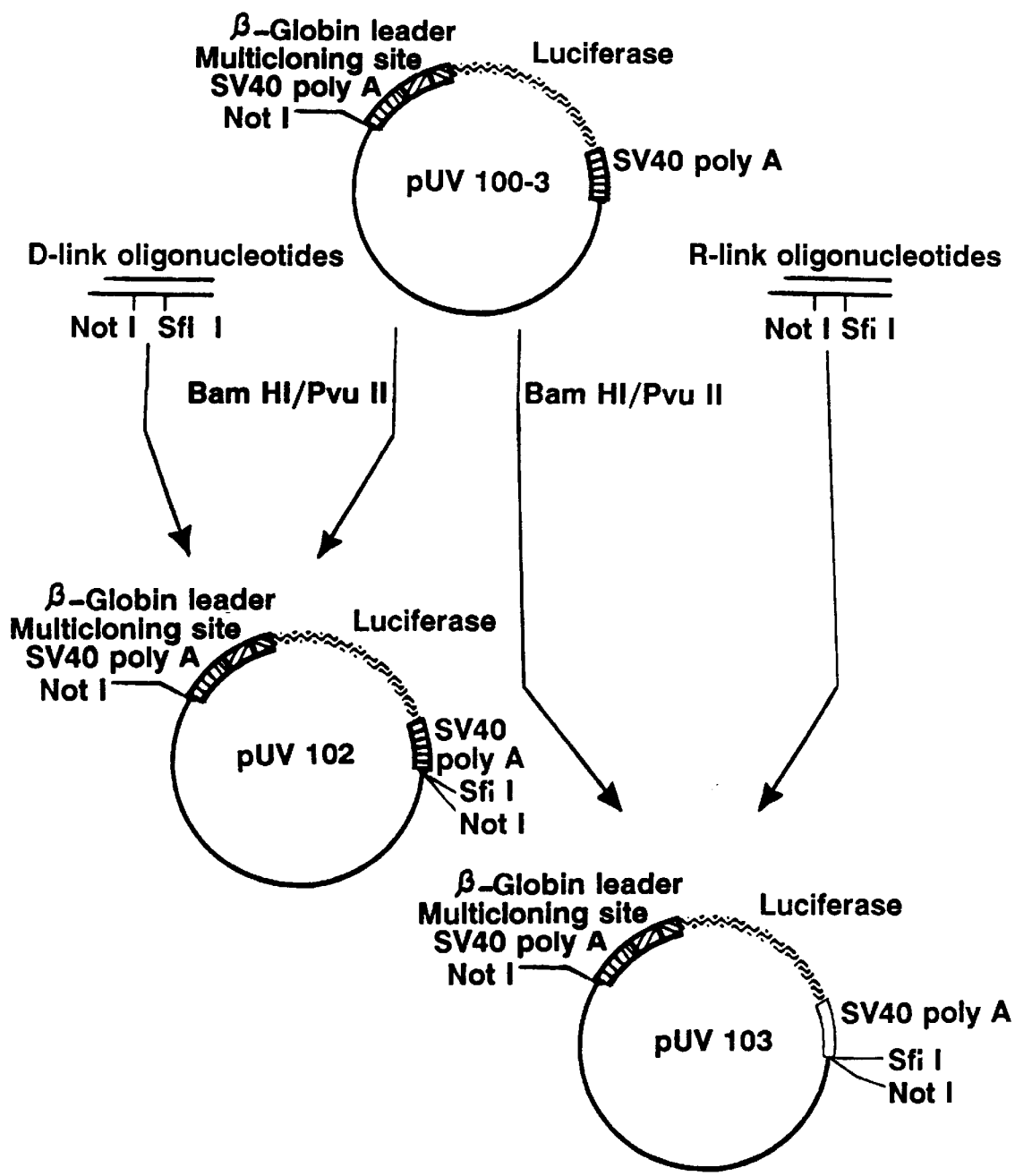
FIG. 9 is a diagrammatic representation of the construction of the plasmids pUV102 and pUV103 from the plasmid pUV100-3 and D-link oligonucleotides and the plasmid pUV100-3 and R-link oligonucleotides, respectively.

The plasmid that contains D-link oligonucleotides was named pUV102 and the plasmid that contains R-link oligonucleotides was named pUV103 (FIG. 9).

Figure 11:
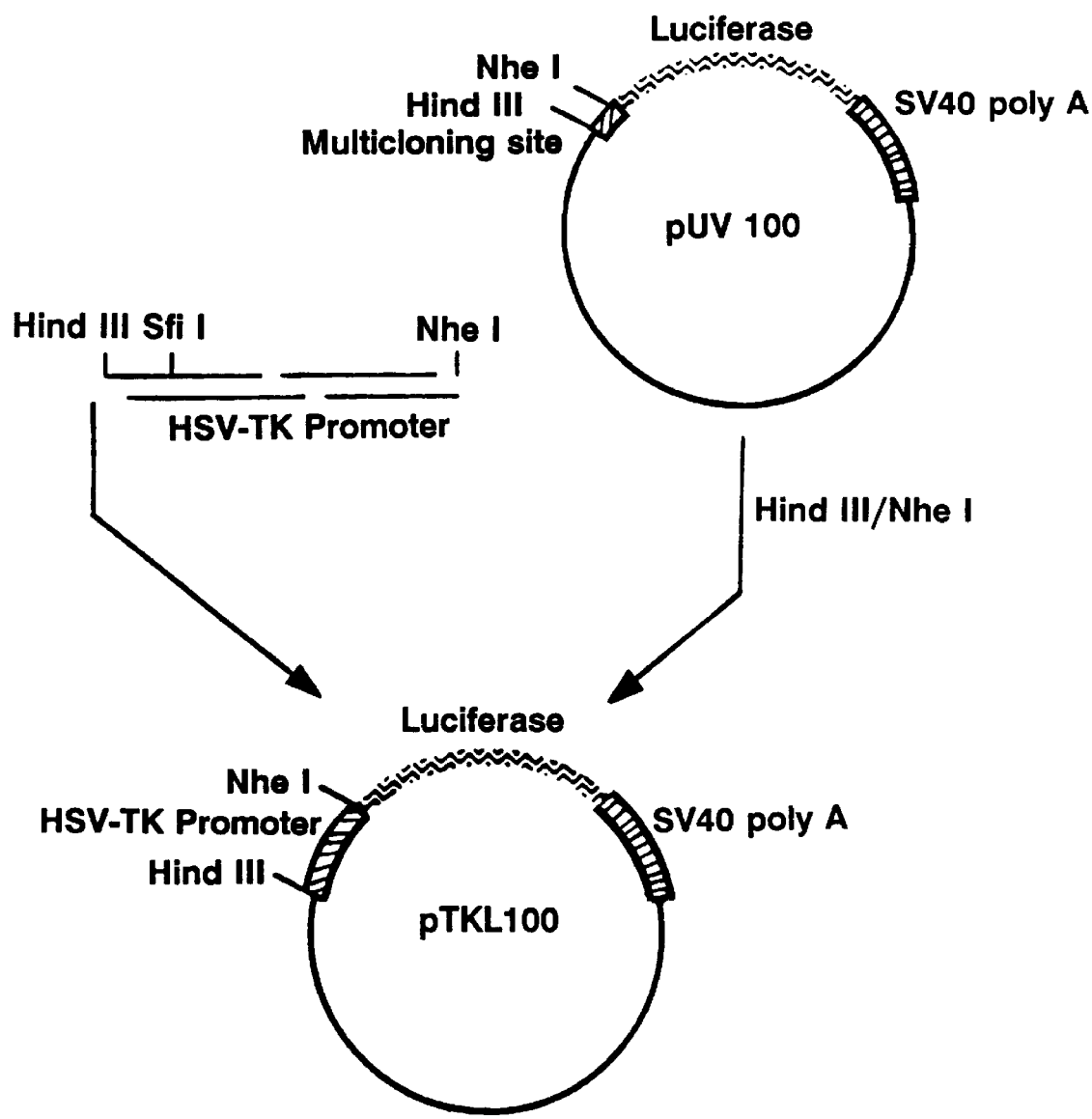
FIG. 11 is a diagrammatic representation of the construction of the plasmid pTKL100 which contains the luciferase gene from the firefly, *Photinus pyralis* and the HSV-TK promoter sequence.
Figure 12:
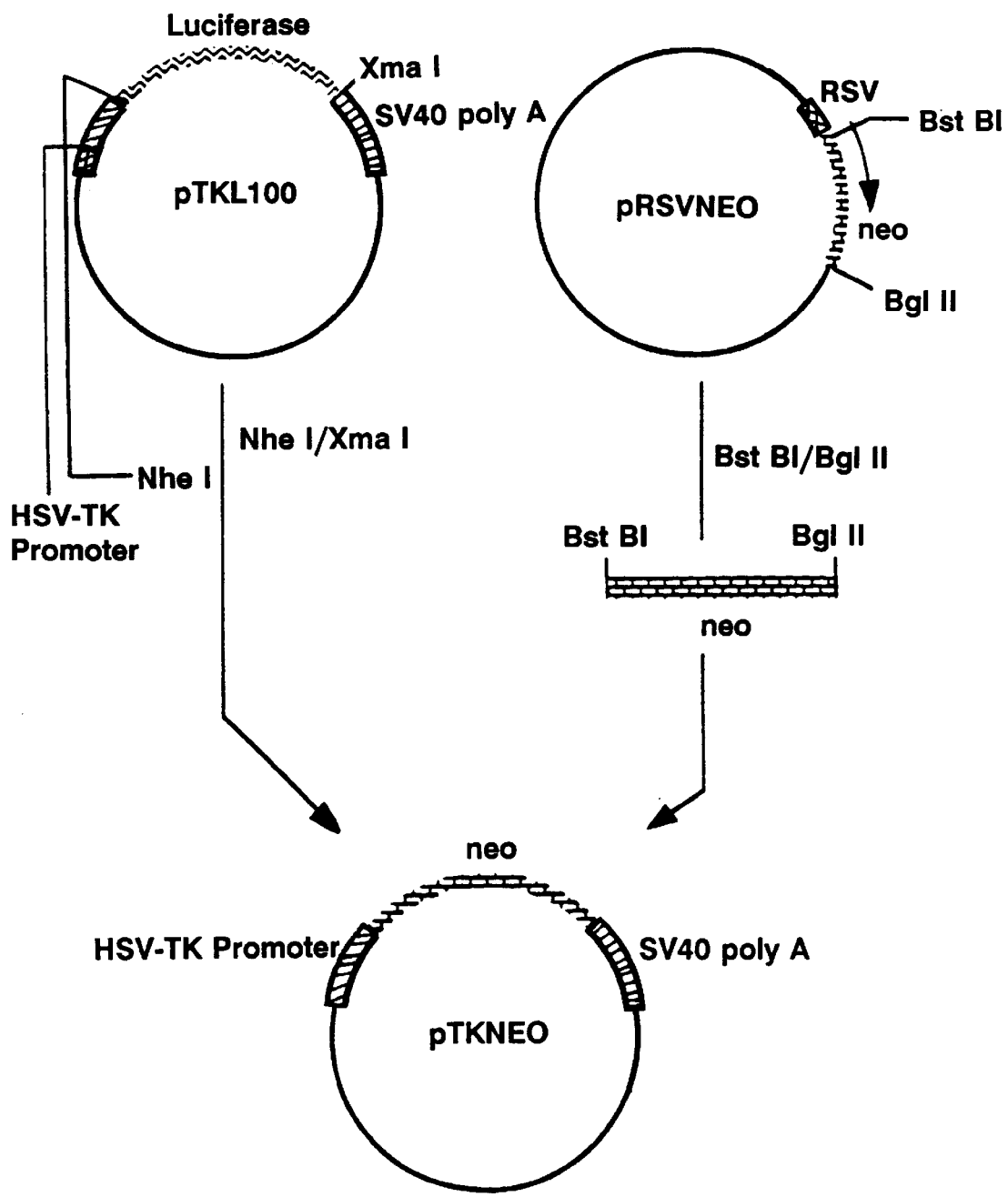
FIG. 12 is a diagrammatic representation of the construction of the plasmid pTKNEO which contains the neo gene, from about 3.5 kb NheI/XmaI fragment from pTKL100, and the about 0.9 kb BstBI/BglII fragment containing the neo coding region from pRSVNEO.
Figure 13:
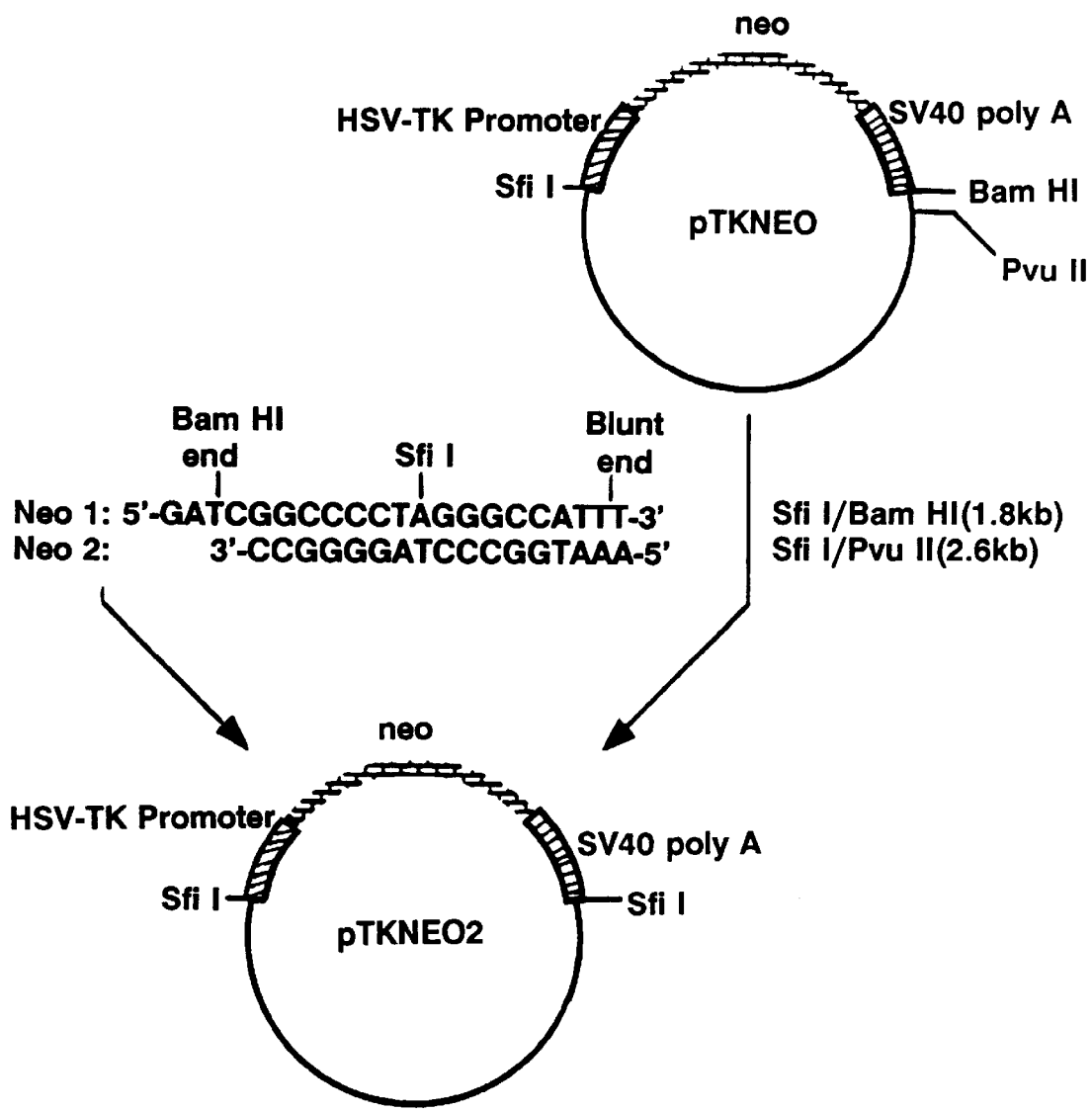
FIG. 13 is a diagrammatic representation of the construction of the plasmid pTKNEO2 from the plasmid pTKNEO and the oligonucleotides Neo 1 and 2.
Figure 14:
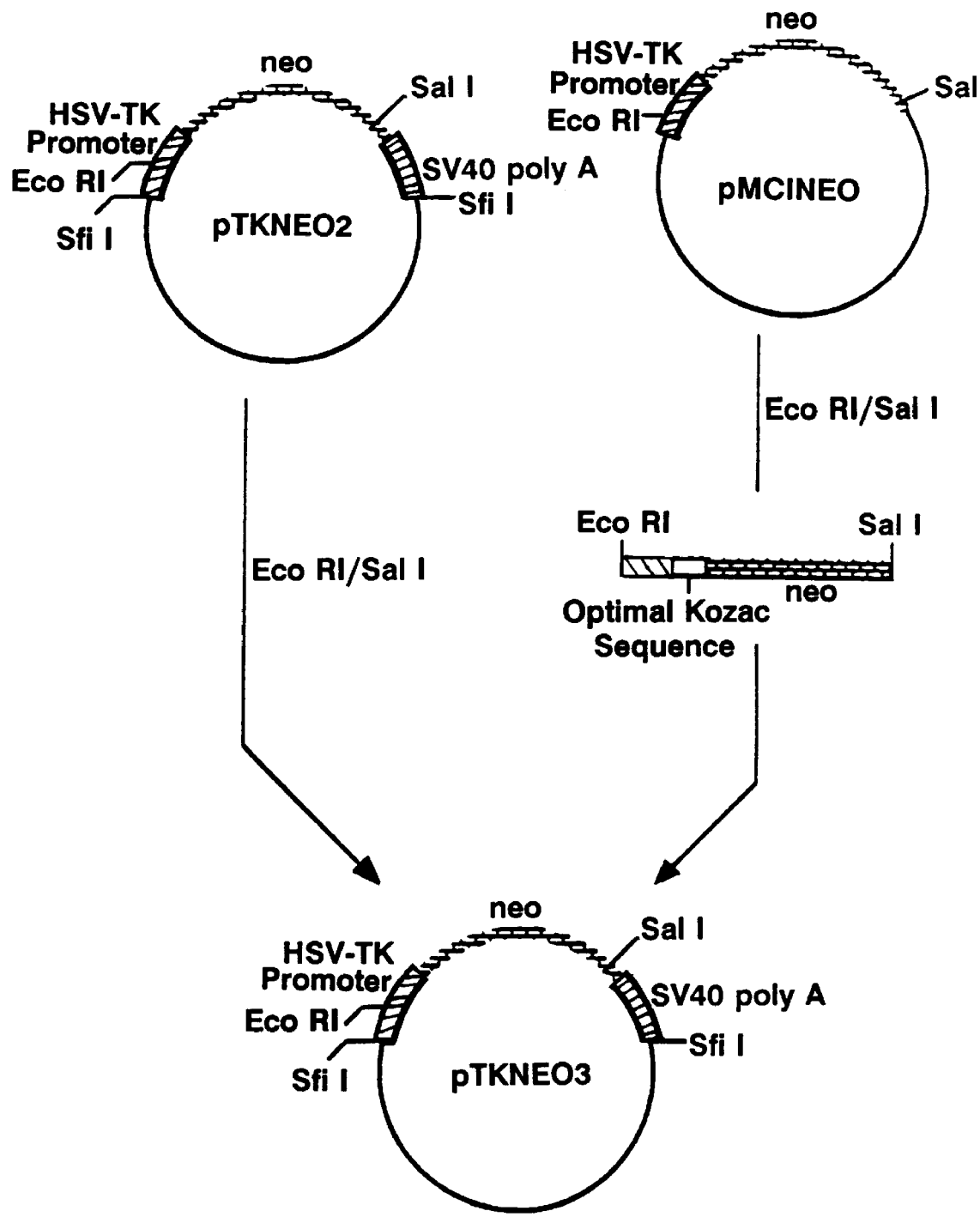
FIG. 14 is a diagrammatic representation of the construction of the plasmid pTKNEO3 from the plasmid PTKNEO2 and about 0.9 kb EcoRI/SalI fragment from pMC1NEO.
Figure 15:
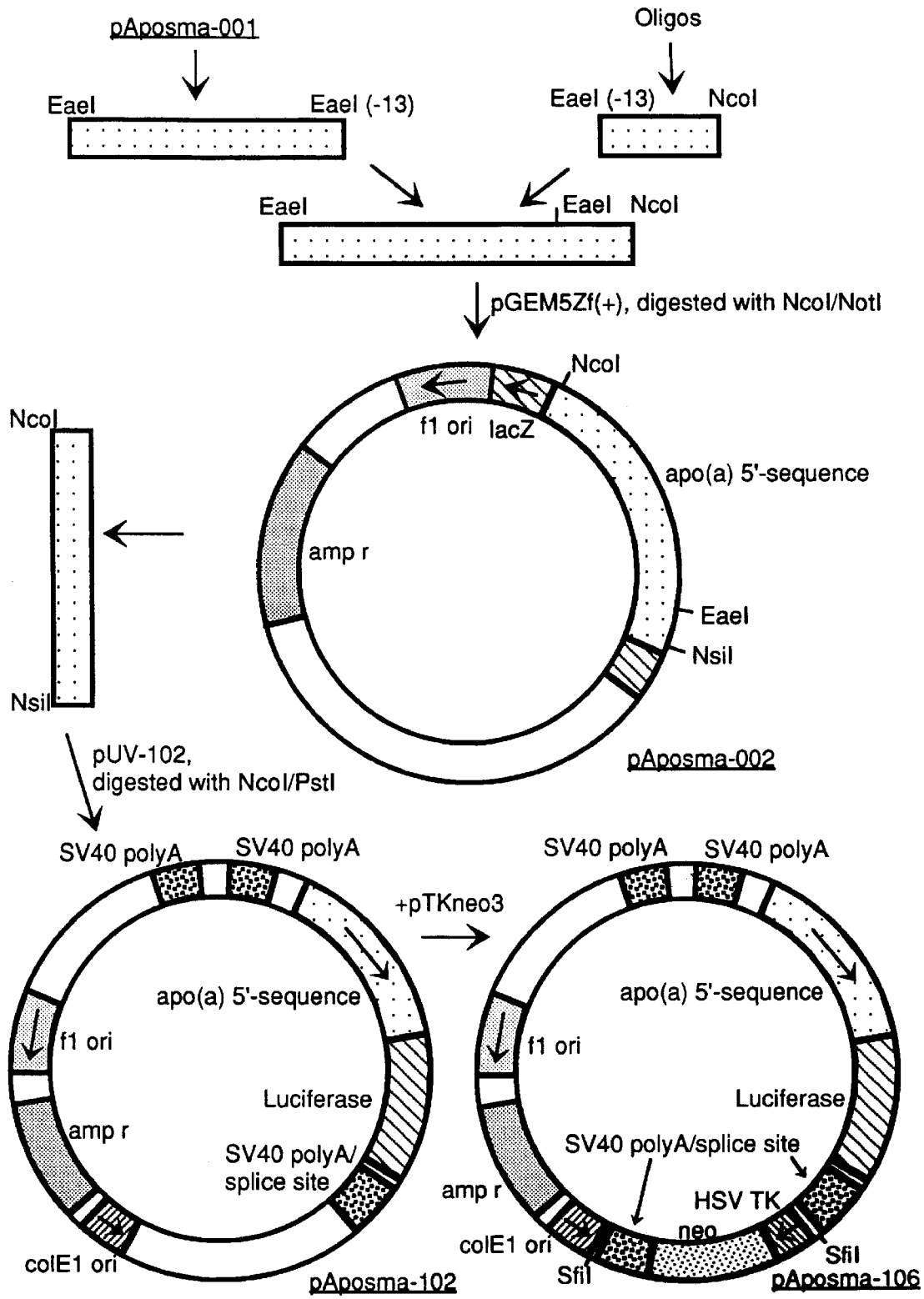
FIG. 15 shows the molecular cloning method for insertion of the regulatory and promoter elements of the apolipoprotein (a) gene into the mammalian expression shuttle vector. Details of the cloning method, including sequence information for oligonucleotide, are given in section C, part 1. Numbers (–13) in parentheses refer to a restriction site 13 base pairs upstream of the apolipoprotein (a) gene translational initiation codon.*
Figure 16:
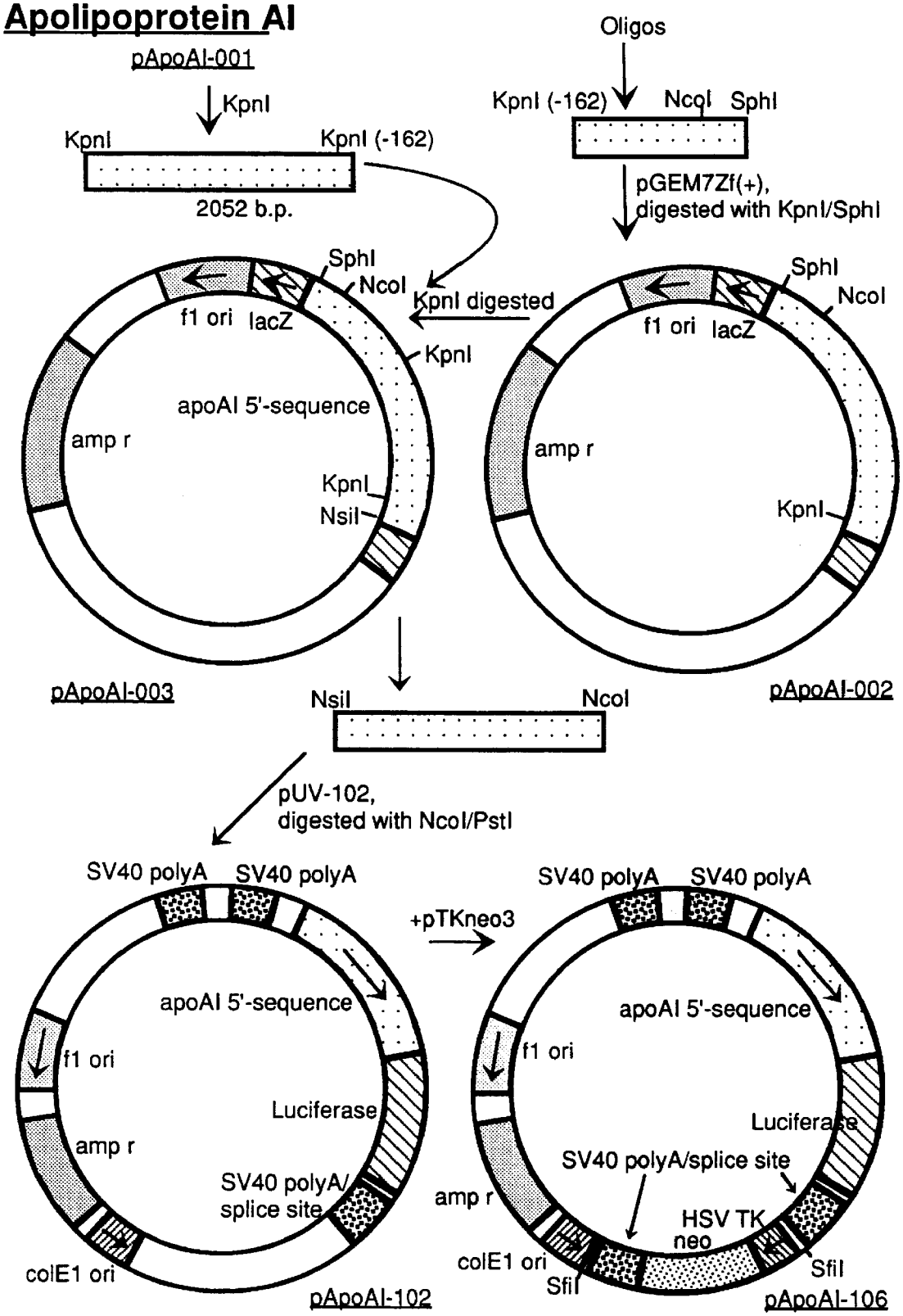
FIG. 16 shows the molecular cloning method for insertion of the regulatory and promoter elements of the apolipoprotein Al gene into the mammalian expression shuttle vector. Details of the cloning method, including sequence information for oligonucleotide, are given in section C, part 2. Numbers (–162) in parentheses refer to a restriction site 162 base pairs upstream of the apolipoprotein Al gene translational initiation codon.*
Figure 17:
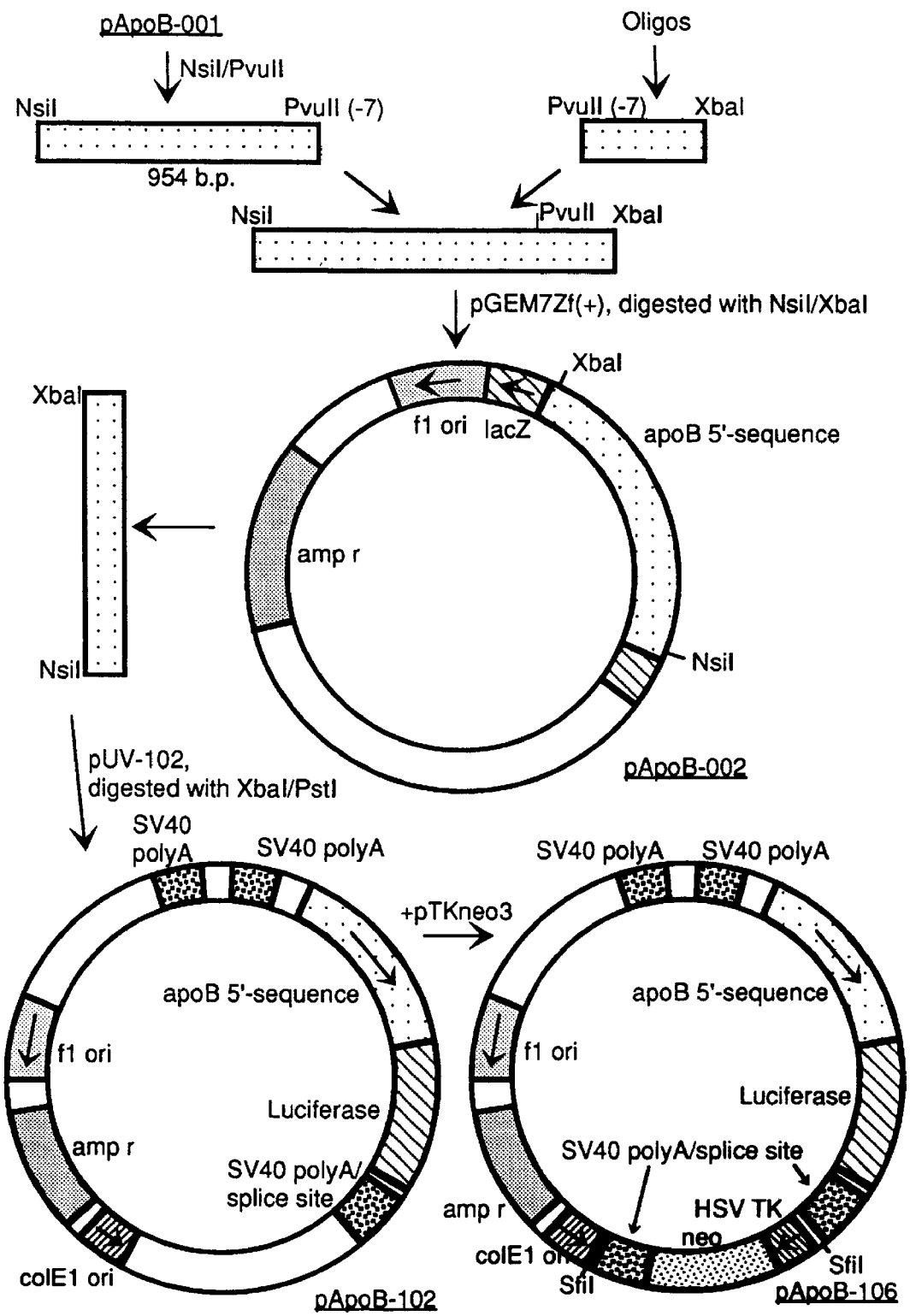
FIG. 17 shows the molecular cloning method for insertion of the regulatory and promoter elements of the apolipoprotein B gene into the mammalian expression shuttle vector. Details of the cloning method, including sequence information for oligonucleotide, are given in section C, part 3. Numbers (–7) in parentheses refer to a restriction site 7 base pairs upstream of the apolipoprotein B gene translational initiation codon.*
Figure 18:
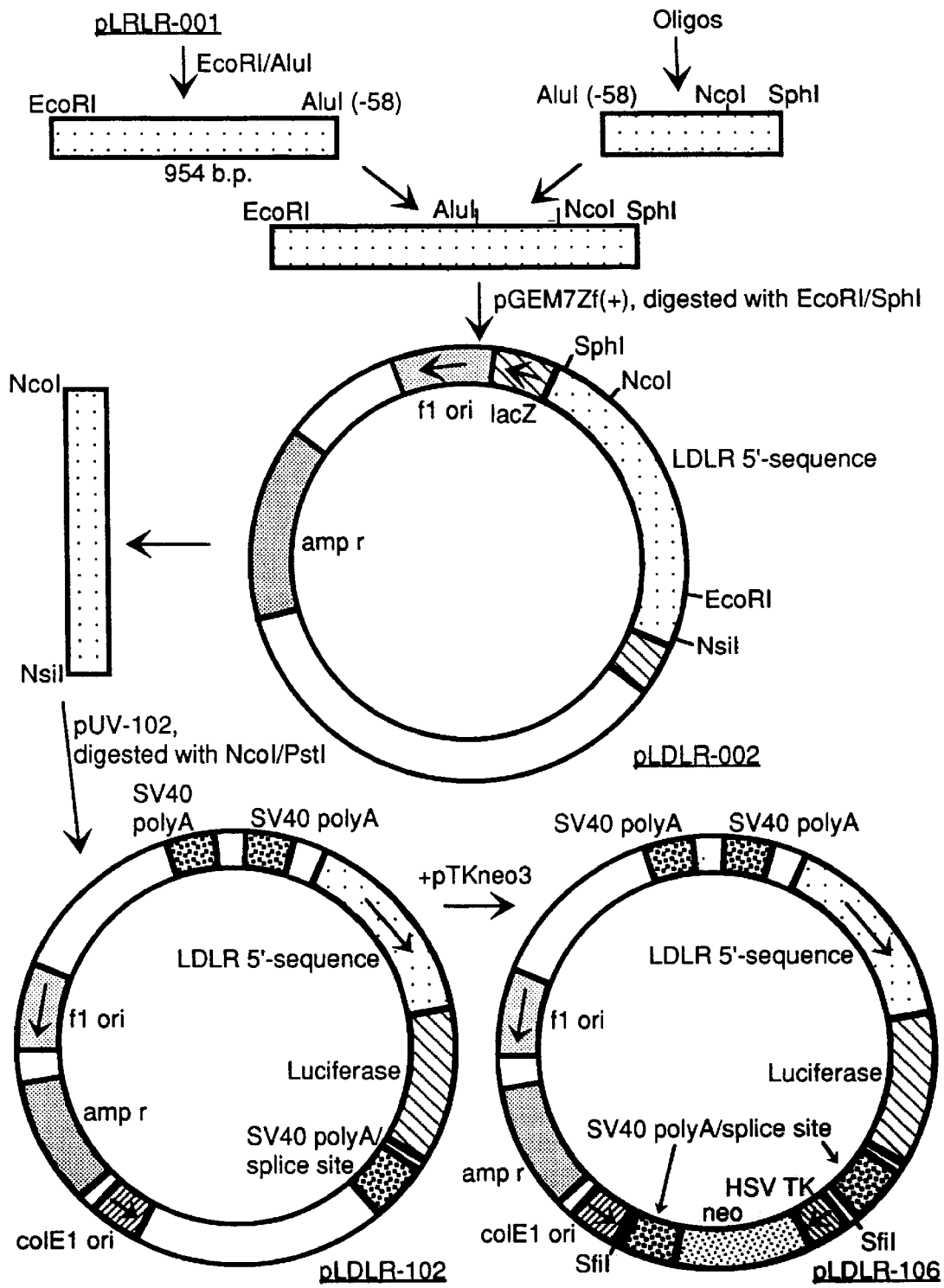
FIG. 18 shows the molecular cloning method for insertion of the regulatory and promoter elements of the LDL receptor gene into the mammalian expression shuttle vector. Details of the cloning method, including sequence information for oligonucleotide, are given in section C, part 4. Numbers (–58) in parentheses refer to a restriction site 58 base pairs upstream of the LDL receptor gene translational initiation codon.*
Figure 19:
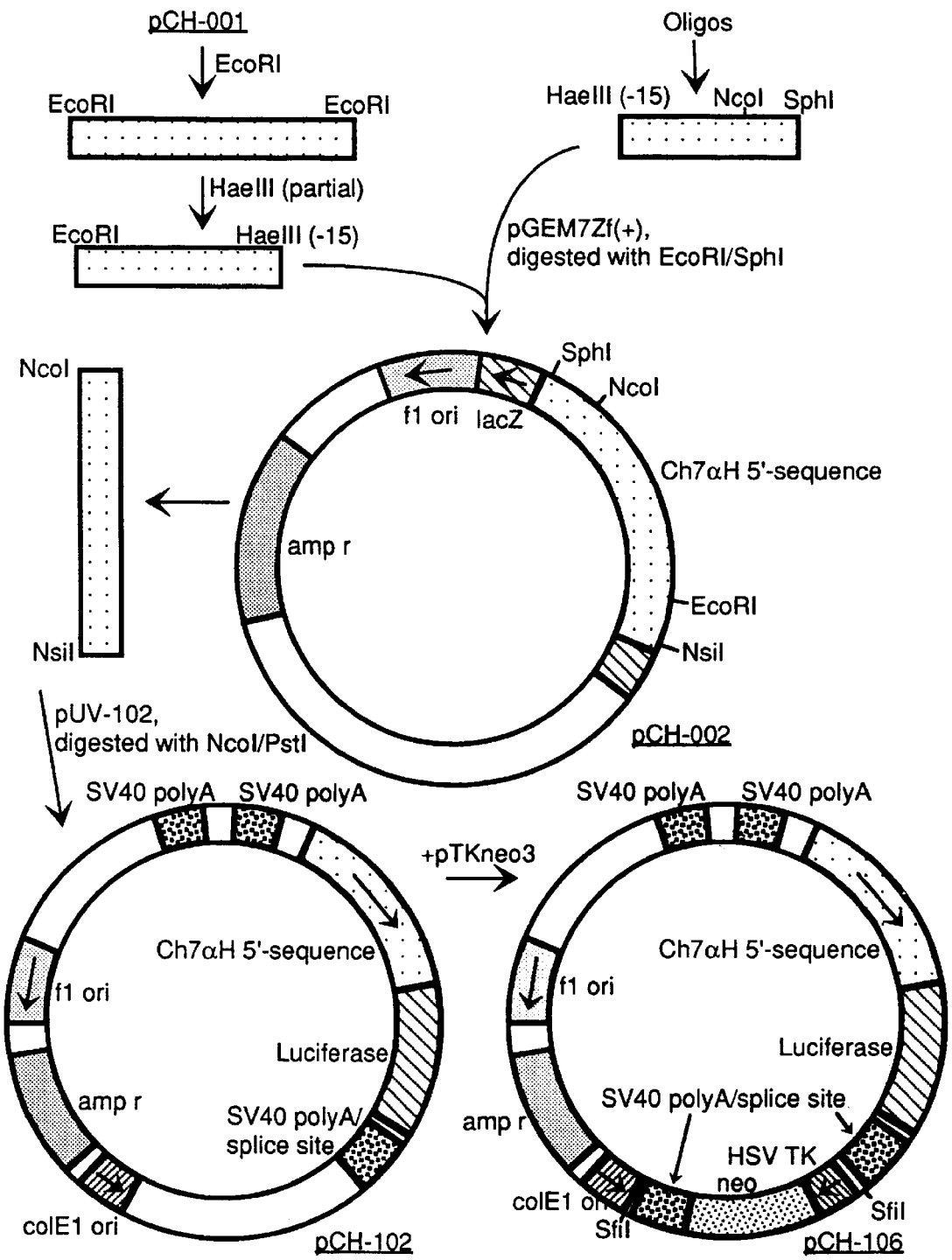
FIG. 19 shows the molecular cloning method of the insertion of the regulatory and promoter elements of the cholesterol 7α hydroxylase gene into the mammalian shuttle vector. Details of the cloning method including sequence information for the oligonucleotide are given in section C, part 5. Numbers (–15) refer to the restriction site 15 base pairs upstream from the 7α-cholesterol gene translational initiation codon.*
Figure 20:
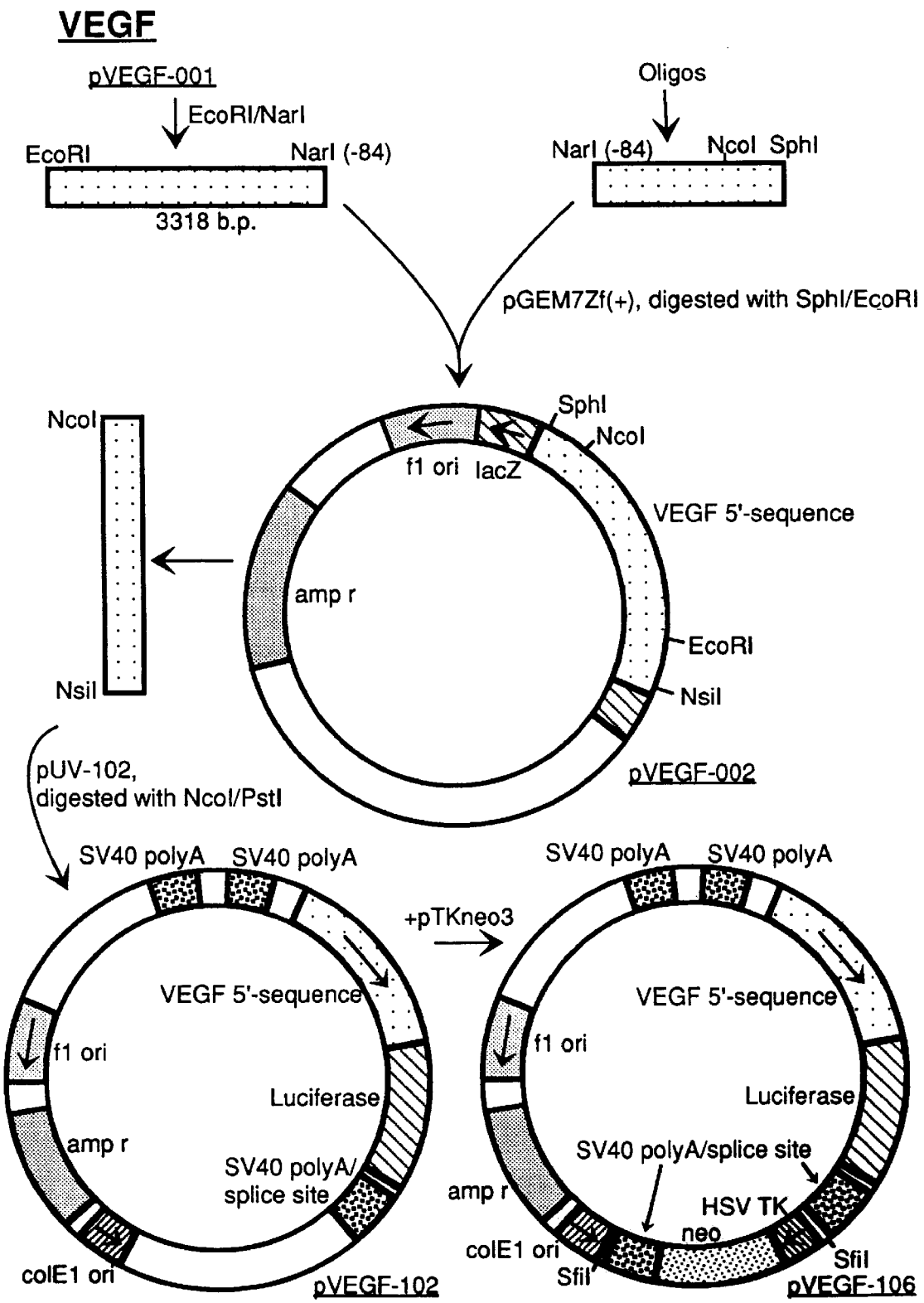
FIG. 20 shows the molecular cloning method for insertion of the regulatory and promoter elements of the VEGF gene into the mammalian expression shuttle vector. Details of the cloning method, including sequence information for oligonucleotide, are given in section C, part 6. Numbers (–84) in parentheses refer to a restriction site 84 base pairs upstream of the VEGF gene translational initiation codon.*

The neomycin resistance gene (neo) was then placed under control of the Herpes Simplex Virus thymidine kinase (HSV-TK) promoter to generate a resistance cassette which is free of known enhancer sequences. To do this the HSV-TK promoter was synthesized using four oligonucleotides (FIGS. 10A–10B)(SEQ ID NO: 11–14) designed according to published sequence information (79), and including an SfiI restriction site 5' of the HSV-TK sequences. These oligonucleotides were phosphorylated, annealed, ligated and inserted into pUV100 digested previously with HindIII/NheI, generating the vector pTKL 100 (FIG. 11). After verifying the HSV-TK sequence, the about 3.5 kb NheI/SmaI fragment was isolated from pTKL100, and the about 0.9 kb BstBI/BglII fragment containing the neo coding region was isolated from pRSVNEO (80). These two fragments were filled in with Klenow polymerase and ligated to form pTKNEO (FIG. 12). An additional SfiI site was then inserted 3' of the neo gene by isolating the about 1.8 kb SfiI/BamHI and about 2.6 kb SfiI/PVUII fragments of pTK-NEO and conducting a three way ligation along with a synthesized SfiI oligonucleotide generating pTKNEO2 (FIG. 13) (SEQ ID NO: 15–16). The HSV-TK/NEO vector containing an optimized Kozac sequence was also utilized (Stratagene, La Jolla, Calif., pMC1NEO). An additional vector was constructed by replacing the about 0.9 kb EcoRI/SalI fragment of pTKNEO2 with the about 0.9 kb EcoRI/SalI fragment from pMC1NEO. This vector was termed pTKNEO3. (FIG. 14). The SfiI fragment of pTKNEO3, containing the TK promoter and the neomycin resistance gene, was cloned into the SfiI site of pUV102 to yield pUV106.

3. Liquid Scintillation Counter Bioluminescence Assay

To assay for luciferase expression in transient expression assays in the various transfected clones (see below), cells were incubated with various transcriptional inducers in serum free defined media, washed 3 times with Dulbecco's phosphate-buffered saline (D-PBS, Gibco) and lysed in Lysis Buffer 1 (50 mM Tris acetate pH 7.9, 1 mM EDTA, 10 mM magnesium acetate, 1 mg/ml bovine serum albumin [BSA], 0.5% Brij 58, 2 mM ATP, 100 mM dithiothreitol [DTT]). All reagents were obtained from Sigma except for DTT which was from Boehringer Mannheim. After lysis, cell debris was sedimented by brief centrifugation, and 950 µl of supernatant extract were added to a glass scintillation vial. Samples were counted individually in an LKB (Gaithersburg, Md.) scintillation counter on a setting which allows measurement of individual photons by switching off the coincidence circuit. The reaction was started by addition of 50 µl of 2 mM luciferin (Sigma, St. Louis, Mo. or Boehringer Mannheim, Indianapolis Ind.) in Buffer B (Buffer B-Lysis Buffer 1 without Brij 58, ATP and DTT) to the 950 µl of lysate. Measurement was started 20 seconds after luciferin addition and continued for 1 minute. Results were normalized to protein concentration using the Bradford protein assay (BioRad, Richmond Calif.) or to cell numbers using Trypan Blue (Sigma) exclusion counting in a hemocytometer.

4/High Throughput Screening

Cell plating: Dynatech Microlite 96 well plates were pretreated for cell attachment by Dynatech Laboratories, Inc.(Chantilly, Va.). Alternatively, the 96 well plates were treated with 50 µl per well of human fibronectin (hFN, 15 µg/ml in PBS, Collaborative Research, Bedford, Mass.) overnight at 37° C. hFN-treated plates were washed with PBS using an Ultrawash 2 Microplate Washer (Dynatech Labs), to remove excess hFN prior to cell plating. M10 and G21 cells maintained in their respective serum media (with 0.2 mg/ml G418) were washed with PBS, harvested by trypsinization, and counted using a hemocytometer and the Trypan Blue exclusion method according to protocols provided by Sigma, St. Louis, Mo. Chemical Company. Cells were then diluted into serum free defined media (with 0.2 mg/ml G418), and 0.2 ml of cell suspension per well was plated onto Dynatech treated plates (G21) or hFN-treated plates (M10 and 532) using a Cetus Pro/Pette (Cetus, Emeryville Calif.). Plates were incubated overnight at 37° C. in a humidified 5% $CO_2$ atmosphere.

Addition of Chemicals to Cells: Chemicals were dissolved in DMSO at concentrations of 3–30 mg/ml. A liquid handling laboratory work station (RSP 5052, Tecan U.S. Chapel Hill, N.C.) was used to dilute the chemicals (three dilutions; 5 fold, 110 fold, and 726 fold). 10 µl of each dilution were added to each of quadruplicate samples of cells contained in the wells of 96-well Dynatech Microlite Plates. Cell plates were then shaken on a microplate shaker (Dynatech, medium setting, 30 sec.) and incubated for 6 hours at 37° C., 5% $CO_2$.

Bioluminescence Assay: After incubation with OSI-file chemicals, cell plates were washed 3 times with PBS using an Ultrawash 2 Microplate Washer (Dynatech Labs) and 75 µl of Lysis Buffer 2 were added to each well (Lysis Buffer 2 is the same as Lysis buffer 1 except that the ATP and DTT concentrations were changed to 2.67 mM and 133 mM, respectively). Bioluminescence was initiated by the addition of 25 µl 0.4 µM Luciferin in Buffer B to each well, and was measured in a Dynatech ML 1000 luminometer following a 1 minute incubation at room temperature. Data were captured and analyzed using Lotus-Measure (Lotus) software.

More recently the cell lysis buffer was modified to also contain the luciferin. Therefore, lysis of cells and the bioluminescence reaction begin simultaneously and the production of bioluminescent light reaches a maximum at about 5 min. The level of light output declines by about 20% within further 30 min. For better lysis buffer stability bovine serum albumin has been omitted. This improved lysis buffer has been shown to remain fully functional for at least 12 hours, when kept on ice and protected from direct light.

Also, more recently, a fully automated device as described in U.S. patent application Ser. No. 382,483 was used to incubate luciferase reporter cells in 96-well microtiter plates, transfer chemicals and known transcriptional modulators to the cells, incubate cells with the chemicals, remove the chemicals by washing with PBS, add lysis buffer to the cells and measure the bioluminescence produced.

An additional recent improvement is the ability to screen suspension cell lines in the automated high throughput mode using opaque, 96 well filter plates (Millititer Plates, Millipore Corp.). This involved the manufacture of a robotic filtration and washing station.

5. Isolation of Total Cellular RNA

Total cellular RNA was isolated from the luciferase-fusion containing cell clones or from untransfected host cells following incubation with various transcriptionally modulating chemicals known previously to affect gene expression. Total cellular RNA was isolated using the RNAZol method (CINNA/BIOTECX, Friendswood, Tex., Laboratories International, Inc.). Cells were resuspended and lysed with RNAZol solution (1.5 ml/9 cm petri dish) and the RNA was solubilized by passing the lysate a few times through a pipette. Chloroform was added to the homogenate (0.1 ml/1.0 ml), and samples were shaken for 15 seconds followed by a 5 minute incubation on ice. After centrifuging for 10 minutes, the upper phase was collected and an equal volume of isopropanol was added. Samples were incubated for 45 minutes at −20° C., and the RNA was pelleted for 15 minutes at 12,000×g at 4° C. The RNA pellet was then washed with 70% ethanol and dried briefly under vacuum.

6. Northern Blotting

Total cellular RNA was isolated from cells following incubation with chemicals as described above and electrophoresed in a 1% Agarose Formaldehyde gel. The RNA was transferred to Duralon-UV nylon filters (Stratagene, La Jolla, Calif.) using the manufacturer's recommended protocol. The filters were prehybridized for 4 hours (prehybridizing solution=5× SSC, 50 mM sodium pyrophosphate, 10× Denhardt's solution, 10% dextran sulfate, 7% SDS and 250 µg/ml denatured ssDNA) and then hybridized in the same solution for 16 hours at 65° C. in the presence of specific probes. The G-CSF probe was a 0.6 kb AflII to XhoI fragment which contained most of exon 5 of the human G-CSF gene. The β-actin (Oncor, Gaithersburg, Md.) probe was used as a control probe to normalize for the total amount of RNA. The probes were labeled with alpha-32P dCTP using a random primed DNA labeling kit (Amersham, Arlington, Ill.). Following hybridization, filters were washed three times at room temperature with 1× SSC, 0.13% SDS and three times at 65° C. with 0.2× SSC, 0.1% SDS. Filters were first probed with the G-CSF specific probe and then reprobed with β-actin-probe. Exposure to x-ray film was performed overnight. Bands were excised and counted in a liquid scintillation counter (LKB, Gaithersburg, Md.), and counts obtained with the G-CSF specific probe were normalized relative to the counts obtained with the β-Actin specific probe.

7. S1 Nuclease Protection Assays

S1 Nuclease protection assays were carried out as described in reference 118.

8. Southern Blotting

To monitor correct and complete stable integration of transfected promoter/reporter constructs, stably transfected cell clones were subjected to Southern blot analysis. Genomic DNA was prepared of each clone to be tested and restriction-cut with DraI or another appropriate restriction endonuclease. After electrophoresis, transfer to nylon filters and immobilization by UV irradiation using a Stratalinker UV device (Stratagene, La Jolla, Calif.), integrated promoter/luciferase fusion constructs were visualized by probing with radioactively labelled XbaI-EcoRI fragments of the luciferase coding region. Probes were labelled using the random primer method (81). Since DraI cuts in the SV40 polyadenylation sites located in the mammalian expression shuttle vector just upstream the inserted promoter sequences as well as downstream of the luciferase coding region, but not in most of the promoter sequences used for generating stably transfected cell clones, a single fragment should be visualized by the probe used. The size of that fragment should be characteristic for each of the promoter sequences analyzed.

9. MTT Cellular Toxicity Assay

To determine cytotoxic concentrations of chemicals registering as positives in the high throughput luciferase assay the MTT cytotoxicity assay was employed (82). In this assay, a tetrazolium salt [3-(4,5-dimethylthiazol-2-yl)-2,5-diphenyl-tetrazolium bromide, MTT] is reduced to a colored formazon product by reducing enzymes present only in living metabolically active cells.

10. Immunoassays

Supernatants from 5637 bladder carcinoma cells incubated with chemicals registering as positives in the G-CSF promoter/luciferase high throughput assay were assayed for secreted G-CSF protein using the two-antibody sandwich immunoassay (83). The G-CSF Assay kit manufactured by Oncogene Science, Inc. was used and the manufacturer's instructions were followed.

11. Two Dimensional Gels

Two dimensional protein gels are carried out using published procedures (88).

12. Transfection

Cells are transfected by one of three methods, following manufacturer's instructions; by Calcium phosphate precipitation (Pharmacia), Lipofection (Life Technologies Inc.) or electroporation (BioRad). In most cases, 25–75 µg of plasmid DNA, linearized by a single restriction endonuclease cut within the vector sequences, is electroporated into approximately 5 million cells. When co-transfection of a separate neomycin resistant plasmid was employed the molar ratio of luciferase fusion plasmid to neomycin resistant plasmid was either 10:1 or 20:1. Neomycin resistant clones are selected by growth in media containing G418 (Geneticin, Gibco). In experiments requiring a control for transfection efficiency a vector containing an SV40 early promoter-β-galactosidase chimeric gene is co-transfected.

13. PCR (Polymerase Chain Reaction)

Total RNA was isolated using the approach described above, first strand cDNA generated by either oligo dT, random hexamer or gene specific oligonucleotide priming. Specific amplification oligonucleotides were added, and the polymerase chain reaction carried out according to established methods (84).

RNA levels are quantitated by established methods (85) which include the addition of varying amounts of a control RNA and thereby establishing a standard curve. PCR products are visualized on an Ethidium bromide stained agarose gel and are quantitated by measuring the incorporation of radiolabelled deoxynucleotide triphosphates using liquid scintillation.

14. High Throughput Quantitative PCR

Current methods for measuring changes in gene expression suffer from various limitations. Conventional direct analysis of changes in mRNA levels (nuclease protection, Northern blot, primer extension) lack sufficient sensitivity for use with high throughput formats (e.g. 96 well plate cell culture). These methods also require difficult analytical procedures (e.g. sequencing gels) complicating automation. The use of gene fusions (luciferase or CAT transcriptional fusions) as demonstrated above, provide sufficient sensitivity and ease of analysis but require disruption of the native transcription unit and loss of chromosomal context, leading to potential artifact. This section of the invention proposes to circumvent the sensitivity limitation of direct analysis by using the amplification potential inherent in the polymerase chain reaction. Combining PCR with the ease of florescence detection of will allow direct mRNA analysis in a high throughput mode.

The following description outlines a high throughput drug screen utilizing direct PCR quantitation of mRNA in its most simple format.

1. Grow cells. Cells are grown in 96 well microtiter plates as described above. The final detection step is a fluorescence measurement, so an opaque (non-reflecting black) plate is required.

2. Add compounds. As with the luciferase reporter screen, compounds are added at several concentrations and at several replications. The number of duplicate samples required can be determined statistically after the basic assay is formatted (currently, quadruplicates are required).

3. Incubate. The incubation time depends on the biology of the systems studied. As with the current luciferase reporter assay, the incubation time is 24 hours.

4. Lyse cells: The cells are lysed in a buffer which satisfies several important criteria. A. Avoidance of extremes of temperature. B. Complete inactivation of contaminating cellular nucleases. C. Compatible with subsequent RNA purification steps. D. Rapid and efficient lysis. Chaotropic buffers have been described which satisfy these requirements. Guanidine HCl (6M) will efficiently lyse cells and effectively inactivate cellular nucleases. The kinetics of nucleic acid hybridization are largely unaffected by these conditions. Thus, the subsequent RNA purification (separation using magnetic oligo dT beads, see below) does not require a buffer change.

5. Add external control: The exponential nature of the PCR amplification step tends to magnify small differences in conditions. Key to the usefulness of this approach is the careful inclusion of appropriate standards for control purposes. An artificial polyadenylated RNA (generated with phage T7 RNA polymerase and commercially available vectors, Promega Madison Wis.) is added at this point. This RNA serves as a control for all of the following steps: Purification, cDNA synthesis, PCR amplification, PCR product purification and detection. This control RNA is added to several lysates at varying concentrations, generating a standard curve.

6. Purify RNA: RNA is purified using commercially available oligo-dT tagged magnetic beads. These beads are added to the lysate, allowed to hybridize to the mRNA, brought to the bottom of the plate using a strong magnet, and extensively washed to remove protein and DNA.

7. Synthesize cDNA: cDNA is generated using the 3' end of the bead bound oligo-dT.

8. Add PCR primers: Each gene (or control) to be assayed requires two oligos. The pair are designed so that they span a large intron. This makes the amplification much more RNA specific. The short, spliced RNA target is much more efficiently amplified than the longer, contaminating genomic DNA target. One of the oligo pair is tagged at its 5' end with a fluorescent label. The other oligo is tagged at its 5' end with biotin (for future purification, see below). Several sets of oligos are added to each lysate. A set for each control and a set for each gene to be assayed. Every set has a different fluorescent tag.

9. PCR Amplification: Simultaneous incubation of many plates is required, so either a large array of blocks or a large capacity convection oven is necessary.

10. Purification of PCR products: The PCR products are separated from the unreacted oligos using a method similar to the one employed for the initial RNA purification. Magnetic beads, tagged with streptavidan are added to the mixture. PCR products are tagged on one end with biotin (on the other with a fluorescent label) and tightly attach to the magnetic beads. The beads, along with the labeled polynucleotides, are brought to the bottom of the plate with a magnet and extensively washed.

11. Detection: The plates are read in a 96 well fluorimeter (Amersham).

12. Data analysis: A ratio of fluorescence from a particular gene's PCR product to the signal from the "constitutive" internal control gives the relative mRNA level. Changes in this ratio indicates a change in gene expression. Absolute mRNA levels are determined by control experiments using carefully quantitated artificial RNAs to construct standard curves for each gene studied. This establishes a given ratio (to the internal control) for a given cellular RNA concentration.

C/GENE CLONING/VECTOR CONSTRUCTION

1/Introduction

Molecular Cloning of Cardiovascular Gene Promoters and Regulatory Elements and Insertion into the Mammalian Expression Shuttle Vector Strategy: This section describes (a) the molecular cloning of the promoter and transcriptionally modulatable regulatory sequences of the human genes encoding (1) apolipoprotein (a), (2) apolipoprotein AI, (3) apolipoprotein B, (4) LDL receptor, (5) cholesterol 7α-hydroxylase, (6) vascular endothelial growth factor (VEGF), (7) colony stimulating factor-1 (CSF-1, M-CSF), (8) monocyte chemoattractant protein-1 (MCP-1) (9) β-fibrinogen, (10) scavenger receptor, (11) granulocyte colony stimulating factor (G-CSF), (12) granulocyte-macrophage colony stimulating factor (GM-CSF), and (13) renin, (14) calcitonin, (15) PEPCK and (b), the making of constructs where these regulatory sequences control the expression of the firefly luciferase gene. These constructs were transfected into cells as described below and analyzed for their utility as reporters for the discovery of gene expression modulating compounds (for example, in a high-throughput screen to identify chemicals acting as specific transcriptional modulators.

To make such constructs, several kilobases of sequence upstream of the transcription start site, along with 5' untranslated sequences up to the translation start site (ATG) of a gene of interest were inserted 5' of the luciferase coding region, along with any additional sequences (e.g. intronic enhancers) required for properly regulated expression of the luciferase reporter. In this way constructs can be made where all sequences upstream of their translation start site are from the gene of interest, and all coding sequences are from the luciferase gene. How this was accomplished for the individual genes is described below.

If a construct produces no (or unregulated) luciferase activity, regulatory elements necessary for apo(a) transcription or translation may reside external to those sequences subcloned. Further necessary control regions will be identified by subcloning further 5' flanking sequences, and possibly intronic and 3' sequences, using partially digested (e.g. Sau3A1) one kb cassettes from the original genomic clone, into the reporter vector.

1/Apolipoprotein (a) gene

Sequence information on the Apolipoprotein (a) gene (38) is used to synthesize oligonucleotide probes (Aposma-(1-3)) in order to screen a human leukocyte genomic DNA library in EMBL-3 (Clontech, Palo Alto, Calif.) according to the supplier's instructions. The sequences of the oligonucleotide probes (SEQ ID NO: 17–19) are:

5' TATTTCTGAAATCAGCAGCACCTGAGCAAA 3'
(Aposma --- 1)

5' TGGAACATAAGGAAGTGGTTCTTCTACTTC 3'
(Aposma --- 2)

5' CATGTGGTCCAGGATTGCTACCATGGTGATGG 3'
(Aposma --- 3)

The sequence of these probes corresponds to sequence at the 5' end of the Apolipoprotein (a) gene coding sequence. After selecting positive plaques screened using a mixture of all three oligonucleotides, these are rescreened with Aposma-1 using 25% formamide at 50° C., with 2SSC washed Aposma-1 spans the coding regions for the end of the apolipoprotein(a) prepeptide and its mature amino terminus, thus crossing the region of plasminogen (>1000 b.p.) which is absent in apolipoprotein(a). Thus under these conditions Aposma-1 is specific for apolipoprotein(a). Positive plaques are subcloned into pBluescript KS(+) (Stratagene, La Jolla, Calif.) to create pAposma001.

A set of oligonucleotides are designed to act as synthetic linkers to span from the EaeI site (at position −13 from the Apolipoprotein (a) AUG initiation codon) in the 5' untranslated region of the Apolipoprotein (a) gene to the NcoI site in pUV106 (the AUG of the luciferase ORF). The G in parentheses in oligo 2 is a substitution for a T just 5' of the translational initiation codon in the Apolipoprotein (a) complimentary sequence in order to make an NcoI sticky end (SEQ ID NO: 20–21).

Oligo 1: 5'-GGCCAGTCCCAA 3'
Oligo 2: 5'-CAT(G) TTGGGACT 3'

Oligo 1 is annealed to oligo 2, and the resulting pair of linkers ligated to a gel purified EaeI fragment excised from Aposma001, corresponding to the Apolipoprotein (a) promoter, upstream regulatory elements and a portion of the 5' leader sequence. The ligated fragments are inserted into NcoI-NotI digested pGEM5Zf(+) and the correct orientation of the fragments established by restriction mapping, to create pAposma002.

An NsiI-NcoI fragment of pAposma002, containing the entire Apolipoprotein (a) promoter and 5' leader, is gel purified and ligated into pUV102 which has been digested with PstI and NcoI to generate pAposma102. The SfiI fragment from pTKneo3 is gel purified and ligated into SfiI digested pAposma102. to generate pAposma106. This construct is then used to generate stable transfections of Hep G2 cells.

2/Apolipoprotein AI gene

Sequence information on the Apolipoprotein AI gene (71, 86) is used to synthesize oligonucleotide probes (ApoAI-1 to 3)) in order to screen a human leukocyte genomic DNA library in EMBL-3 (Clontech, Palo Alto, Calif.) according to the supplier's instructions. The sequence of the oligonucleotide probes (SEQ ID NO: 22–24) are:

Positive plaques are subcloned into pBluescript KS(+) (Stratagene, La Jolla, Calif.) to create pApoAI-001.

A set of 4 oligonucleotides are designed to act as synthetic linkers to span from the KpnI site (at position −162 from the Apolipoprotein AI AUG initiation codon) in the 5' untranslated region of the Apolipoprotein AI gene to the NcoI site in pUV106 (the AUG of the luciferase ORF) to an SphI site for insertion into pGEM7Zf(+). The G/C base pairs in parentheses in oligos 3 and 4 are substitutions for C/G base pairs just 5' of the translational initiation codon in the Apolipoprotein AI in order to make an NcoI restriction site (SEQ ID NO: 25–28).

Oligo-1: 5'-CTGAGGTCTTCTCCCGCTCTGTGCCCTTCTCCTCACCTGG CTGCAACTGAGTTCGGGGAGCACGGGGCTTC 3'
Oligo-2: 5'-TGCAGAAGCCCCGTGCTCCCCGAACACAGTTGCAGCCAG GAGAGGAGAAGGGCACAGAGCGGGAGAAGACCTCAGGTAC 3'
Oligo-3: 5'-TGCATGCTGAAGGCACCCACTCAGCCAGGCCCTTCTTCTC CTCCAGGTCCCCCACGGCCCTTCA(C)(C)ATGGTCCCGGCCGGCATG
Oligo-4: 5'-CCGGCCGGGACCAT(G)(G)TGAAGGGCCGTGGGGGACCTG GAGGAGAAGAAGGGCCTGCCTGAGTGGGTGCCTTCAGCA 3'

Oligo 1 is annealed to oligo 2, oligo 3 is annealed to oligo 4, and the resulting pair of linkers ligated into pGEM-7Zf(+) digested with KpnI and SphI to create pApoAI-002.

A KpnI 2052 b.p. fragment of pApoAI-001, corresponding to the Apolipoprotein AI promoter, upstream regulatory elements and a portion of the 5' leader sequence is gel purified and ligated into KpnI digested pApoAI-002. The correct orientation of the inserted fragment is confirmed by restriction mapping to create pApoAI-003.

An NsiI-NcoI fragment of pApoAI-003, containing the entire Apolipoprotein AI promoter and 5' leader, is gel purified and ligated into pUV102 which has been digested with PstI and NcoI to generate pApoAI-102. The SfiI fragment from pTKneo3 is gel purified and ligated into SfiI digested pApoAI-102 to generate pApoAI-106. This construct is then used to generate stable transfections of HepG2 cells.

3/Apolipoprotein B gene

Sequence information on the Apolipoprotein B gene (39, Genbank) is used to synthesize oligonucleotide probes (ApoB-1 to 3)) in order to screen a human leukocyte genomic DNA library in EMBL-3 (Clontech, Palo Alto, Calif.A) according to the supplier's instructions. The 5' GCTGCGGTGCTGACCTTGGCCGTGCTCTTCCTGACGGGTA 3' (ApoAI-1)

5' GGTGTCCCCTAACCTAGGGAGCCAACCATCGGG 3' (ApoAI-2)

5' GGGCCTTCTCCCTAAATCCCCGTGGCCACCTCCTG 3' (ApoAI-3)

The sequence of these probes corresponds to sequence at the 5' end of the Apolipoprotein AI gene coding sequence.

sequences of the oligonucleotide probes (SEQ ID NO: 29–31) are:

5' GGCCGCAGCCCAGGAGCCGCCCCACCGCAG 3'   (ApoB-1)

5' TGAGTGCCCTTCTCGGTTGCTGCCGCTGAGGAG 3'   (ApoB-2)

5' CTGGCGATGGACCCGCCGAGGCCCGCGCTGCTGGCG 3'   (ApoB-3)

The sequence of these probes corresponds to sequence at the 5' end of the apolipoprotein B gene coding and untranslated sequences. Positive plaques are subcloned into pBluescript KS (+) (Stratagene, La Jolla, Calif.) to create pApoB-001.

A set of 2 oligonucleotides (SEQ ID NO: 32–33) are designed to act as synthetic linkers to span from the PvuII site (at position −7 from the Apolipoprotein B AUG initiation codon) in the 5' untranslated region of the Apolipoprotein B gene to the XbaI site in pUV106 (at the 5' end of the luciferase coding region).

The sequence of these probes corresponds to sequences at the 5' end of the LDL receptor gene coding sequence and in the 5' untranslated region. Positive plaques are subcloned into pBluescript KS(+) (Stratagene, La Jolla, Calif.) to create pLDLR-001.

A set of 2 oligonucleotides (SEQ ID NO: 37–38) are designed to act as synthetic linkers to span from the AluI site (at position −58 from the LDL receptor AUG initiation codon) in the 5' untranslated region of the LDL receptor gene, to the NcoI site in pUV106 (the AUG of the luciferase ORF), to an SphI site for subcloning into pGEM-7Zf(+). The Oligo-1: 5'-CTGGCGATGGAAGACGCCAAAAACATCAAGAAAGGCCCGGCGCCATTCTATCCT 3'

Oligo-2: 5'-CTAGAGGATAGAATGGCGCCGGGCCTTTCTTGATGTTTTTGGCGTCTTCCATCGCCAG 3'

Oligo 1 is annealed to oligo 2, and the resulting linker ligated with a gel purified NsiI-PvuII 954 bp fragment of pApoB-001, corresponding to the Apolipoprotein B promoter, upstream regulatory elements and a portion of the 5' leader sequence. The ligated fragments are inserted into G/C base pair in parentheses in oligos 1 and 2 are substitutions for C/G base pairs just 5' of the translational initiation codon in the LDL receptor in order to make an NcoI restriction site.

Oligo-1: 5'-CTAGGACACAGCAGGTCGTGATCCGGGTCGGGACACTGCCTGGCAGAGGCTGCGA(C)CATGGTCCCGGCCGGCATG 3'

Oligo-2: 5'-CCGGCCGGGACCATG(G)TCGCAGCCTCTGCCAGGCAGTGTCCCGACCCGGATCACGACCTGCTGTGTCCTAG 3'

NsiI-XbaI digested pGEM7Zf(+). Correct insertion of the fragments is confirmed by restriction mapping to create pApoB-002.

An NsiI-XbaI fragment of pApoB-002, containing the entire Apolipoprotein B promoter and 5' leader, is gel purified and ligated into pUV102 which has been digested with PstI and XbaI to generate pApoB-102. The SfiI fragment from pTKneo3 is gel purified and ligated into SfiI digested pApoB-102 to generate pApoB-106. This construct is then used to generate stable transfections of Hep G2 cells.

4/LDL receptor gene

Sequence information on the LDL receptor gene (40, 87, Genbank) is used to synthesize oligonucleotide probes (LDLR-1 to 3)) in order to screen a human leukocyte genomic DNA library in EMBL-3 (Clontech, Palo Alto, Calif.) according to the supplier's instructions. The sequence of the oligonucleotide probes (SEQ ID NO: 34–36) are:

Oligo 1 is annealed to oligo 2, and the resulting linker ligated to a gel purified 1471 b.p. EcoRI-AluI fragment of pLDLR-001, corresponding to the LDL receptor promoter, upstream regulatory elements and a portion of the 5' leader sequence. This is then ligated into EcoRI-SphI digested pGEM-7Zf(+). Correct insertion of the fragments is confirmed by restriction mapping to create pLDLR-002.

An NsiI-NcoI fragment of pLDLR-002, containing the entire LDL receptor promoter and 5' leader, is gel purified and ligated into pUV102 which has been digested with PstI and NcoI to generate pLDLR-102. The SfiI fragment from pTKneo3 is gel purified and ligated into SfiI digested pLDLR-102 to generate pLDLR-106. This construct is then used to generate stable transfections of Hep G2 cells.

5/cholesterol 7α-hydroxylase gene

Sequence information on the cholesterol 7α-hydroxylase gene (24) is used to synthesize oligonucleotide probes

5' GGGGCCCTGGGGCTGGAAATTGCGCTGGACCGTCGCCTTGCTC 3'   (LDLR-1)

5' GGGCGACAGATGTGAAAGAAACGAGTTCCAGTGCCAAGACGGG 3'   (LDLR-2)

5' CGAGTGCAATCGCGGGAAGCCAGGGTTTCC 3'   (LDLR-3)

(CH-1 to 3) in order to screen a human leukocyte genomic DNA library in EMBL-3 (Clontech, Palo Alto, Calif.) according to the supplier's instructions. The sequence of the oligonucleotide probes (SEQ ID NO: 39–41) are:

5' ATGATGACCACATCTTTGATTTGGGGGATTGCTATAGCAGCA 3'  (CH-1)

5' GATTTTCTTCCTCAGAGATTTTGGCCTAGATTTGC 3'  (CH-2)

5' GCTGTTGTCTATGGCTTATTCTTGGAATTAGGAGAAGGCAAACGG 3'  (CH-3)

The sequence of these probes corresponds to sequence at the 5' end of the cholesterol 7α-hydroxylase gene coding sequence and the 5' untranslated region. Positive plaques are subcloned into pBluescript KS(+) (Stratagene, La Jolla, Calif.) to create pCH-001. From pCH-001 an EcoRI fragment containing the cholesterol 7α-hydroxylase promoter, upstream regulatory elements, 5' leader sequence and part of the coding domain is isolated and gel purified. This fragment is subjected to partial digestion with HaeIII, and an EcoRI-HaeIII fragment starting 15 b.p. upstream of the translational initiation site, containing the cholesterol 7α-hydroxylase promoter, upstream regulatory elements, and part of the 5' leader sequence, is gel purified.

A set of 2 oligonucleotides (SEQ ID NO: 42–43) are designed to act as synthetic linkers to span from the HaeIII site (at position −15 from the cholesterol 7α-hydroxylase AUG initiation codon) in the 5' untranslated region of the cholesterol 7α-hydroxylase gene, to the NcoI site in pUV106 (the AUG of the luciferase ORF), to an SphI site for subcloning into pGEM-7Zf(+). The C/G base pairs in parentheses in oligos 1 and 2 are substitutions for A/T base pairs just 5' of the translational initiation codon in cholesterol 7α-hydroxylase in order to make an NcoI restriction site. These substitutions also produce a better translational initiation site by providing an optimal context for the AUG initiation codon.

Oligo 1:

5'-CCTAGATTTGCA(C)(C)ATGGTCCCGGCCGGCATG 3'

Oligo 2:

5'-CCGGCCGGGACCAT(G)(G)TGCAAATCTAGG 3'

Oligo 1 is annealed to oligo 2, and the resulting linker and the gel purified EcoRI-HaeIII fragment of pCH-001 ligated into EcoRI-SphI digested pGEM-7Zf(+). Correct insertion of the fragments is confirmed by restriction mapping to create pCH-002.

An NsiI-NcoI fragment of pCH-002, containing the entire cholesterol 7α-hydroxylase promoter and 5' leader, is gel purified and ligated into pUV102 which has been digested with PstI and NcoI to generate pCH-102. The SfiI fragment from pTKneo3 is gel purified and ligated into SfiI digested pCH-102 to generate pCH-106. This construct is then used to generate stable transfections of Hep G2 cells.

6/Vascular endothelial growth factor (VEGF) gene

Sequence information on the VEGF gene (42) is used to synthesize oligonucleotide probes (VEGF-1 to 3) in order to screen a human leukocyte genomic DNA library in EMBL-3 (Clontech, Palo Alto, Calif.) according to the supplier's instructions. The sequence of the oligonucleotide probes (SEQ ID NO: 44–46) are:

5' ATGAACTTTCTGCTGTCTTGGGTGCATTGGAGC 3'

(VEGF-1)

5' TTGCCTTGCTGCTCTACCTCCACCATGCCAAG 3'

(VEGF-2)

5' TCGCGGAGGCTTGGGGCAGCCGGGTAGCTCGGAGGT 3'

(VEGF-3)

The sequence of these probes corresponds to sequence at the 5' end of the VEGF gene coding sequence. Positive plaques are subcloned into pBluescript KS(+) (Stratagene, La Jolla, Calif.) to create pVEGF-001. From pVEGF-001 a 3318 b.p. EcoRI-NarI fragment containing the VEGF promoter, upstream regulatory elements and part of the 5' leader sequence is isolated and gel purified.

A set of 4 oligonucleotides (SEQ ID NO: 47–50) are designed to act as synthetic linkers to span from the NarI site (at position −84 from the VEGF AUG initiation codon) in the 5' untranslated region of the VEGF gene, to the NcoI site in pUv106 (the AUG of the luciferase ORF), to an SphI site for subcloning into pGEM-7Zf(+).

Oligo 1: 5'-CGCCGAGGAGAGCGGGCCGCCCCACAGCCCGAGCCGGAGAGGGA-3'

Oligo 2: 5'-CCGGCTCGGGCTGTGGGGCGGCCCGCTCTCCTCGG 3'

Oligo 3:

5' GCGCGAGCCGCGCCGGCCCCGGTCGGGCCTCCGAAACCATGGTCCCGGCCGGC

ATG 3'

Oligo 4: 5'-CCGGCCGGGACCATGGTTTCGGAGGCCCGACCGGGGCCGGCGCGGCTCGCGCTCCCTCT-3'

Oligo 1 is annealed to oligo 2, oligo 3 is annealed to oligo 4 and the resulting linkers and the gel purified EcoRI-NarI fragment of pVEGF-001 are ligated into EcoRI-SphI digested pGEM-7Zf(+). Correct insertion of the fragments is confirmed by restriction mapping to create pVEGF-002.

An NsiI-NcoI fragment of pVEGF-002, containing the entire VEGF promoter and 5' leader, is gel purified and ligated into pUV102 which has been digested with PstI and NcoI to generate pVEGF-102. The SfiI fragment from pTKneo3 is gel purified and ligated into SfiI digested pVEGF-102 to generate pVEGF-106. This construct is then used to generate stable transfections of U937 cells.

7/CSF-1 Human Macrophage Colony Stimulating Factor (M-CSF or CSF-1)

Sequence information on the M-CSF gene (89) was used to synthesize an oligonucleotide probe (CSF1-a) to screen a human leukocyte genomic DNA library (Clontech, Palo Alto, Calif.) according to the supplier's instructions. The sequence of the oligonucleotide probe (SEQ ID NO: 51) was:

5' CCGGCGCGGTCATACGGGCAGCTGG 3'   (CSF1-a)

The sequence of this probe corresponds to sequences within the second exon of the M-CSF gene. One of the clones isolated from the leukocyte library contains a 5 kb EcoRI/HindIII fragment which includes the first exon and 5' flanking region of M-CSF. This fragment was inserted into the pTZ18R vector (Pharmacia, Piscataway N.J.) which had been previously digested with EcoRI/HindIII resulting in the vector CSF1-pTZ18 (FIG. 127). The same fragment was isolated from CSF1-pTZ18, blunt ended at the EcoRI end, and inserted into the pUV100 vector which had been previously digested with SnaBI/HindIII, resulting in the vector p100-RH (FIG. 128). The M-CSF untranslated leader sequence (89) was then fused to the first codon of the luciferase coding region as follows: (a) a 740 bp PstI/PvuII fragment was isolated from CSF1-pTZ18 containing 570 bp of the M-CSF promoter and 170 bp of the untranslated leader sequence; (b) oligonucleotides containing sequences from the 3' end of the M-CSF leader sequence and the 5' end of the luciferase coding region were synthesized:

5' CTGCCCGTATGGA 3'   (CSF-luci5) (SEQ ID NO: 52)
5' ACGGGCAG 3'   (CSF-luci6);

(c) oligonucleotides pUV3 and pUV6 (previously used to construct pUV001, FIG. 104) were annealed, and digested with XbaI to release a 48 bp fragment which contains 48 bases of the luciferase coding region; (d) DNA fragments and oligonucleotides (from a, b and c) were ligated and inserted into pUV100 previously digested with PstI/XbaI to yield p100-2 (FIG. 129). A construct containing a larger M-CSF promoter fragment (5 kb) was also made. A 2 kb XmaI fragment was isolated from the plasmid p100-2. This fragment contains the 3' end of the M-CSF leader sequence fused to the luciferase start codon. The 2 kb XmaI fragment was inserted in p100-RH previously digested with XmaI, to yield p100-RHC (FIG. 130). The fused 5 kb M-CSF promoter-luciferase construct was then inserted into pUV102 as follows: a 5 kb NotI/XbaI fragment (blunt ended at the NotI end) was isolated from p100-RHC and inserted into pUV102, previously digested with SnaBI/XbaI, to generate pCSF1-102 (FIG. 131). This construct was then used for transfections of HL60 promylocytic leukemia cells.

8/Monocyte chemoattractant protein (MCP-1) gene

Sequence information on the MCP-1 gene (90) is used to synthesize oligonucleotide probes (MCP-1 to 3) in order to screen a human leukocyte genomic DNA library in EMBL-3 (Clontech, Palo Alto, Calif.) according to the supplier's instructions. The sequence of the oligonucleotide probes (SEQ ID NO: 53–55) are:

5' AGAAACATCCAATTCTCAAACTGAAGCTCGCACTCTCGCCTCCA 3'   (MCP-1)

5' ATGAAAGTCTCTGCCGCCCTTCTGTGCCTGCTGCTCAT 3'   (MCP-2)

5' GCAGCCACCTTCATTCCCCAAGGGCTCGCTCAGCCAG 3'   (MCP-3)

The sequence of these probes corresponds to sequences of the MCP-1 gene 5' leader and 5' coding region. Positive plaques are subcloned into pBluescript KS(+) (Stratagene, La Jolla, Calif.) to create pMCP-001. From pMCP-001 a fragment containing the MCP-1 promoter, upstream regulatory elements, 5' leader sequence and part of the coding domain (MCPDNA-1) is isolated and gel purified. MCPDNA-1 is subjected to digestion with EspI, and an EspI fragment starting 183 b.p. upstream of the translational initiation site, containing MCP-1 upstream regulatory elements is gel purified (MCPDNA-2). From the EspI digest a second 249 b.p. EspI fragment (MCPDNA-3) containing the MCP-1 promoter, translational initiation site, and some 5' coding sequence is also isolated and gel purified. MCPDNA-3 is digested with NlaIII and a 182 b.p. fragment containing MCP-1 promoter sequences is gel purified (MCPDNA-3a).

A set of 2 oligonucleotides (SEQ ID NO: 56–57) are designed to act as synthetic linkers to span from the PstI site in pUV102 to the 5' EspI site in MCPDNA-2:

Oligo 1: 5'-GTCCCGGCCGGC 3'
Oligo 2: 5'-TGAGCCGGCCGGGACTGCA 3'

Oligo 1 is annealed to oligo 2, and the resulting linker is ligated with MCPDNA-2 and MCPDNA-3a into PstI-NcoI digested pUV102 which has been blunt ended at the 5' NcoI overhang by treatment with mung bean 5'-endonuclease. Correct insertion of the fragments is confirmed by restriction mapping to create pMCP-102. The SfiI fragment from pTKneo3 is gel purified and ligated into SfiI digested pMCP-102 to generate pMCP-106. This construct is then used to generate stable transfections of WI38 cells.

9/Beta fibrinogen gene

Sequence information on the Beta fibrinogen gene (91) is used to synthesize oligonucleotide probes (FIB-1 to 3) in order to screen a human leukocyte genomic DNA library in EMBL-3 (Clontech, Palo Alto, Calif.) according to the supplier's instructions. The sequence of the oligonucleotide probes (SEQ ID NO: 58–60) are:

5' ATGAAAAGGATGGTTTCTTGGAGCTTCCACAAACTTAAAACCAT 3'   (FIB-1)

5' CTATTATTGCTACTATTGTGTGTTTTTCTAGTTAAGTCCCAAGGTGT 3'   (FIB-2)

5' GAGTCACGATTTTAGTGGTTGCCTTGTGAGTAGGTCAAATT 3'   (FIB-3)

The sequence of these probes corresponds to sequences at the 5' end of the Beta fibrinogen gene coding sequence and just 5' of the promoter region. Positive plaques are subcloned into pBluescript KS(+) (Stratagene, La Jolla, Calif.) to create pFIB-001. From pFIB-001 a 3 kb SacI-AccI fragment containing the Beta fibrinogen promoter and upstream regulatory elements is isolated and gel purified.

A set of 2 oligonucleotides (SEQ ID NO: 61–62) are designed to act as synthetic linkers to span from the AccI site (at position −51 from the Beta fibrinogen AUG initiation codon) in the 5' untranslated region of the Beta fibrinogen gene, to the NarI site within the luciferase gene in pUV102, to an SphI site for subcloning into pGEM-7Zf(+).

Oligo-1:    5'-CTACATGAAAAGGATGGATTCTTGGAGCTTCCACAAACTTA
AAACCATGGAAGACGCCAAAAACATCAAGAAAGGCCCGG3'
Oligo-2:    5'-CGCCGGGCCTTTCTTGATGTTTTTGGCGTCTTCCATGGTTT
TAAGTTTGTGGAAGCTCCAAGAATCCATCCTTTTCATGT3'

Oligo 1 is annealed to oligo 2, and the resulting linker and the gel purified SacI-AccI fragment of pFIB-001 ligated into SacI-SphI digested pGEM-7Zf(+). Correct insertion of the fragments is confirmed by restriction mapping to create pFIB-002.

An NsiI-NarI fragment of pFIB-002, containing the entire Beta fibrinogen promoter and 5' upstream regulatory elements, is gel purified and ligated into pUV102 which has been digested with PstI and NarI to generate pFIB-102. The SfiI fragment from pTKneo3 is gel purified and ligated into SfiI digested pFIB-102 to generate pFIB-106. This construct is then used to generate stable transfections of Hep G2 cells.

10/Scavenger Receptor gene

Sequence information on the Scavenger Receptor gene (Matsumoto, PNAS, 1990) was used to synthesize oligonucleotide probes (SCAV-1 to 7) in order to screen a human leukocyte genomic DNA library in EMBL-3 (Clontech, Palo Alto, Calif.) according to the supplier's instructions. The sequence of the oligonucleotide probes (SEQ ID NO: 63–69) were:

5' CCGAATTCATAAATCAGTGCTGCTTTC 3'   (SCAV-1)

5' CCGAATTCAAGAAGTATGGAGCAGTGG 3'   (SCAV-2)

5' CCGGATCCAAACACGAGGAGGTAAAG 3'   (SCAV-3)

5' CCGGATCCTTATATCATTTGCATTAGTTG 3'   (SCAV-4)

5' CCGGATCCATTTCCTTTTCCCGTGAG 3'   (SCAV-5)

5' GTATGGAGCAGTGGGATCACTTTCACAATCAACAGGAGGA 3'   (SCAV-6)

5' AGGACACTGATAGCTGCTCCGAATCTGTGAAATTTGATGC 3'   (SCAV-7)

The sequence of these probes corresponds to sequence at the 5' end of the Scavenger Receptor gene coding sequence. Underlined sequences correspond to added restriction sites. Probes SCAV-3, 4, and 5 are to the complimentary sequence. Positive plaques were obtained, including one containing a 16 kb insert. A ScaI digest of this insert produced a 3.5 kb fragment which was subcloned into pBluescript KS(+) (Stratagene, La Jolla, Calif.) to create pSCAV-001. By cutting pSCAV-001 at a unique site just 5' of the Scavenger Receptor translational initiation codon a fragment (SCAVDNA-1) containing the Scavenger Receptor promoter and about 2.8 kb of sequence containing upstream regulatory elements is isolated and gel purified.

A set of 2 oligonucleotides (Oligo-1 and oligo-2) are designed to act as synthetic linkers to span from the untranslated region of the Scavenger Receptor gene at the 3' end of SCAVDNA-1, to the NcoI site in pUV106 (the AUG of the luciferase ORF). Another set of 2 oligonucleotides (Oligo-3 and oligo-4) are designed to act as synthetic linkers from the ScaI site at the 5' end of SCAVDNA-1 to a SacI site for integration into pGEM-5Zf(+).

Oligo 1 is annealed to oligo 2, and oligo 3 is annealed to oligo 4, and the resulting pair of linkers ligated to SCAVDNA-1 and inserted into SacI-NcoI digested PGEM-5Zf(+). Correct insertion of the fragments is confirmed by restriction mapping to create pSCAV-002.

An NsiI-NcoI fragment of pSCAV-002, containing the entire Scavenger Receptor promoter and 5' upstream regulatory elements, is gel purified and ligated into pUV102 which has been digested with PstI and NcoI to generate pSCAV-102. The SfiI fragment from pTKneo3 is gel purified and ligated into SfiI digested pSCAV-102 to generate pSCAV-106. This construct is then used to generate stable transfections of THP-1 cells.

11/Granulocyte-Colony Stimulating Factor (G-CSF) gene

Information on the G-CSF upstream and coding sequences was published by Nagata et al. (110) and was used to synthesize 5 oligonucleotide probes (OL-1 to OL-5) to screen a human leukocyte genomic DNA library (Clontech, Palo Alto, Calif.) according to the supplier's instructions.

The sequences of the oligonucleotide probes (SEQ ID NO: 70–74) were:

5' GCTTTTTGTTCCAACCCCCCTGCATT 3'  (OL-1);

5' CCCTGCATTGTCTTGGACACCAAAT 3'  (OL-2);

5' GCGCTCCAGGAGAAGCTGGTGAGT 3'  (OL-3);

5' AAGCTGATGGGTGAGTGTCTTGGC 3'  (OL-4);

5' ATCAGCGGCTCAGCCTTCTT 3'  (OL-5);

The sequences of OL-1, OL-2 and OL-5 recognize the G-CSF promoter region, OL-4 recognizes the first intron/exon junction and OL-3 recognizes sequences within the second exon (110). One of the clones isolated from the leukocyte library using these oligonucleotide probes contains a 3.5 kb SalI-BamHI fragment of G-CSF genomic sequence consisting of 3.3 kb of promoter sequence and two hundred base pairs of the coding region. This fragment was inserted into the vector pGEM-7-Zf (Promega, Madison, Wis.) which had previously been digested with SalI/BamHI, resulting in the vector pJM710. pJM710 was then digested with PstI, and the resulting 1.6 kb fragment containing G-CSF upstream sequences and the first 15 bases of the G-CSF leader sequence was inserted into the PstI site of pGEM5-Luci to generate pG-Luc1. This construct was then used for transfections of 5637 human bladder carcinoma cells as described below. pGEM5-Luci had previously been constructed by inserting the XbaI/SalI fragment from pSV-Luci containing the luciferase coding sequence and the SV40 late polyadenylation signal into pGEM 5-Zf (Promega, Madison Wis.) digested with XhoI/SalI.

Figure 25:
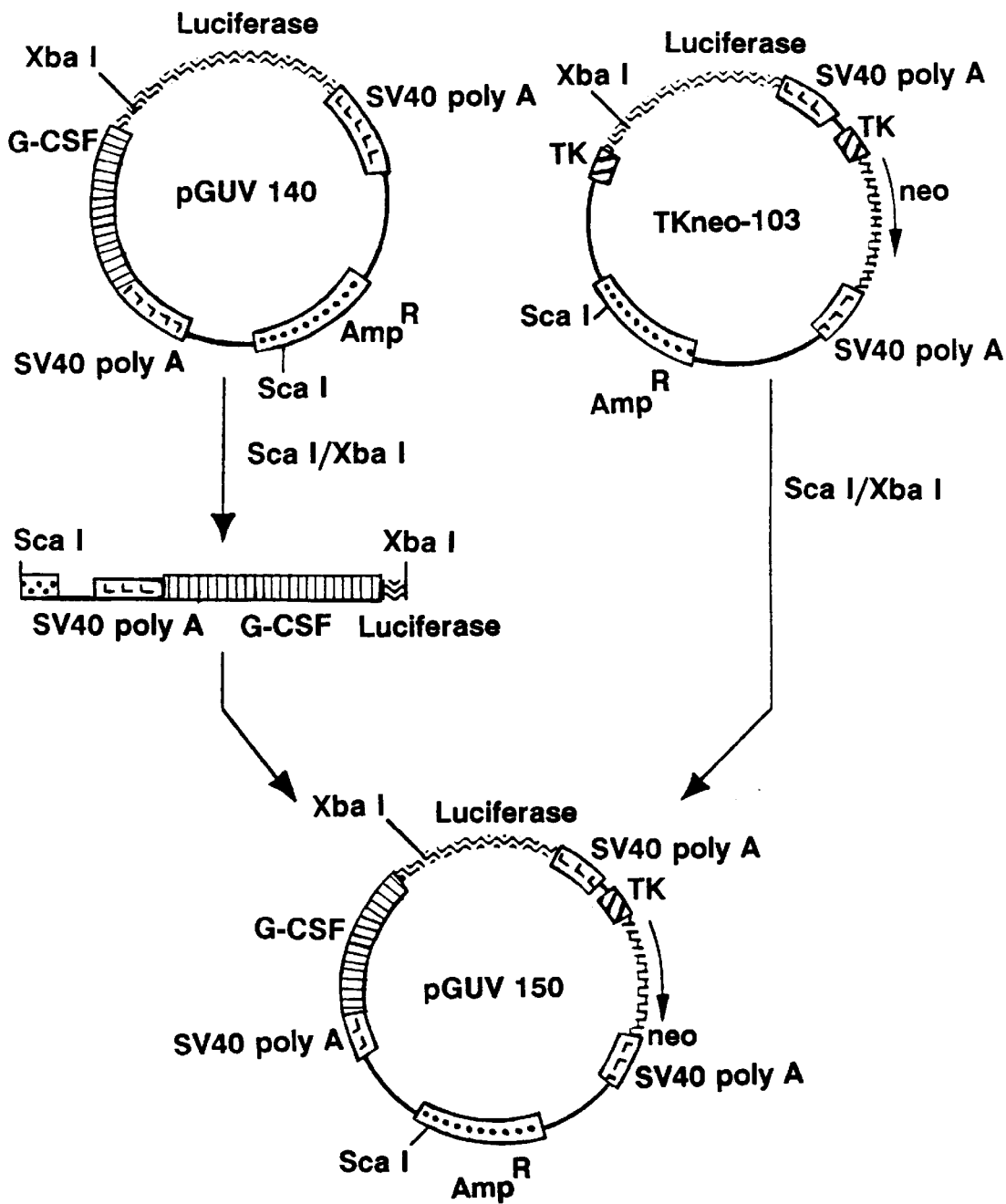
FIG. 25 is a diagrammatic representation of the construction of the plasmid pGUV150 from the ScaI/XbaI fragment from pGUV140 which contains the G-CSF-luciferase fusion and the plasmid pTKNEO-103.

In order to correctly fuse the G-CSF upstream sequences to the luciferase start codon, oligonucleotides were synthesized which contain the G-CSF leader sequence from +15 to the ATG (110), and were cloned into pUC19 to create pGUC84. The sequence of the inserted fragment was determined and was found to be as expected. The G-CSF-oligonucleotide-containing NcoI/ScaI fragment from pGUC84 was then isolated and ligated to the luciferase-containing NcoI/ScaI fragment from pUV100 to create pGUV100. Following this, the PstI fragment of the G-CSF promoter was isolated from pJM710 and inserted into the PstI site in pGUV100 generating pGUV1. The rest of the G-CSF promoter clone was added by ligating the G-CSF-luciferase containing SfiI/ScaI fragment from pGUV1 to the appropriate SfiI/ScaI fragment from pJM710, creating the plasmid pGUV2. The XbaI fragment from pGUV2 containing the G-CSF-luciferase fusion was then cloned into pUV103 previously digested with XbaI/SpeI, generating pGUV140. Finally, a TK-Neo cassette was included by ligating the ScaI/XbaI fragment from pGUv140 which contains the G-CSF-luciferase fusion into pTKNEO103 previously digested with ScaI/XbaI, yielding the final vector pGUV150 (FIG. 25).

12/Granulocyte-Macrophage Colony Stimulating Factor (GM-CSF) gene

Cloning of GM-CSF promoter sequences was performed by using oligonucleotide probes based on the GM-CSF genomic sequence (105). Two DNA oligonucleotide probes (SEQ ID NO: 75–76) were synthesized, one corresponding to GM-CSF sequences 5' of the coding region (5' GGTGAC-CACAAAATGCCAGGGAGGCGGG 3') and the other to sequences in the first exon (5' GCAGGCCACAGTGC-CCAAGAGACAG CAGCAGGCT 3'). The oligonucleotide probes were used to screen a human leukocyte cell genomic DNA library (Clontech, Palo Alto, Calif.) following the manufacturer's instructions. One clone was obtained which contains the entire GM-CSF coding region along with 2 kb of upstream sequences.

Figure 26:
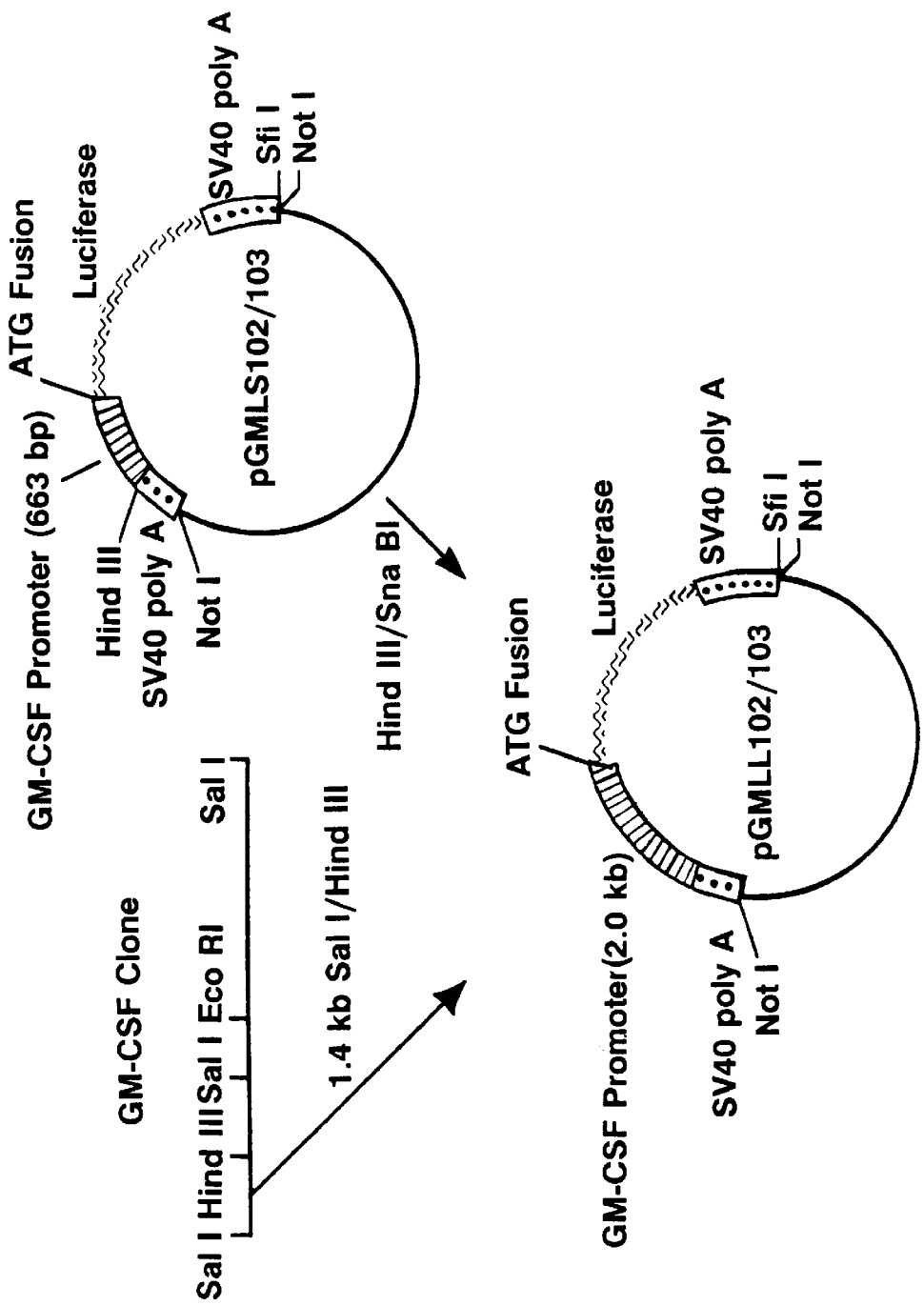
FIG. 26 is a diagrammatic representation of the construction of plasmids pGMLL102 and pGMLL103 from the plasmid pGMLS102 and the GM-CSF clone and the plasmid pGMLS103 and the GM-CSF clone, respectively.
Figure 27:
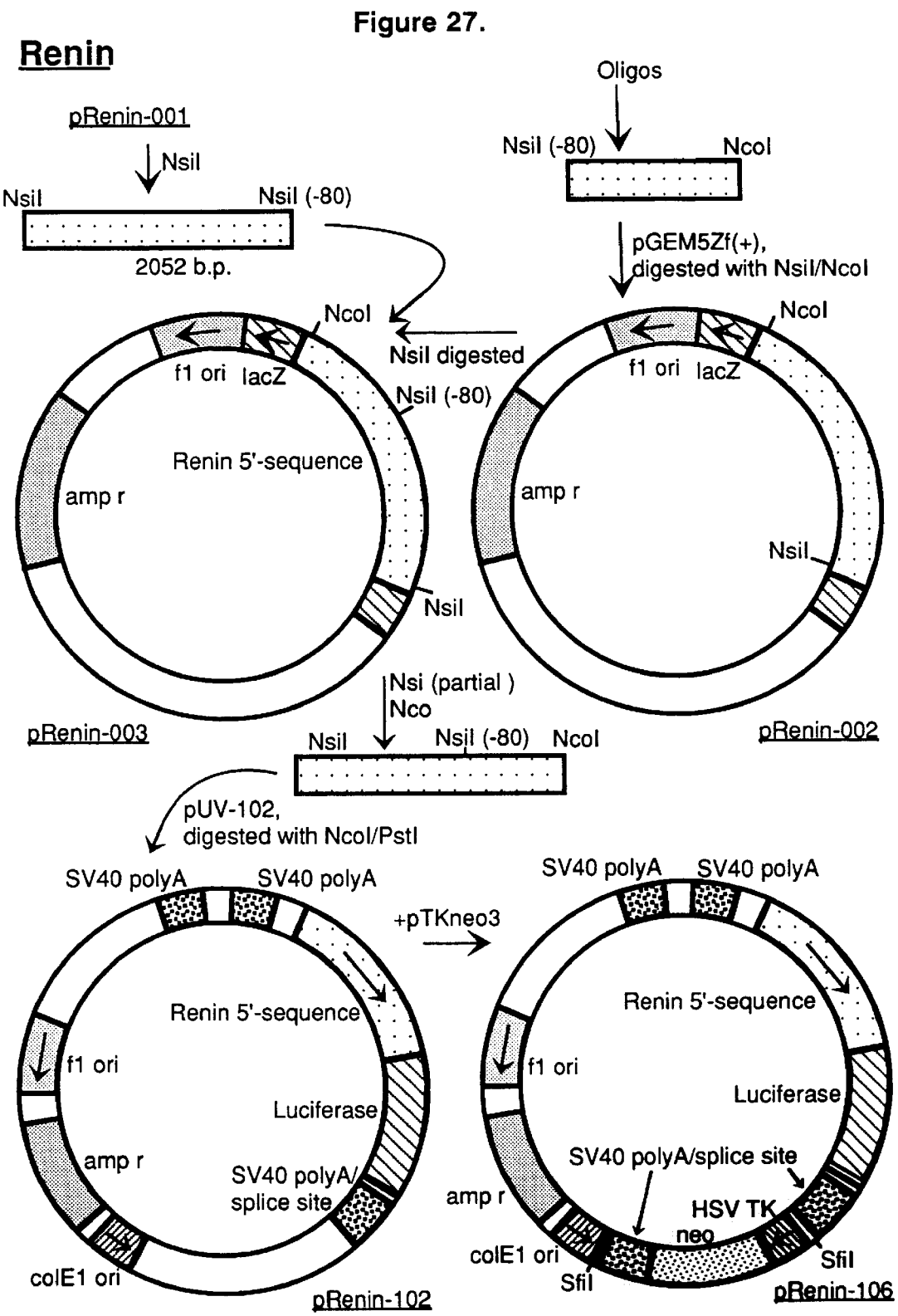
FIG. 27 shows the molecular cloning method for insertion of the regulatory and promoter elements of the renin gene into the mammalian expression shuttle vector. Details of the cloning method, including sequence information for oligonucleotide are given in section C, part 14. Numbers (–80) in parentheses refer to a restriction site 80 base pairs upstream of the renin gene translational initiation codon.*
Figure 28:
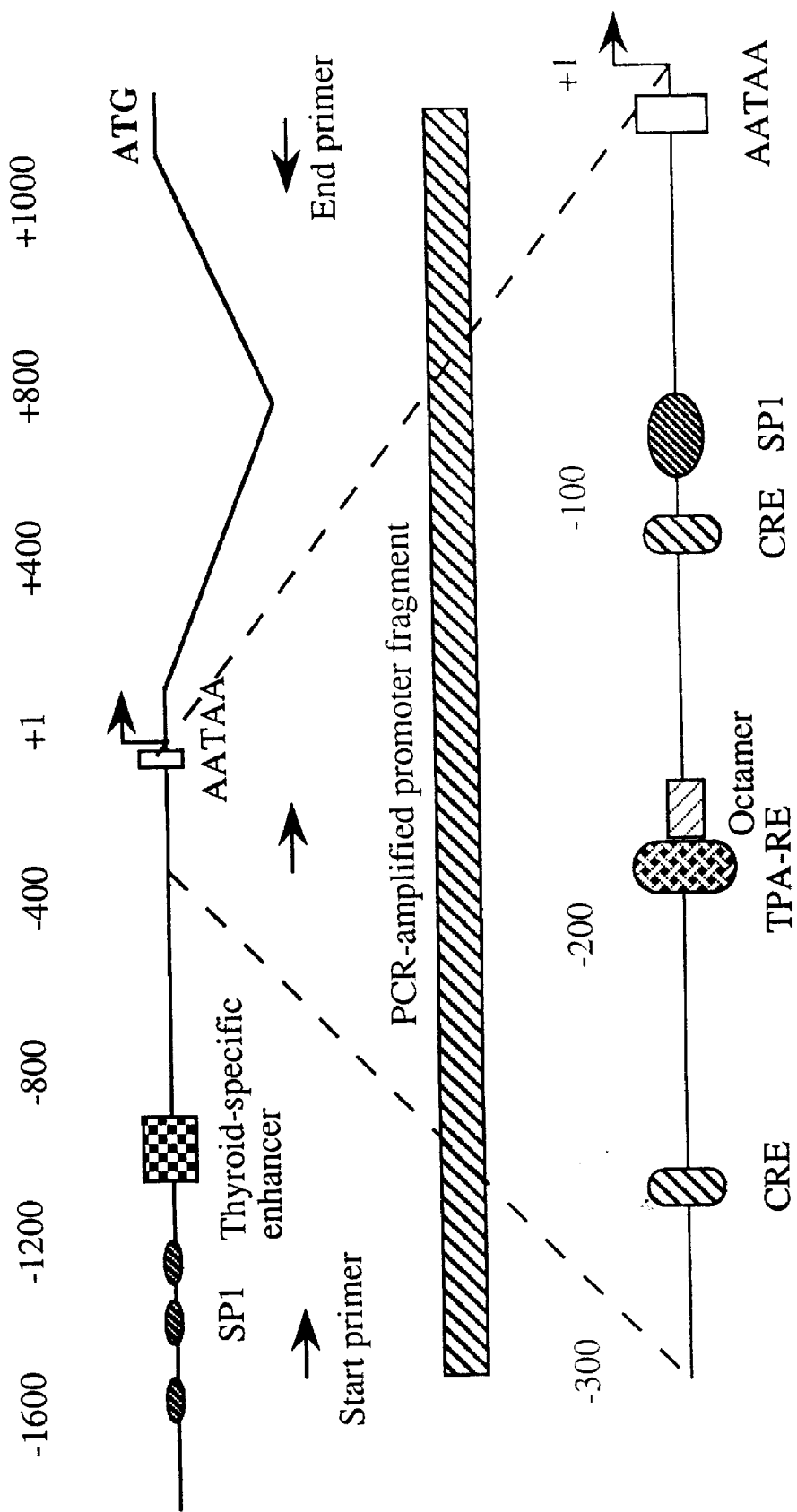
FIG. 28 shows the calcitonin C/CGRP promoter including the thyroid specific enhancer.

The about 0.7 kb HindIII/RsaI fragment of the GM-CSF clone was inserted into pUC 18 previously digested with HindIII/HincII. The about 0.7 kb HindIII/SmaI fragment was then isolated from the resulting vector and cloned into pUV 100 digested previously with HindIII/SnaBI, thereby generating pGMLUCI. In order to correctly fuse the GM-CSF ATG with the coding region of luciferase, four oligonucleotides were synthesized, phosphorylated, annealed, ligated, and inserted into pUC19 previously digested with Eco RI/XbaI, generating pGM-1. pGM-1 was then sequenced (Sequenase Kit, U.S. Biochemicals, Cleveland, Ohio) using the M13 forward (U.S. Biochem.) and reverse primers (Pharmacia, Piscataway, N.J.) to ensure that there were no mutations in the synthesized oligonucleotides. The about 1.8 kb BstEII/ScaI fragment from pGM-1 was then isolated and ligated to about 1.5 kb BstEII/ScaI fragment from pGMLUCI to generate pGM-2. pGM-2 was then digested with Hind III/XbaI and about 0.7 kb fragment was cloned into pUV 102 and pUV 103 previously digested with HindIII/XbaI. This generated pGMLS102 and pGMLS103, which contain 663 bp of GM-CSF sequence 5' of the ATG fused directly to the second (correct) ATG of luciferase and the rest of the luciferase coding region. An additional about 1.4 kb of upstream sequences were cloned into this construct by isolating the about 1.4 kb SalI/HindIII fragment from the GM-CSF clone, blunting the SalI end by filling in with Klenow polymerase, and inserting the fragment into pGMLS102 and pGMSL103 previously digested with HindIII/SnaBI. This step generated pGMLL102 and PGMLL103, respectively (FIG. 26). Finally, the pTKNEO2 and PTKNEO3 about 1.8 kb SfiI fragments were cloned directly into the SfiI site of pGMLL103 to generate pGMLL103 NEO2 and pGMLL103 NEO3.

13/Renin gene

Sequence information on the Renin gene is used to synthesize oligonucleotide probes (Renin-1 to 3)) in order to screen a human leukocyte genomic DNA library in EMBL-3 (Clontech, Palo Alto, Calif.) according to the supplier's instructions. The sequence of the oligonucleotide probes (SEQ ID NO: 77–79) are:

5'  CAGAACCTCAGTGGATCTCAGAGAGAGCCCCAGACTGAGGGAAG   3'
(Renin-1)

5'  ATGGATGGAGAAGGATGCCTCGCTGGGGACTGCTGCTGCT   3'
(Renin-2)

5'  CTGCTCTGGGGCTCCTGTACCTTTGGTCTCCCGACAGACA   3'
(Renin-3)

The sequence of these probes corresponds to sequence at the 5' untranslated and coding region of the Renin gene. Positive plaques are subcloned into pBluescript KS(+) (Stratagene, La Jolla, Calif.) to create pRenin-001.

A set of 4 oligonucleotides (SEQ ID NO: 80–83) are designed to act as synthetic linkers to span from the NsiI site (at position −80 from the Renin AUG initiation codon) in the 5' untranslated region of the Renin gene to the NcoI site in pUV106 (the AUG of the luciferase ORF).

Oligo-1: 5'-TGGAGTGTATAAAAGGGGAAGGGCTAAGGGAGCCA-3'

Oligo-2:5'-TCTGTGGCTCCCTTAGCCCTTCCCCTTTTATACACTCCATGCA-3'

Oligo-3: 5'-CAGAACCTCAGTGGATCTCAGAGAGAGCCCCAGACTGAGG
          GAAG-3'
Oligo-4:5'-CATGCTTCCCTCAGTCTGGGGCTCTCTCTGAGATCCACTGAGGT-
          3'

Oligo 1 is annealed to oligo 2, oligo 3 is annealed to oligo 4, and the resulting pair of linkers ligated into pGEM-5Zf(+) digested with NsiI and NcoI to create pRenin-002.

A NsiI fragment of pRenin-001, corresponding to Renin upstream regulatory elements is gel purified and ligated into NsiI digested pRenin-002. The correct orientation of the inserted fragment is confirmed by restriction mapping to create pRenin-003.

An NsiI-NcoI fragment of pRenin-003 (partial NsiI digest), containing the entire Renin promoter and 5' leader, is gel purified and ligated into pUV102 which has been digested with PstI and NcoI to generate pRenin-102. The SfiI fragment from pTKneo3 is gel purified and ligated into SfiI digested pRenin-102 to generate pRenin-106. This construct is then used to generate stable transfections of As4.1 cells.

/15 Calcitonin gene

Sequence information on the Calcitonin gene (101) is used to synthesize oligonucleotide probes (Calcitonin-1 and 2). A fragment containing sequence from −1483 to +1158 (101) is obtained by PCR using the following two oligonucleotide primers (SEQ ID NO: 84–85):

Calcitonin 1 (start primer) HindIII

5'-GGA GAT GGT GGA GAC GCT GAA AAG CTT CTT-3'
Calcitonin 2 (End primer)

5'GAC ACC TCT CTG CAA GGG AAG AAT GAG ATA AAC-3'

The ends the PCR-amplified fragment are blunted using T4 DNA polymerase and will be digested HindIII. This fragment is designated fragment 1.

The pUV102-luci expression vector which lacks the HSV-TKNeo transcription unit is digested with NcoI and the ends are blunted with T4 DNA polymerase. This fragment is again digested with HindIII to obtain a HindIII-blunt fragment. This fragment is designated fragment 2.

Fragment 1 is ligated with fragment 2 to obtain a calcitonin/CGRP promoter-luci fusion construct.

/16 PEPCK gene

Figure 29:
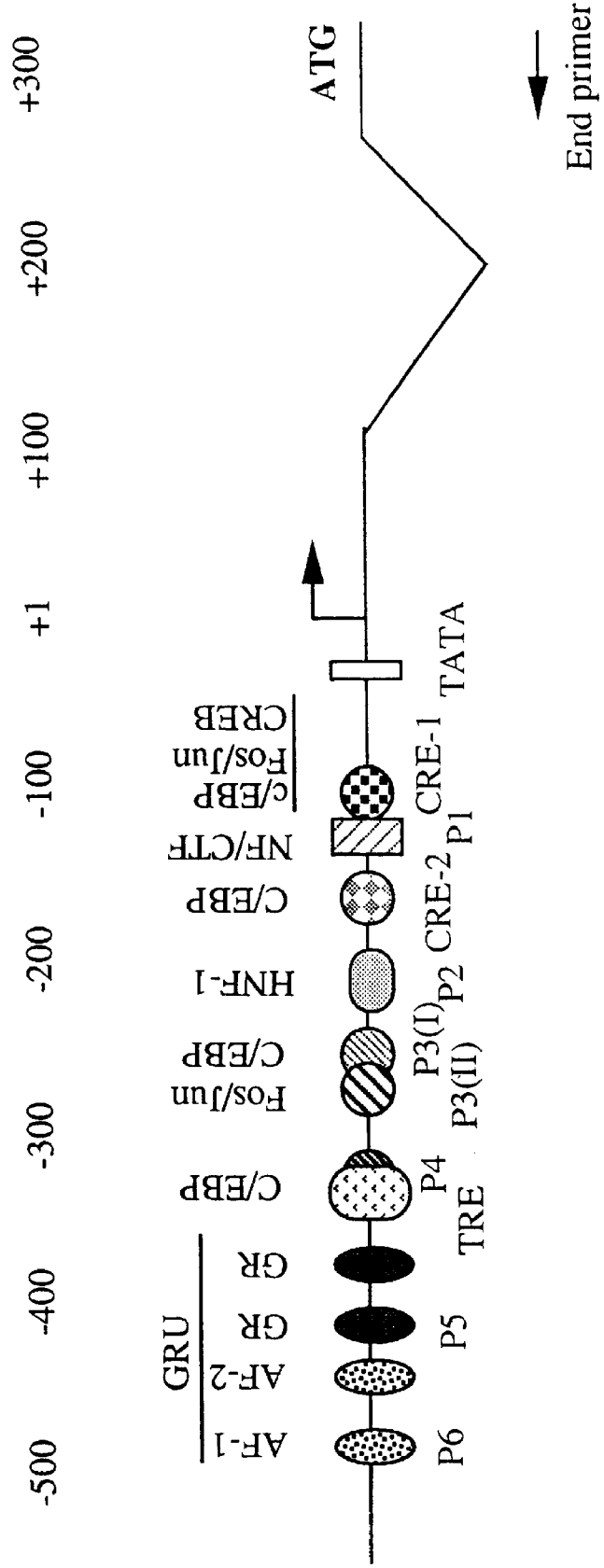
FIG. 29 shows the PEPCK promoter.
Figure 30:
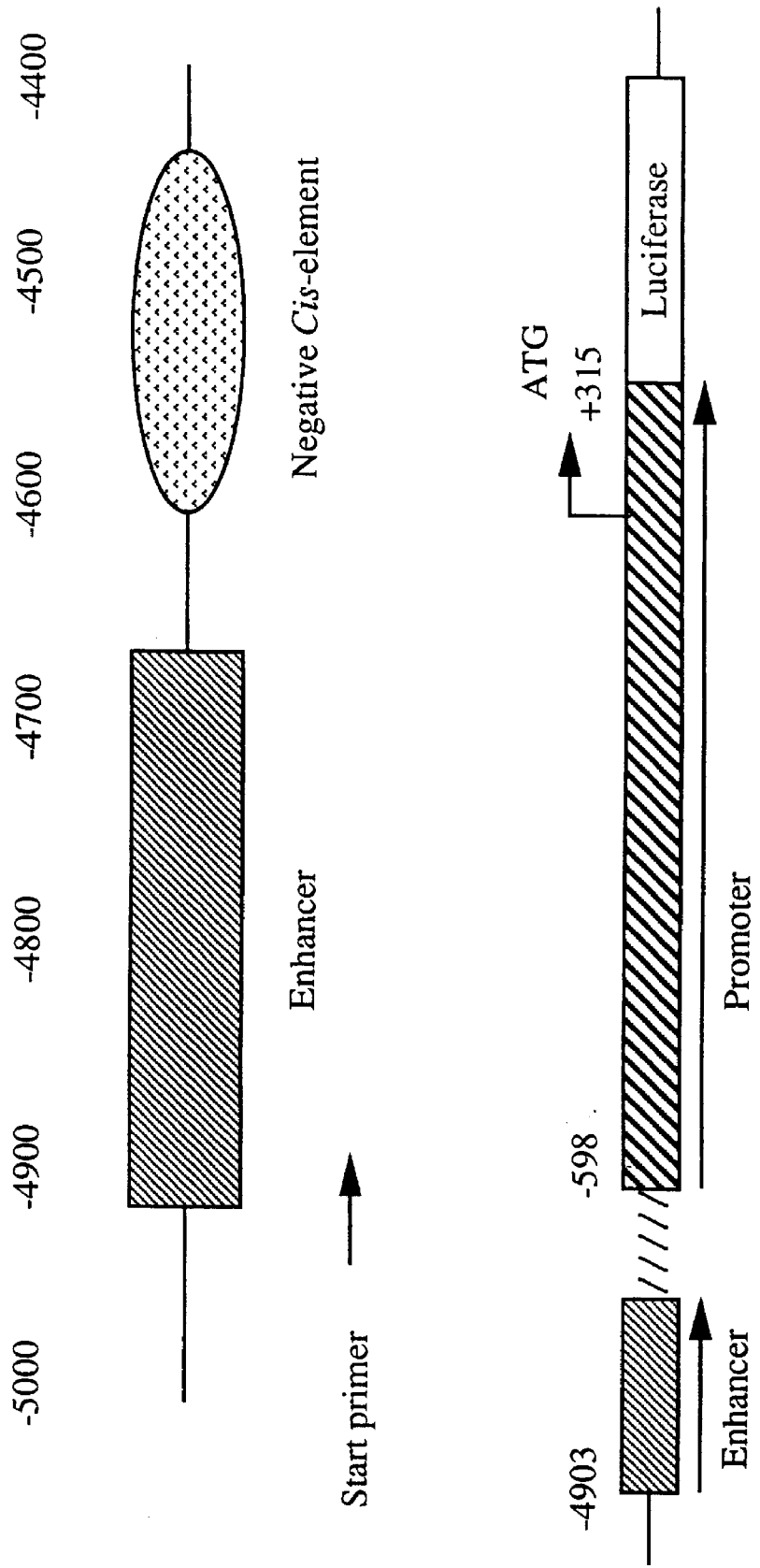
FIG. 30 shows the PEPCK enhancer, approximately 4,500 base pairs upstream from the PEPCK start site.

PEPCK promoter and the regulatory elements are well characterized and are shown in FIGS. 29 and 30. There is an intron between the transcription start site and the translation initiation codon (ATG) between +102 and +275 (6) and there is an enhancer between −4903 and −4668 (5). The promoter-fusion construct includes all the native sequence present between the transcription start site and the ATG.

A fragment containing sequence from −4927 to +315 is obtained by PCR using the following two oligonucleotide primers (SEQ ID NO: 85–86):

PEPCK-L (Start Primer)

5'-AGG CTC AGG AAC CTG GGT TTA AAA GAC TCC-3'
PEPCK-2 (End Primer)

5'TCTTGC AAT GGT GTG GAG AGA GGC AGC GAC-3'

The PCR-amplified fragment using T4 DNA polymerase. This fragment is designated Fragment 1. The pUV102-luci expression vector which lacks the HSV-TK transcription unit is digested with NcoI and the ends filled with T4 DNA polymerase to generate blunt ends. This fragment is designated Fragment 2.

Fragment 1 is ligated with Fragment 2 to obtain a PEPCK-enhancer-promoter-luci fusion construct. The clone containing the promoter-enhancer in the 5' to 3' orientation is chosen for further study.

D/REPORTER CELL LINES

Isolation of Single Cell Clones Containing Various Promoter-Luciferase Fusion Constructs and Responsiveness to Known Transcriptional Modulators

1/MMTV CONTROL 1. pMluci into NIH3T3 (MMTV control cell line)

pMluci and pSV2Neo, an antibiotic resistance plasmid (84), were co-transfected into NIH/3T3 mouse fibroblast cells using the calcium phosphate precipitation method (85) with a commercially available kit (Pharmacia, Piscataway N.J.). Two days later, cells were transferred to media containing 0.4 mg/ml G418 and were grown for an additional 10–14 days. G418-resistant clones were isolated by standard methods. Once sufficient cell numbers were obtained, clones were analyzed based on several criteria: constitutive luciferase production, induction of luciferase expression by dexamethasone (1 Am, Sigma, St. Louis, Mo.), satisfactory attachment to microtiter plates used in the high-throughput screen (see section G) and acceptable standard deviation in multiple luciferase expression assays (see below for assay protocol). This analysis was carried out using the luciferase assay conditions described above. Of the clones which satisfied the above criteria for the high throughput screen, one clone, M10, was selected for use.

2/APOLIPOPROTEIN (a)

HepG2 hepatocarcinoma cells have been previously shown to express apolipoprotein (a) (38). Hep G2 cells are transfected with 10 µg of linear pAposma106 per $10^6$ cells using electroporation. Neomycin resistant colonies are isolated and analyzed as outlined above. Factors known to modulate apolipoprotein (a) transcription are tested and the best clones selected for use in the high throughput screen.

Hela cells are also transfected with 10 µg of linear pAposma106 per $10^6$ cells in order to evaluate liver specific expression. This is evaluated in transient transfectants using a co-transfected β-galactosidase vector to control for transfection efficiency.

Modulation of apolipoprotein (a) expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous apolipoprotein (a) gene expression is also determined. This is done by northern blot analysis and/or quantitative PCR analysis of mRNA. When screening for novel compounds these same procedures are utilized to investigate the specificity of a transcriptional modulator. Two dimensional protein gels are also utilized for this purpose, $^{35}$S-labelled amino acids being used to monitor protein levels. Immunoblotting with specific apolipoprotein (a) peptide antibodies is used to identify the position of apolipoprotein (a) on the gels. These are prepared using standard techniques.

3/APOLIPOPROTEIN AI

HepG2 hepatocarcinoma cells have been previously shown to express apolipoprotein AI (71, 86). Hep G2 cells are transfected with 10 µg of linear pApoAI-106 per $10^6$ cells using electroporation. Neomycin resistant colonies are isolated and analyzed as outlined above. Factors known to modulate apolipoprotein AI transcription (estrogen, testosterone, cholesterol, thyroid hormone (54) are tested and the best clones selected for use in the high throughput screen.

Previous studies (71, 86) have demonstrated that the −222 to −110 region (relative to the transcription start site +1) of the apolipoprotein AI gene functions as a powerful hepatocyte-specific transcriptional enhancer. Hela cells are also transfected with 10 µg of linear pApoAI-106 per $10^6$ cells in order to evaluate liver specific expression. This is evaluated in transient transfectants using a co-transfected β-galactosidase vector to control for transfection efficiency.

Modulation of apolipoprotein AI expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous apolipoprotein AI gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific apolipoprotein AI peptide antibodies is used to identify the position of apolipoprotein AI on the gels. These are prepared using standard techniques.

4/APOLIPOPROTEIN B

HepG2 hepatocarcinoma cells have been previously shown to express apolipoprotein B (102). Hep G2 cells are transfected with 10 µg of linear pApoB-106 per $10^6$ cells using electroporation. Neomycin resistant colonies are isolated and analyzed as outlined above. Factors known to modulate apolipoprotein B transcription are tested and the best clones selected for use in the high throughput screen.

Previous studies (102) have demonstrated that the −128 to −70 region (relative to the transcription start site +1) of the apolipoprotein B gene contains two cis-acting regulatory regions which control hepatocyte-specific expression. Hela cells are transfected with 10 µg of linear pApoB-106 per $10^6$ cells in order to evaluate liver specific expression. This is evaluated in transient transfectants using a co-transfected β-galactosidase vector to control for transfection efficiency.

Modulation of apolipoprotein B expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous apolipoprotein B gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific apolipoprotein B peptide antibodies is used to identify the position of apolipoprotein B on the gels. These are prepared using standard techniques.

5/LDL-RECEPTOR

HepG2 hepatocarcinoma cells have been previously shown to express LDL receptor (103). Hep G2 cells are transfected with 10 μg of linear pLDL-106 per $10^6$ cells using electroporation. Neomycin resistant colonies are isolated and analyzed as outlined above. Factors known to modulate LDL receptor transcription (e.g. sterols such as cholesterol (40)) are tested and the best clones selected for use in the high throughput screen. Previous studies (40) have demonstrated that the −53 to −68 region (relative to the transcription start site +1) of the LDL receptor gene contains a sterol responsive element which functions in an orientation-independent manner, and when inactivated by sterols acts as a feedback control mechanism.

Modulation of LDL receptor expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous LDL receptor gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific LDL receptor peptide antibodies is used to identify the position of LDL receptor on the gels. These are prepared using standard techniques.

6/CHOLESTEROL 7α-HYDROXYLASE

HepG2 hepatocarcinoma cells are used to express cholesterol 7α-hydroxylase since this gene is normally expressed in the liver. They are transfected with 10 μg of linear pCH-106 per $10^6$ cells using electroporation. Neomycin resistant colonies are isolated and analyzed as outlined above. Factors known to modulate cholesterol 7α-hydroxylase transcription (e. g. bile salts, sterols such as cholesterol (104)) are tested and the best clones selected for use in the high throughput screen.

Modulation of cholesterol 7α-hydroxylase expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous cholesterol 7α-hydroxylase gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific cholesterol 7α-hydroxylase peptide antibodies is used to identify the position of cholesterol 7α-hydroxylase on the gels. These are prepared using standard techniques.

7/VEGF

Human monoblast U937 cells are known to express VEGF (105). They are transfected with 10 μg of linear pVEGF-106 per $10^6$ cells using electroporation. Neomycin resistant colonies are isolated and analyzed as outlined above. Factors which should modulate VEGF transcription (e.g. TPA, forskolin or dibutyryl cAMP, and compounds which elicit a heat shock response (42)) are tested and the best clones selected for use in the high throughput screen. Human promyelocytic leukemia HL-60 cells and human vulval epidermoid carcinoma A431 cells are also capable of producing VEGF (106, 107). Stable transfectants are also prepared from these for screening in a different cellular background. There may be multiple closely related VEGF genes (105, 107), and it is not known whether one or all of them are regulated differently in different cell types.

Modulation of VEGF expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous VEGF gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific VEGF peptide antibodies is used to identify the position of VEGF on the gels. These are prepared using standard techniques.

8/CSF-1

Figure 21:
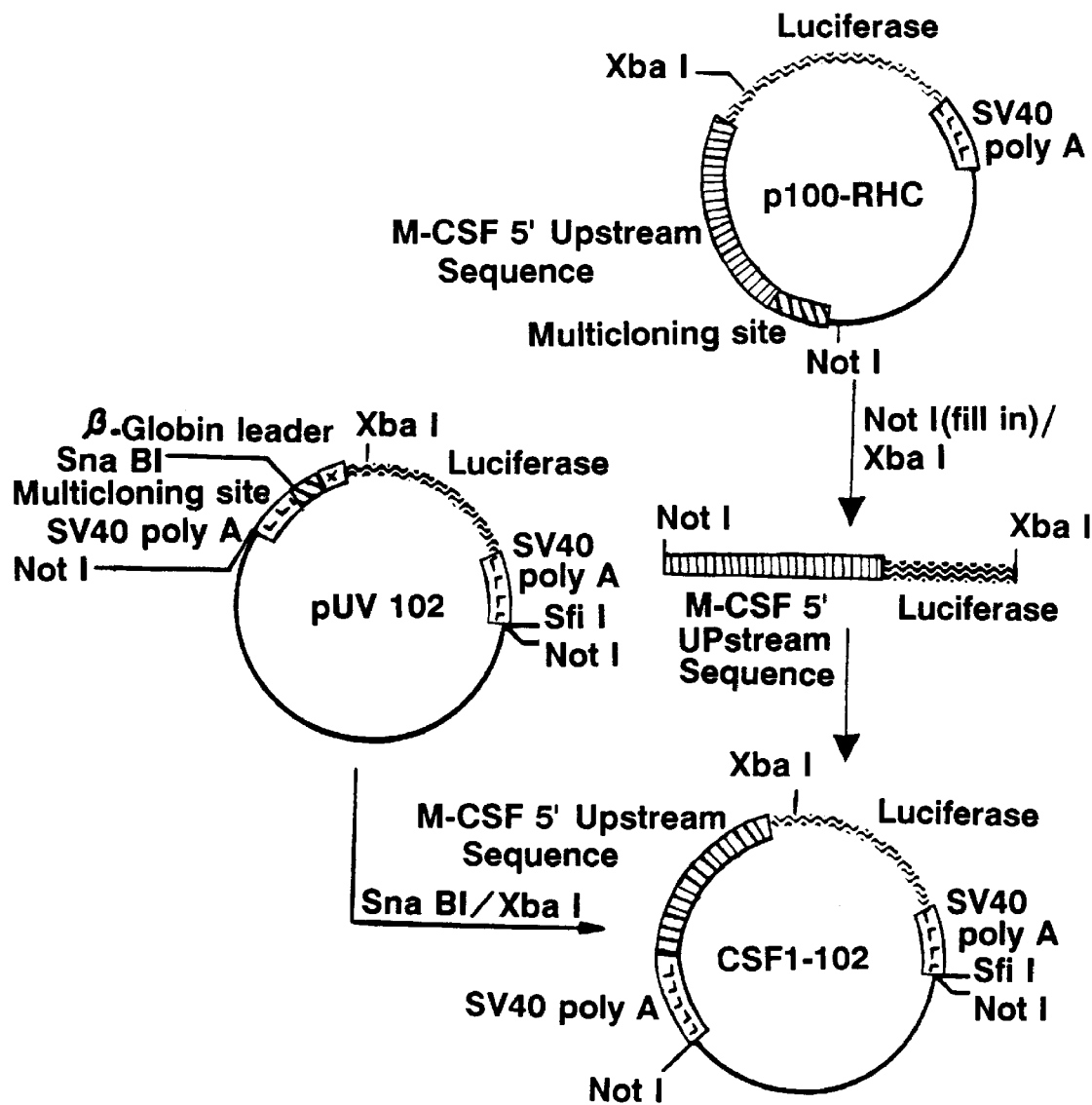
FIG. 21 is a diagrammatic representation of the construction of plasmid pCSF1-102, the M-CSF reporter vector.
Figure 22:
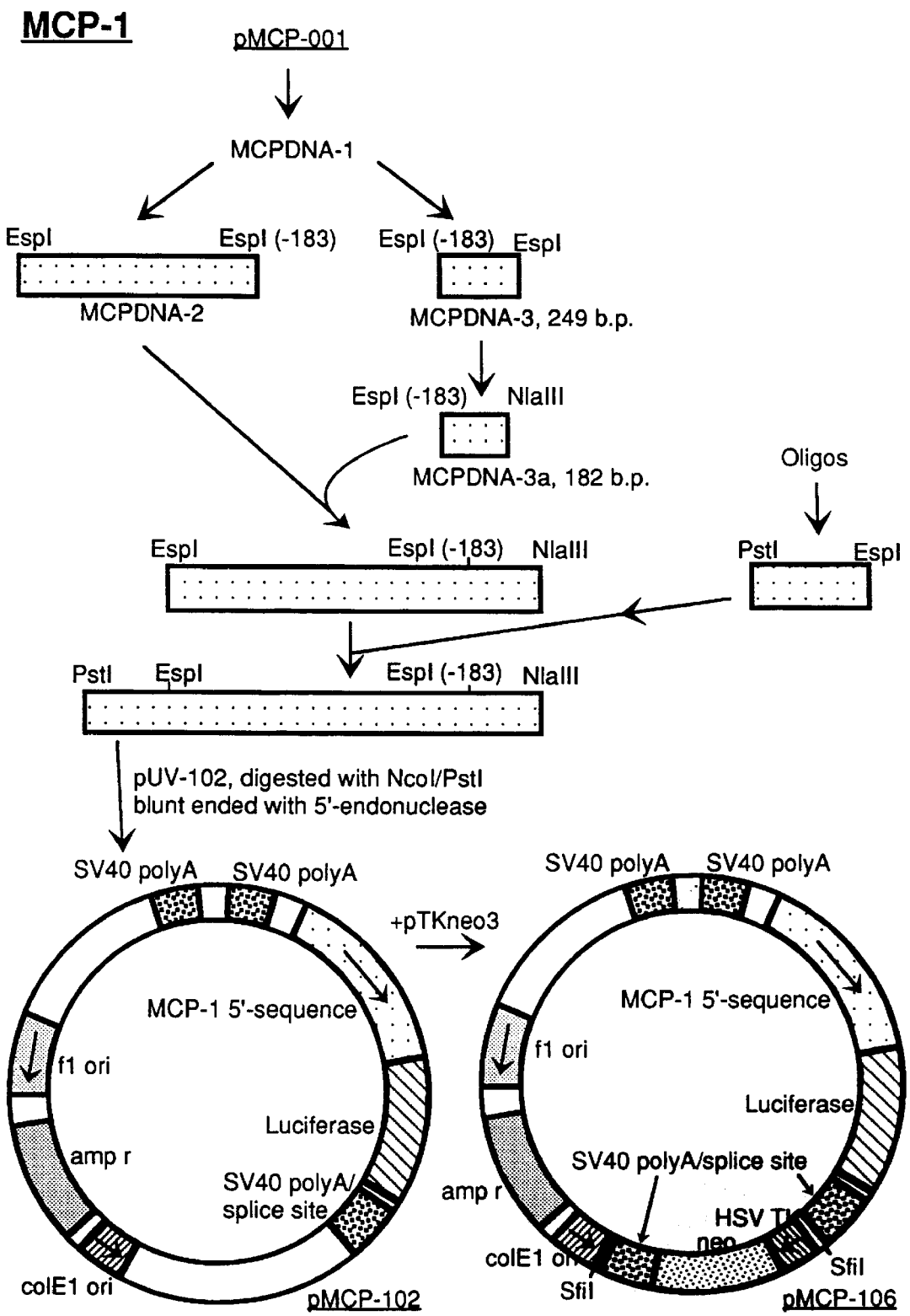
FIG. 22 shows the molecular cloning method for insertion of the regulatory and promoter elements of the MCP-1 gene into the mammalian expression shuttle vector. Details of the cloning method, including sequence information for oligonucleotide, are given in section C, part 8. Numbers (–183) in parentheses refer to a restriction site 183 base pairs upstream of the MCP-1 gene translational initiation codon.*
Figure 23:
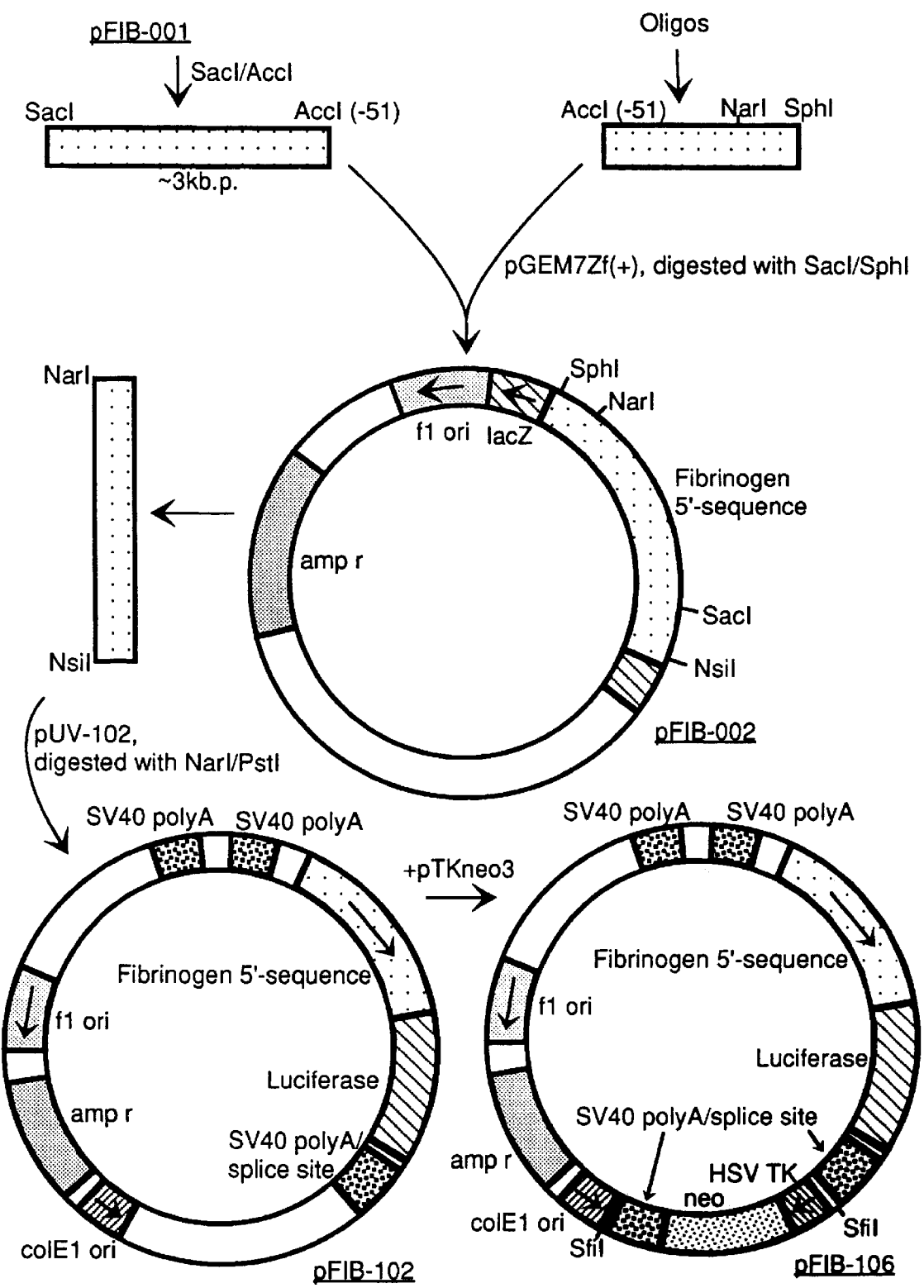
FIG. 23 shows the molecular cloning method for insertion of the regulatory and promoter elements of the β-fibrinogen gene into the mammalian expression shuttle vector. Details of the cloning method, including sequence information for oligonucleotide, are given in section C, part 9. Numbers (–51) in parentheses refer to a restriction site 51 base pairs upstream of the β-fibrinogen gene translational initiation codon.*
Figure 24:
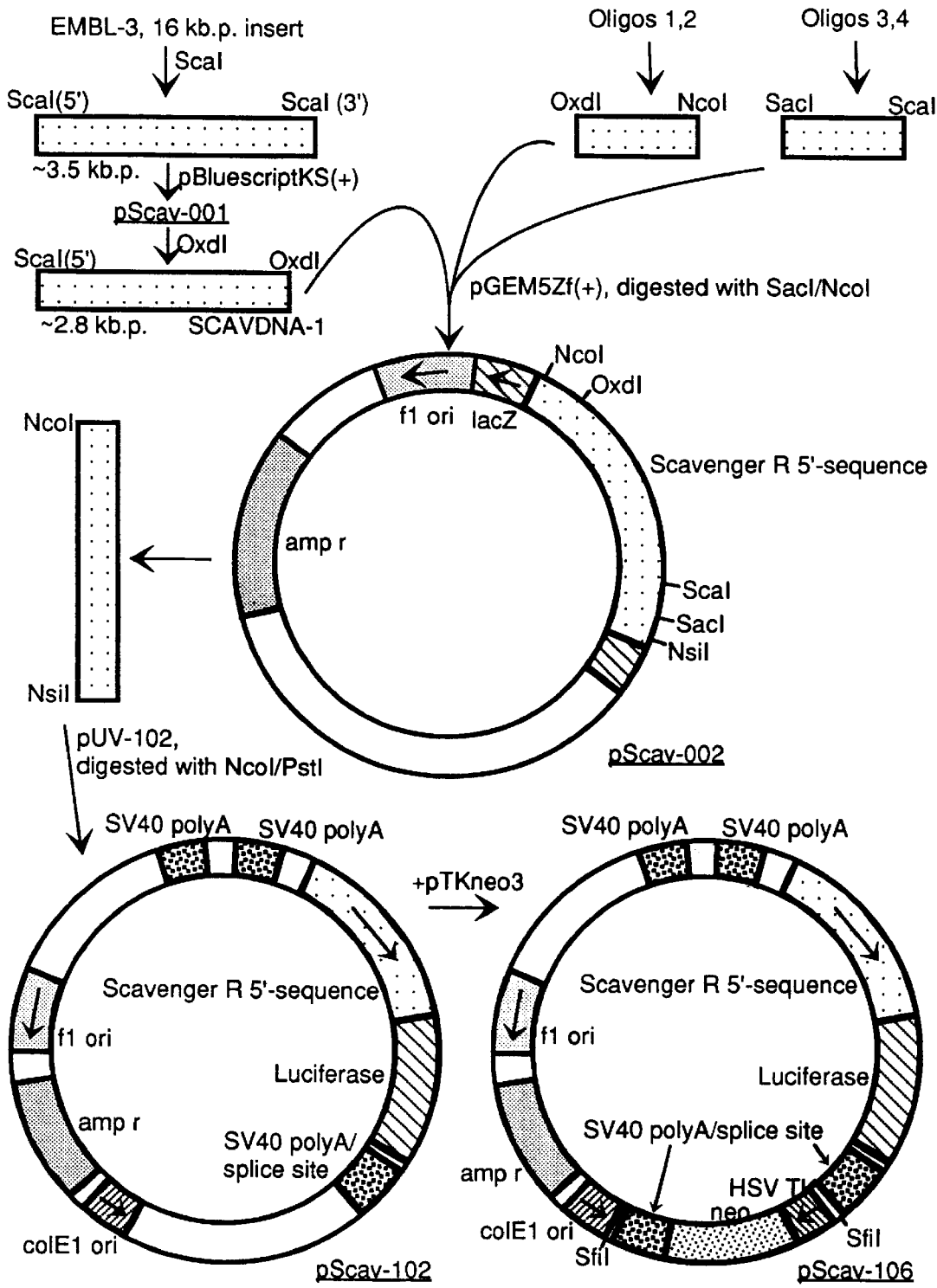
FIG. 24 shows the molecular cloning method for insertion of the regulatory and promoter elements of the scavenger receptor gene into the mammalian expression shuttle vector. Details of the cloning method, including sequence information for oligonucleotide, are given in section C, part 10.*

Human promyelocytic leukemia HL-60 cells are known to express CSF-1 (74). They were transfected with linearized pCSF1-102 (FIG. 21) and linearized PTKneo3 using electroporation as described above. Three neomycin resistant clones were generated: —M2071, M2085 and M2086. All three responded to a 16 hour incubation with 2000 units/ml interferon-gamma by a 20-fold increase of luciferase expression. M2086 was selected for use in the high throughput screen. The WI-38 human fibroblast cell line is also capable of producing CSF-1. Stable transfectants are also prepared from these for screening in a different cellular background. There is evidence for tissue-specific modulation of CSF-1 gene expression, and since the major source of the CSF-1 which stimulates the growth of macrophages at atherosclerotic plaques is unknown, screening with more than one cell line may be useful.

Modulation of CSF-1 expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous CSF-1 gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific CSF-1 peptide antibodies is used to identify the position of CSF-1 on the gels. These are prepared using standard techniques.

9/MCP-1

Human WI-38 fibroblastic cells are known to express MCP-1 (90). They are transfected with 10 μg of linear pMCP-106 per $10^6$ cells using electroporation. Neomycin resistant colonies are isolated and analyzed as outlined above. Factors which should modulate MCP-1 transcription (e.g. Minimally-modified LDL, interferon-gamma, TNF-alpha, interleukin-1, or phorbol esters (e.g. PMA) (75)) are tested and the best clones selected for use in the high throughput screen.

Modulation of MCP-1 expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous MCP-1 gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific MCP-1 peptide antibodies is used to identify the position of MCP-1 on the gels. These are prepared using standard techniques.

10/FIBRINOGEN, β-SUBUNIT

HepG2 hepatocarcinoma cells have been previously shown to express fibrinogen β-subunit (76). They are transfected with 10 μg of linear pFIB-106 per $10^6$ cells using electroporation. Neomycin resistant colonies are isolated and analyzed as outlined above. Factors which should modulate fibrinogen β-subunit transcription (e.g. dexamethasone, IL-6 (76)) are tested and the best clones selected for use in the high throughput screen.

Modulation of fibrinogen β-subunit expression by compounds which have already been characterized, or growth factors, serves both as a control when searching for novel gene expression modulators, as well as allowing comparison between the transcriptional regulation of the. endogenous and reporter genes. When a cell line and construct displaying the appropriate luciferase activity response to the above substances is obtained, changes in the endogenous fibrinogen β-subunit gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific fibrinogen β-subunit peptide antibodies is used to identify the position of fibrinogen β-subunit on the gels. These are prepared using standard techniques.

Previous studies (76) have demonstrated that the −150 to +1 region (relative to the transcription start site +1) of the fibrinogen β-subunit gene is responsible for its hepatocyte-specific transcription. Hela cells are also transfected with 10 μg of linear pFIB-106 per $10^6$ cells in order to evaluate liver specific expression. This is evaluated in transient transfectants using a co-transfected β-galactosidase vector to control for transfection efficiency.

11/SCAVENGER RECEPTOR

THP-1 human monocytic cells have been previously shown to express scavenger receptor (41). They are transfected with 10 μg of linear pSCAV-106 per $10^6$ cells using electroporation. Neomycin resistant colonies are isolated and analyzed as outlined above. Factors which should modulate scavenger receptor transcription (e.g. PMA, TGF-b, IL-1 (41, 108)) are tested and the best clones selected for use in the high throughput screen.

Modulation of scavenger receptor expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous scavenger receptor gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific scavenger receptor peptide antibodies is used to identify the position of scavenger receptor on the gels. These are prepared using standard techniques.

12/G-CSF

A. pG-LUC1 (First G-CSF Cell Line)

pG-LUC1 and pRSVNeo were co-transfected using the Calcium phosphate method into 5637 human bladder carcinoma cells as described above. Analysis of G418 resistant cell clones was performed as above except that a known inducer of G-CSF expression (1–5 μg/ml lipopolysaccharide (LPS), *E. coli* serotype 055:b5, Difco, Detroit, Mich. or Sigma, St. Louis, Mo.) was used in place of dexamethasone. One clone, G21, was selected for use.

B. pGVU150 and pGVU140/pTKNEO3 (Second and Third Generation G-CSF Cell Lines

U5637 bladder carcinoma cells were transfected with pGVU150 (FIG. 21) or pGVU140 plus pTKNeo3 either by electroporation using a BRL (Gaithersburg, Md.) Cellporator electroporation device or by lipofection using BRL lipofectin and following the manufacturer's protocol. Clones were analyzed for luciferase expression and those testing positive expanded further and frozen in liquid nitrogen. Further analysis of 6 clones (G1002, G2005, G2071, G2085, G3014, G3031) included Southern blotting, reaction to known inducers, satisfactory attachment to microtiter plates and acceptable standard deviation in multiple luciferase expression assays. Clone G1002 was selected for use in the high throughput screen.

13/GM-CSF 6 clones generated by electroporation of U5637 cells with pGMLL103 NEO3 (FIG. 26) were subjected to further analysis as described above for G-CSF: —GM1073 (10 μg; circular); GM1081, GM1088 and GM1090 (5 μg; linear); and GM1098 and GM1105 (10 μg; linear). Clone GM1073 was selected for use in the high throughput screen.

14/Renin gene

As4.1 juxtaglomerular smooth muscle cells have been previously shown to express renin (109). As4.1 cells are transfected with 10 μg of linear pRenin-106 per $10^6$ cells using electroporation. Neomycin resistant colonies are isolated and analyzed as outlined above. Factors known to modulate renin transcription (PMA, forskolin, A23187) (80) are tested and the best clones selected for use in the high throughput screen.

Transcription of the renin gene exhibits tissue specificity, with the kidney being the major producer. Thus, Hela cells are also transfected with 10 μg of linear pRenin-106 per $10^6$ cells in order to evaluate kidney specific expression. This is evaluated in transient transfectants using a co-transfected β-galactosidase vector to control for transfection efficiency.

Modulation of renin expression by compounds which have already been characterized, or growth factors, serves both as a control when searching for novel gene expression modulators, as well as allowing comparison between the transcriptional regulation of the endogenous and reporter genes. When a cell line and construct displaying the appropriate luciferase activity response to the above substances is obtained, changes in the endogenous renin gene expression is also determined. This is done by northern blot analysis and/or quantitative PCR analysis of mRNA. When screening for novel compounds these same procedures are utilised to investigate the specificity of a transcriptional modulator. Two dimensional protein gels are also utilized for this purpose, $^{35}$S-labelled amino acids being used to monitor protein levels. Immunoblotting with specific renin peptide antibodies is used to identify the position of renin on the gels. These are prepared using standard techniques.

Validation of the Colony Stimulating Factor Reporter Cell Lines

Cell clones transfected with the mammalian expression shuttle vector fused to the G-CSF, GM-CSF and M-CSF promoters were analyzed for correct and complete integration of the promoter/luciferase constructs by Southern blotting.

Figure 31:
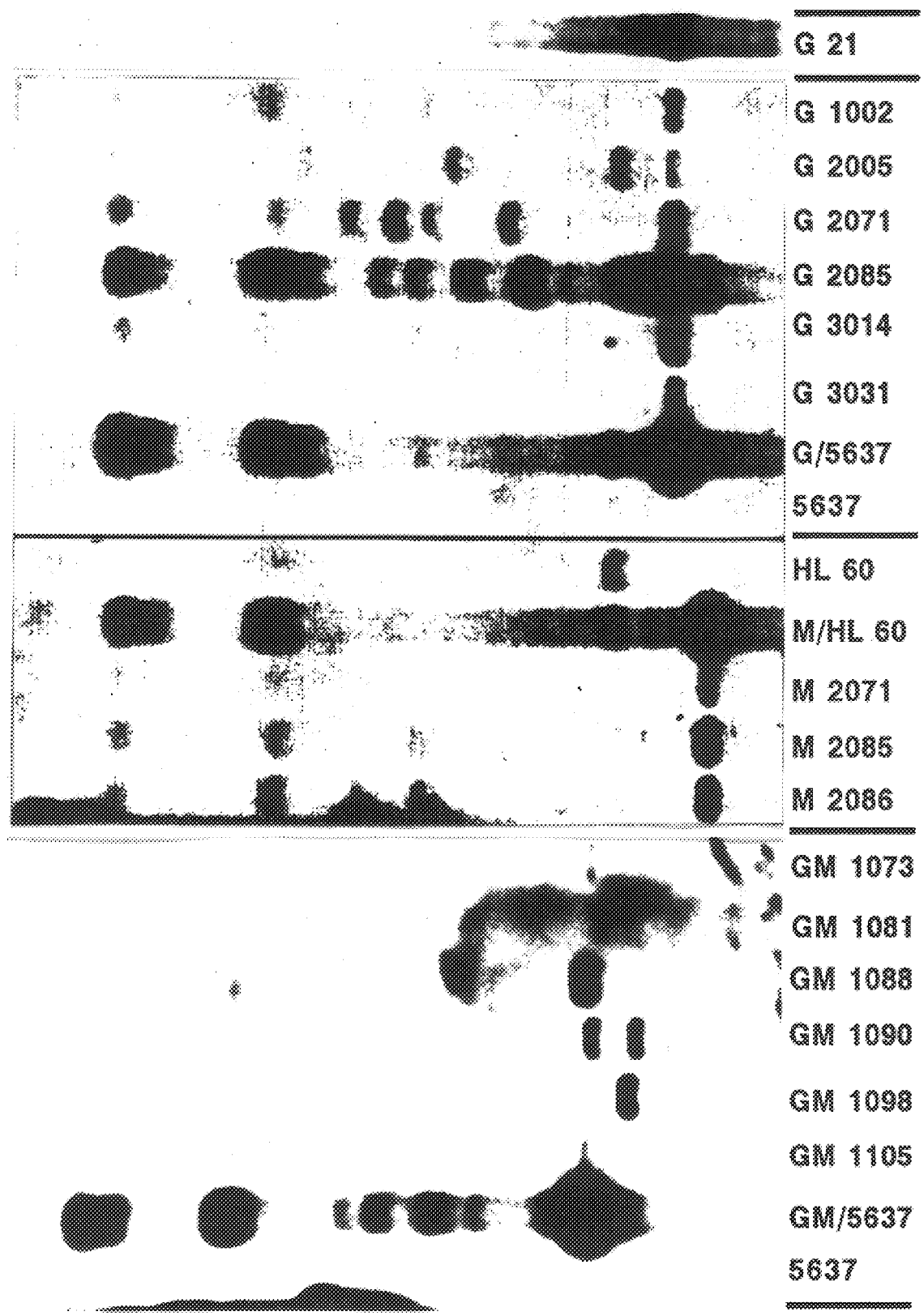
FIG. 31 is an autoradiograph of a Southern blot illustrating the correct integration of luciferase fusion constructs containing the G-CSF, M-CSF and GM-CSF promoters, respectively, into the genomes of 5637 cells (G- and GM-CSF) and HL 60 cells (M-CSF). Lanes designated 5637 and HL 60 had been loaded with DNA preparations from the parental cell lines not containing the luciferase constructs (negative controls). Lanes labeled G/5637, GM/5637 and M/HL 60 had been loaded with the same DNA preparations with the addition of the purified plasmid preparations, which had been used for the original transfections (positive controls). The two low-molecular-weight bands appearing in almost all lanes except for the negative control lanes are derived from non-specific cross-hybridizing sequences contained in the probe.

As shown in FIG. 31, G-CSF clones G1002, G3014 and G3031, GM-CSF clones GM1073, GM1088 and GM1105 and all 3 M-CSF clones tested contained only a single fragment with the correct molecular size (uppermost fragments in plasmid controls G/5637, M/HL60 and GM/5637 generated by loading mixtures of the purified plasmids and extracts of the parental cell lines 5637 or HL60 on the gel). The 2 smaller fragments are non-specific, cross-hybridizing probe impurities. The other clones all contained additional rearranged fragments of various molecular sizes. Conspicuously, all 3 G-CSF clones with correctly integrated promoter/reporter constructs were derived from electroporation, whereas the other G-CSF cell clones analyzed were obtained either by lipofection (G2005, G2071 and G2085) or calcium phosphate precipitation (G21). G21 cells contain multiple copies of the promoter/luciferase construct, the majority of which migrate at approximately correct molecular weight. The data suggest that electroporation under the optimized conditions described is the transfection method of choice to obtain cell clones with correctly integrated, complete promoter/luciferase reporter constructs.

Cell clones with correctly integrated promoter/reporter constructs were analyzed for correct reaction to known transcriptional inducers. Of the G-CSF clones tested, G1002 showed the most consistent levels of induction after 10.5 hours of incubation in serum-containing media with 8.3 ng/ml tumor necrosis factor-alpha (TNF-alpha; 2 fold), 20 ng/ml phorbol-myristate-acetate (PMA; 4.4 fold), 0.5 ng/ml Interleukin-1 beta (2.6 fold), a mixture of 4.2 ng/ml TNF-alpha and 0.3 ng/ml Interleukin-1 beta (3.8 fold) and a mixture of 4.2 ng/ml TNF-alpha and 10 ng/ml PMA (7.6 fold). Both TNF-alpha and PMA induction levels of clone G1002 were influenced by the presence or absence of epidermal growth factor (EGF). 7-Hour incubations in serum-free defined media with 20 ng/ml EGF resulted in a 3 fold G-CSF promoter induction by TNF-alpha versus 4 fold in the absence of EGF. The 9.3 fold induction by PMA in the absence of EGF was reduced to 5.6 fold by including EGF in the serum-free incubation mixture. Similar differences were observed, when EGF was substituted by 10% fetal calf serum.

A 7-hour incubation of G21 cells with PMA in serum-free media increased luciferase expression directed by the G-CSF promoter by 34.6 fold in the absence and by 24.6 fold in the presence of EGF. TNF-Alpha induction did not significantly change on EGF addition (2.8 fold with and 2.1 fold without EGF).

Promoter induction experiments were also conducted with the GM-CSF reporter cell lines GM1073, GM1088 and GM1105, which were all shown to contain correctly inserted constructs (see above). 10.5 hours incubation of GM 1073 cells with 20 ng/ml PMA in serum-containing media resulted in a 3.4 fold induction of the GM-CSF promoter, which was increased to 7.5 fold in serum-free media. Luciferase expression of clones GM1088 and GM1105 was induced by PMA 2.8 fold and 2 fold, respectively, while TNF-alpha induced both clones 2 fold. All three M-CSF clones responded to a 16-hour incubation with 2,000 units/ml Interferon-gamma by a 20-fold increase of luciferase expression from the M-CSF promoter.

All 3 GM-CSF clones described above attached to the well surfaces of microtiter plates after overnight incubation. Levels of luciferase expression from clone 1105 were not appreciably affected by the omission of the fibronectin-coating step before cell plating. Luciferase expression levels were strongly increased by fibronectin coating, however, when clones G1002 or G21 were used (about 8 fold or 3 fold, respectively).

Clones GM1088, GM1073 and G1002 consistently produced bioluminescence signals varying by less than 10% between wells, when multiple 96-well microtiter plates containing these cells were assayed.

To be able to screen large random collections of compounds it may be necessary to use a variety of solvents to account for different solubilities of the compounds of interest. The effect of three organic solvents, DMSO, methanol and ethanol, which are frequently used to dissolve screening samples, was therefore determined on three reporter cell lines.

Cells of the lines G2005, GM1105 and M10 containing luciferase reporter constructs for the G-CSF, GM-CSF or the promoter of the mouse mammary tumor virus were seeded into 96 well microtiter plates (10,000 cells/well) and cultured overnight. Various amounts of DMSO, methanol or ethanol were added to cultures. Luciferase activity in the cells was determined 8 hours after addition of the solvents. The relative amount of luciferase activity compared to untreated controls is plotted versus solvent concentration (FIGS. 32A–32C).

G2005 and GM1105, which were constructed using the same parental cell line show very similar behavior. A final concentration of 1% can be used in each case.

In vivo signal half-life of the luciferase reporter system

Figure 33:
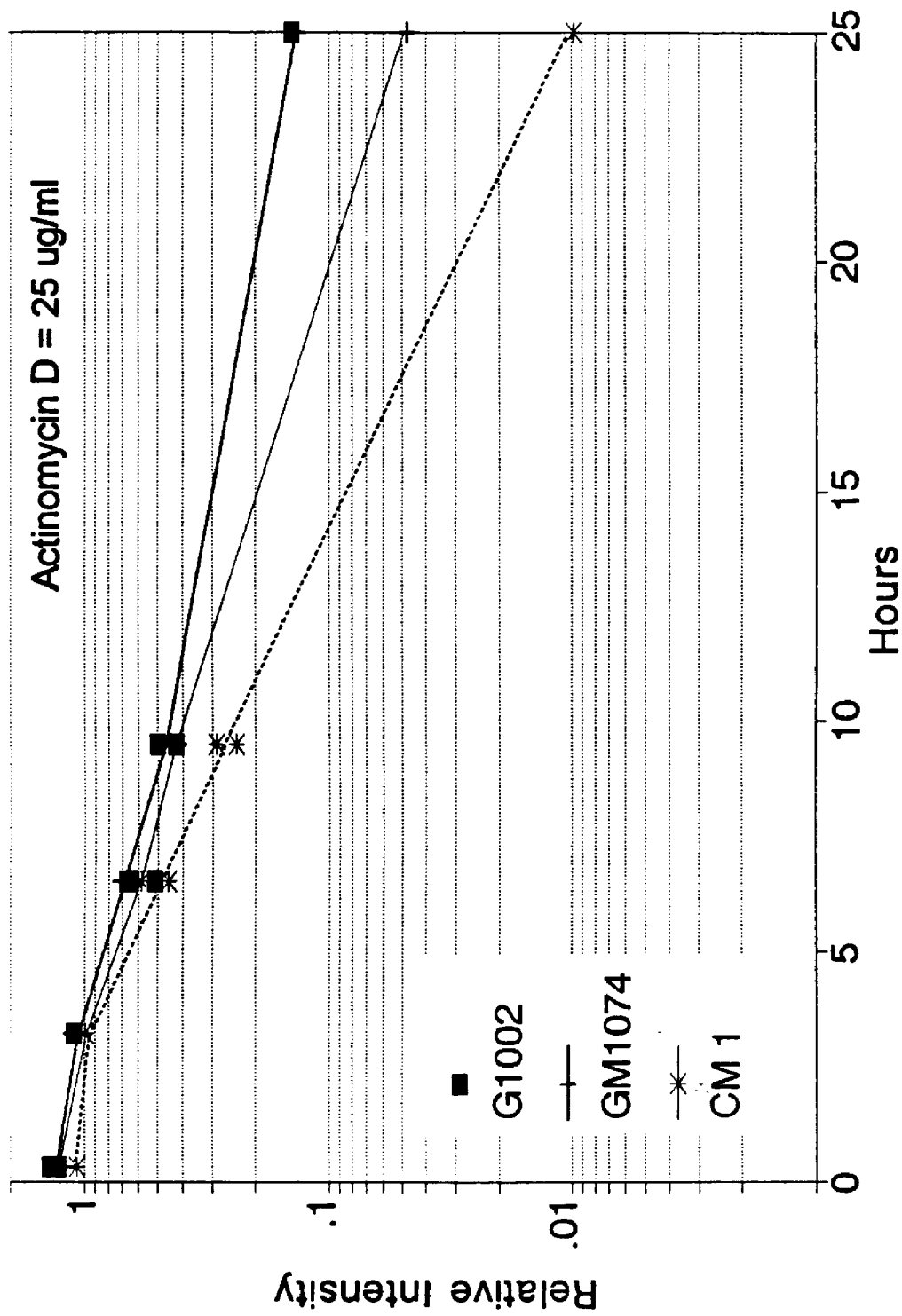
FIG. 33 illustrates the time course of bioluminescent signal decay after addition of Actinomycin D to the cell clones G1002, GM1074 and CM1. Time in hours is plotted against the logarithm of the ratio of the bioluminescent signal generated by Actinomycin D-treated cells over the signal of untreated control cells.

When screening for inhibitors rather than inducers of transcription, the half-life of the reporter molecule becomes a crucial parameter in determining the minimal incubation time that would be necessary to allow enough decay of reporter signal so that the inhibition of their synthesis became detectable. The cell lines G1002 and GM1074 containing luciferase reporter constructs for the G-CSF or GM-CSF were therefore tested for the time dependency of luciferase activity after treatment of the cells with Actinomycin D, an inhibitor of transcription. This experiment measures the combined half-life of luciferase mRNA and of the luciferase protein. Cells derived from clones G1002 and GM1074 were seeded into 96-well microtiter plates (20,000 cells G1002 or GM1074/well) and incubated overnight in cell culture conditions. At time O Actinomycin D (25 μg/ml) was added. At the times indicated in FIG. 33 cells were washed with PBS and luciferase activity of Actinomycin-treated cells determined as described previously. The logarithm of the treated/untreated ratio is plotted versus time. As demonstrated in FIG. 33, apparent half-lives found in the two cell lines tested ranged from about 2.5 to 6 hours. A 24 hour incubation with a 100% efficient inhibitor of transcription would therefore be sufficient to reduce luciferase levels to maximal 6% of the control in the tested cell lines.

High-Throughput Drug Screen

Figure 34:
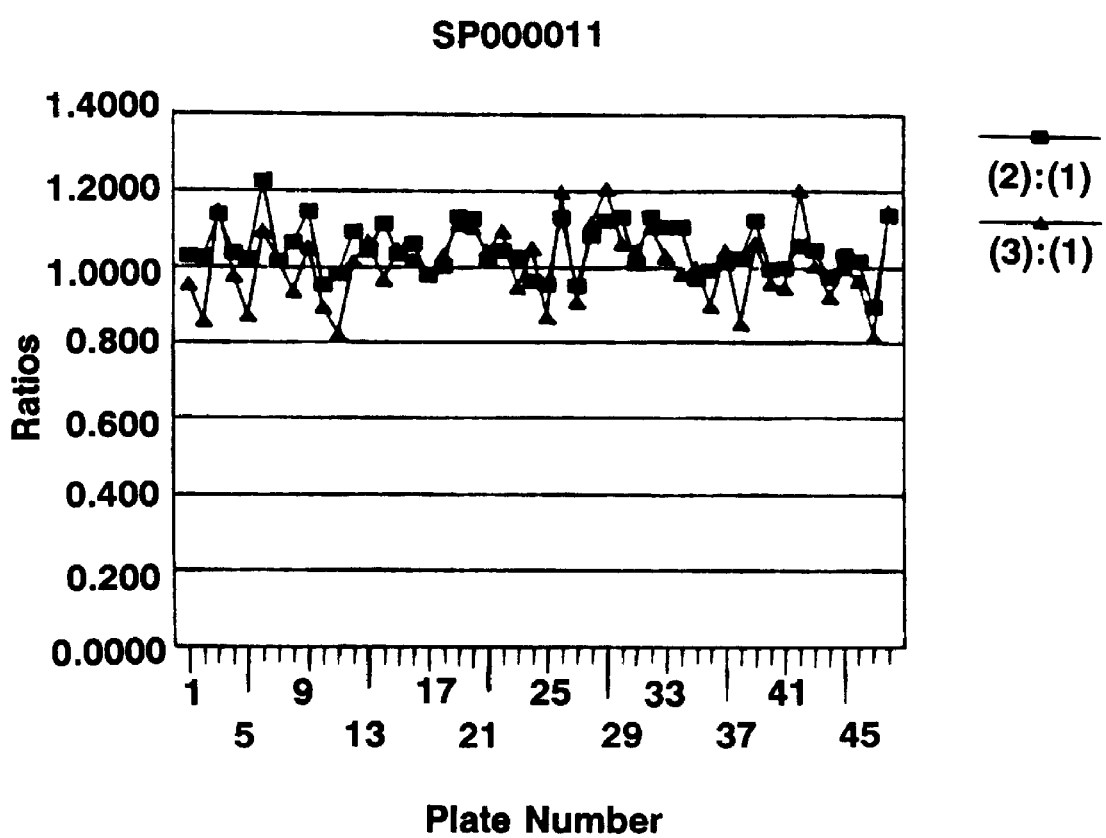
FIG. 34 is a quality assurance analysis of a high throughput screen measuring the ratios of negative values at various positions within a plate. The expected value is 1.0.
Figure 35:
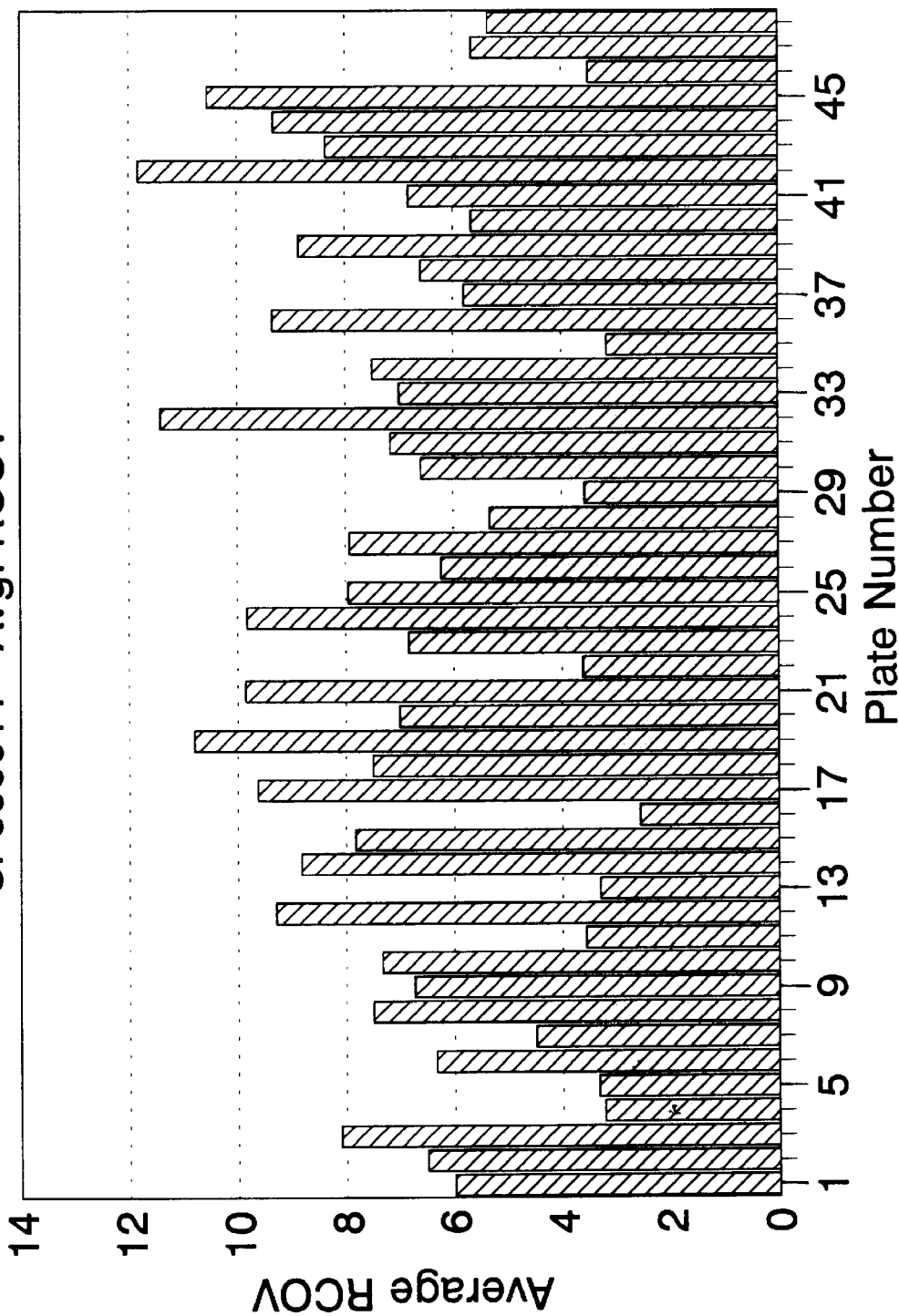
FIG. 35 is a quality assurance analysis of a high throughput screen measuring a coefficient of variance for the negative controls on a number of plates. Values less than 10 are acceptable.
Figure 36:
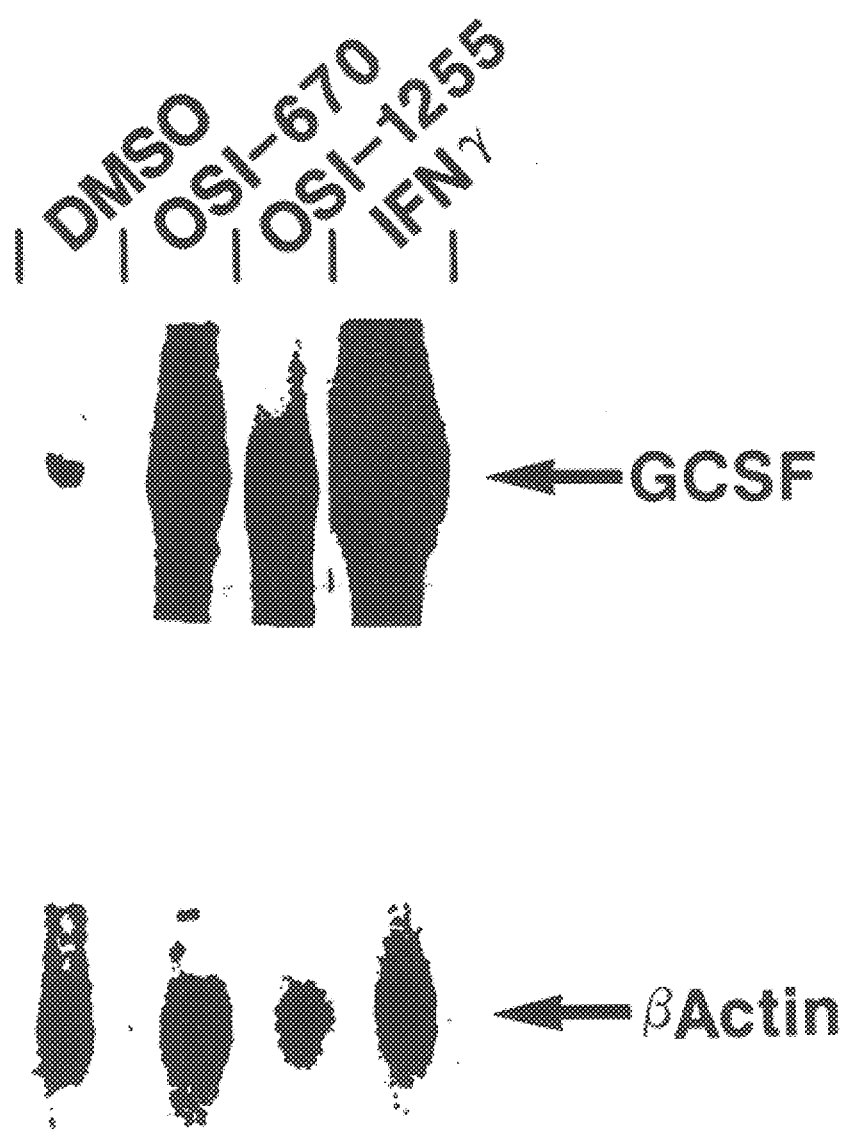
FIG. 36 is an autoradiograph of a Northern blot illustrating increased G-CSF mRNA production by the human epithelial cell line U5637 in response to chemicals #670 and #1255 and IFN-gamma as compared to the solvent DMSO. Reprobing with beta-actin was used to normalize for the amount of mRNA that had been loaded onto the gel.

Table 1 shows a summary of the results of a one-week, high-throughput screen of 2,000 chemicals to identify those chemicals specifically stimulating or inhibiting transcription from the G-CSF or MMTV (as a control for specificity) promoters. This screen concurrently tested chemicals at three concentrations on quadruplicate samples of the M10 and G21 cell lines. A minimum stimulation of one promoter, to the degree indicated, and less than 50% activation of the other promoter was required for a chemical to be considered a selective activator. A minimum inhibition of 3 fold of one promoter and less than 20% inhibition of the other promoter was required for a chemical to be considered a selective inhibitor. Table 2 gives the names and induction or inhibition ratios of the lead chemicals identified for each promoter. FIG. 34 illustrates the transcriptional stimulation and FIG. 35 the transcriptional inhibition observed with some of the lead chemicals. Some of the chemicals activating G-CSF transcription fell into conspicuous groups of analogs (Table 2; Group A and B). Although not specifically indicated in Table 2, groups of homologs and analogs can also be found for G-CSF-inhibiting chemicals as well.

To determine the number of lead chemicals, which reproducibly score as positives in repeated luciferase assays, two types of experiments were conducted:

1) G-CSF lead chemicals #1780, #58, #1783, #1374 were subjected to 48 independent luciferase assays performed on the same day. Compounds #58, #1780 and #1374 scored as positives in every single one of these assays inducing luciferase expression between 2 and 28 fold (#58), 20 and 80 fold (#1780) and 5 and 40 fold (#1374). Probably due to its relatively low induction of luciferase expression (1.5 to 8 fold), Compound #1783 scored as positive only in half of the 48 repeat assays.

2) All of the 18 lead chemicals inducing luciferase expression from the MMTV promoter were again subjected to luciferase assays: 10 chemicals (#453, #519, #562, #765, #828, #848, #1269, #1316, #1384 and #2148) again induced luciferase expression between 2.1 and 2.8 fold. Probably due to the relatively low induction level close to the background of the assay, the other eight lead chemicals did not repeat on that particular day. The most prominent lead chemical, #453 (13.3 fold induction in the original high-throughput assay), was repeated in a total of 3 independent assays and consistently induced luciferase expression from the MMTV promoter between 10 and 35 fold. Replacing DMSO by methanol to dissolve the chemical did not affect its ability to activate the MMTV promoter.

2. Screen II

In yet another independent high throughput screen (screen II), 500 compounds, consisting of 96 fermentation broths and 404 pure chemicals, were tested against a G-CSF (G1002) reporter cell line and an MMTV reporter control cell line. The number of lead compounds identified in this screen are shown in table 2.

Thus high-throughput screening of fermentation broth samples using a luciferase expression assay can consistently lead to the discovery of samples with the potential to be developed into novel pharmaceuticals.

Effects of Lead Chemicals on Endogenous G-CSF mRNA Levels

Northern blot analysis was used to demonstrate the stimulatory effects of lead chemicals #670 and #1255 on endogenous G-CSF mRNA levels. As shown in FIG. 30, both OSI #670 and #1255 stimulated production of G-CSF mRNA, as shown by a G-CSF-specific probe, but not of actin mRNA, as shown by a beta-actin-specific probe. Also shown are the effects of the solvent, DMSO, used to dissolve the chemicals and a proteinaceous positive regulator, interferon-gamma. From these data it is concluded that chemicals, which induce luciferase expression from specific promoters, in plasmids stably integrated into cells, are also capable of stimulating mRNA production from the corresponding endogenous promoters.

To further confirm, that compounds that had been identified in a luciferase expression assay using a G-CSF specific reporter cell line would be active in inducing transcription of the endogenous G-CSF gene, cells from the parental cell line 5637 used to construct the reporter cell line were incubated with cycloheximide (25 ug/ml), DMSO (0.5%,solvent control) and low, medium and high concentrations of the compounds 542 (10, 50, 250 μM),1255 (20, 100, 500 uM), 1793(0.25, 1.2, 6.25 μM) and 1904 (20, 100 uM) for 18 hours. RNA was extracted and the concentration of G-CSF, GM-CSF and gamma-actin mRNA was determined by the S1 protection method as described in above. The positions of G-CSF GM-CSF and gamma-actin specific protected fragments are indicated (G, GM, A) at the left side of the gel (FIG. 37).

Interestingly, all four compounds tested increased the amount of G-CSF mRNA and at least two of them, namely #542 and #1793, also increased the amount of GM-CSF mRNA. Compound #543, a structural analog of #542 showed similar activity.

Dose response Analysis of Structurally Related Lead Chemicals

Figure 38A:
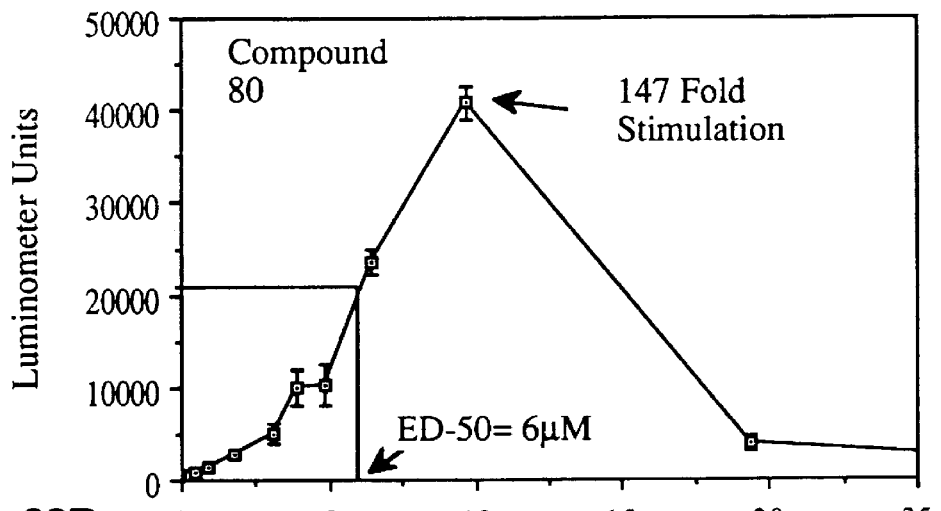
FIGS. 38A, 38B and 38C illustrate a dose response analysis of chemicals #80, #670, and #1780 using the G-CSF reporter cell line G21. The amount of luciferase expression is indicated in arbitrary units.
Figure 38B:
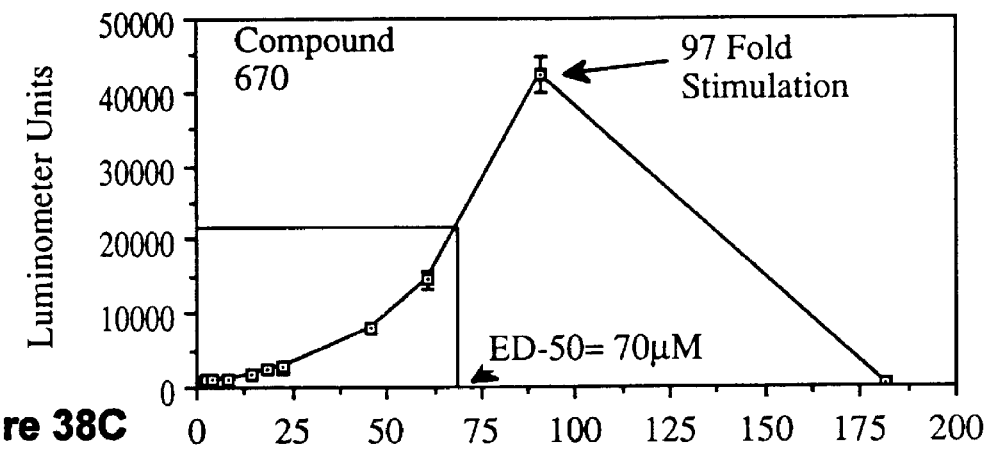
Figure 38C:
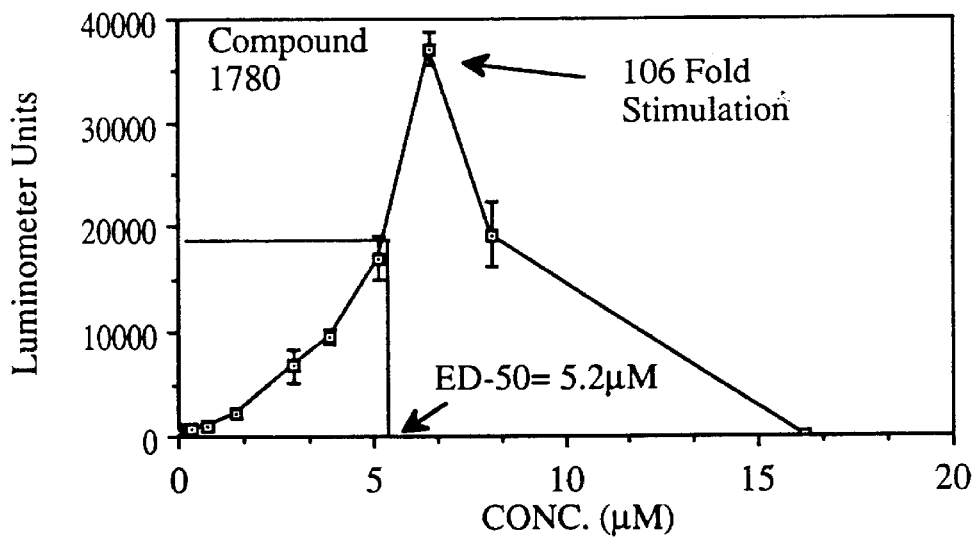
Figure 39:
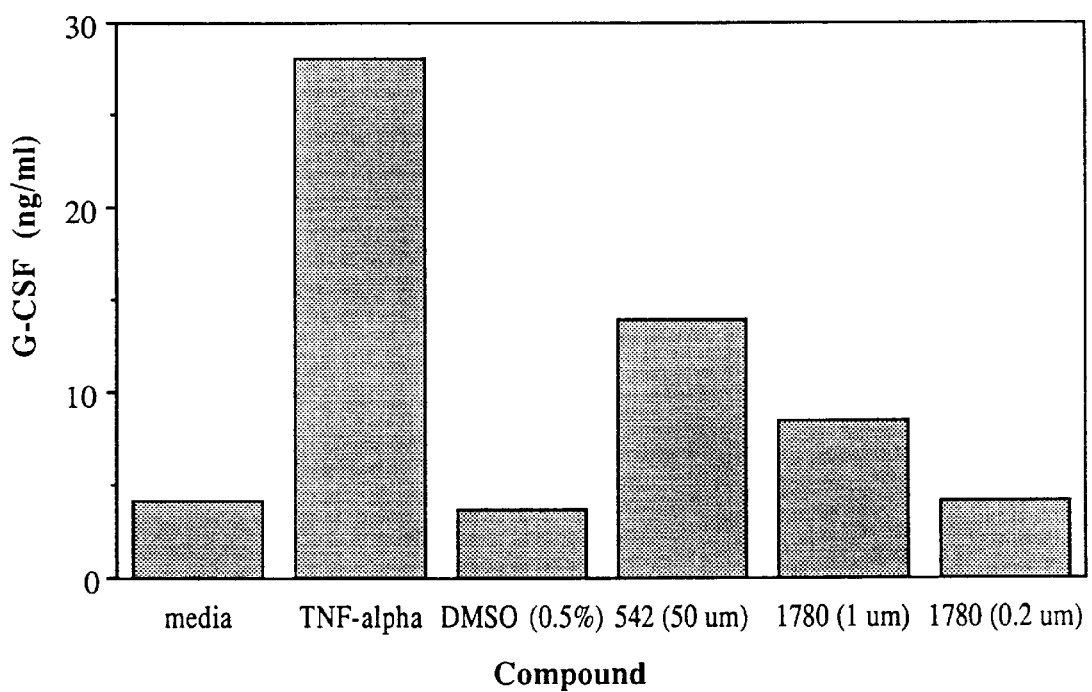
FIG. 39 is a bar graph illustrating increased G-CSF secretion by 5637 cells treated for 48 hours in serum-containing media with the samples indicated on the abscissa. TNF-alpha was used at 5 ng/ml. Chemicals #542 and #1780 were used at 50 uM or 1 uM and 0.2 uM final concentration, respectively. Both chemicals were used in DMSO at a final concentration of 0.5%. The ordinate indicates the concentration of G-CSF secreted into 5 ml of serum-containing media by 25 square cm of confluent 5637 cells.

Among the chemicals which specifically activated the G-CSF promoter were groups of structural homologs. Three such homologs, #80, #670, and #1780, belong to groups listed in Table 2. These three structurally related chemicals all specifically activated the G-CSF promoter. Dose response graphs obtained with chemicals #80, #670, and #1780 are shown in FIGS. 38A–38C. Although these chemicals all demonstrate large maximal stimulations, it is clear that their potencies, as measured by their $ED_{50}$'s (concentration of chemical resulting in 50% maximal stimulation), show wide variability (5–70 μm)).

Effects of Lead Chemicals on Target Protein Secretion

Two of the most promising lead chemicals (#542 and #1780), which were shown to stimulate levels of endogenous G-CSF mRNA as well as luciferase expression from the G-CSF promoter/luciferase fusion constructs, were further investigated for their ability to increase G-CSF secretion into the media of 5637 bladder carcinoma cells incubated with the chemicals for 48 hours. The levels of G-CSF in the cell supernatants were determined by a sandwich-antibody assay as described in above (FIG. 42).

Cytotoxicity of Lead Chemical #542

Figure 40:
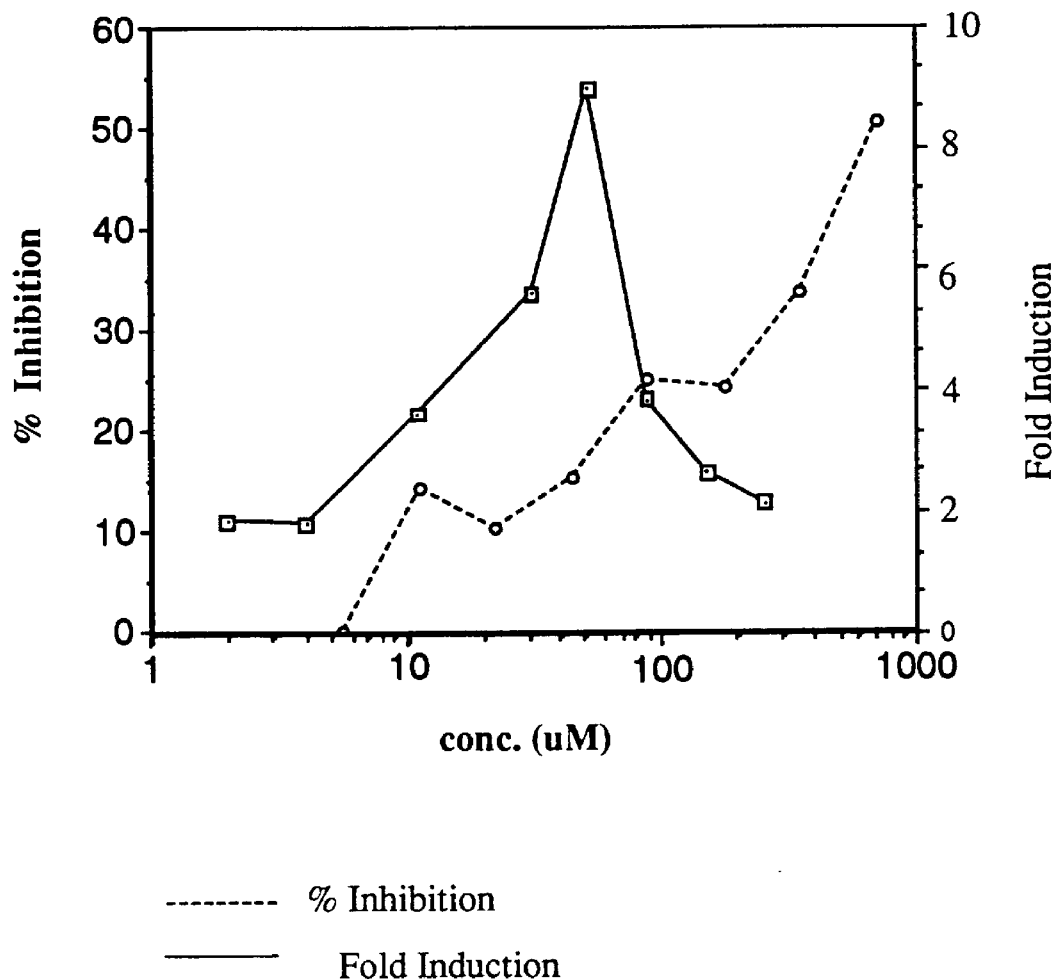
FIG. 40 illustrates a dose response analysis of chemical #542 using the G-CSF reporter cell line G 21 (solid line) and the MTT respiratory inhibition cytotoxicity assay (dotted line). Respiratory inhibition in percent of untreated control cells (Ordinate, left scale) and luciferase expression of #542-treated over solvent-treated cells (ordinate, right scale) are plotted against #542 concentration (abscissa).

To address the question whether the induction of G-CSF, and GM-CSF transcription by the compound #542 was a specific effect or rather a phenomenon linked to a potential sensitivity of these promoters to stress exerted by toxic compounds, the concentration dependency of induction of luciferase activity in the reporter cell line G21 was compared to the concentration dependency of inhibition of respiration in FRE cells. Cells were seeded into 96 well microtiter plates (20,000 cells/well) and cultured overnight. Compound #542 was added at various concentrations and the cells were incubated for 6 hours. Luciferase activity was determined as described above. The MTT-colorimetric assay was carried out on identically treated samples of FRE cells. Induction of luciferase reporter signal (plain line) and on inhibition of respiration (dashed line) are plotted versus the concentrations of compound (FIG. 40). The ED50 for induction of luciferase activity differed from the ED50 for inhibition of respiration by a factor of almost 10, which might indicate that compound #542 exerts a specific effect on G- and GM-CSF transcription.

PCR mRNA Detection and Quantitation

Oligonucleotides (SEQ ID NO: 87–93) were designed for the specific detection of each of the gene encoding proteins of interest associated with cardiovascular disease to be analyzed.

G-CSF   5' TGGCGCAGCGCTCCAGGAGAAGCTG3' and
        5' CGCTATGGAGTTGGCTCAAGCAGCCTGC3'

GM-CSF  5' GAGTAGAGACACTGCTGCTGAGATG3' and
        5' GGCGGGTCTGTAGGCAGGTCGGCTC3'

M-CSF   5' CTCCAGCCCGCAGCTCCAGGAGTCTG3' and
        5' CCCTCTACACTGGCAGTTCCACCTG3'

In each case, these oligonucleotides were chosen to amplify sequences which span two intron splice junctions and one exon in order to minimize the nonspecific signal generated by contaminating genomic DNA. The oligos for G-CSF are complementary to regions within their respective gene's exons II and IV and amplify the region corresponding to exon III. The oligos for GM-CSF are complementary to regions of hGM-CSF exons I and III and amplify the region corresponding to exon II. The oligonucleotides for M-CSF are complementary to regions of hM-CSF exons VI and VIII and amplify the region corresponding to exon VII.

Figure 41:
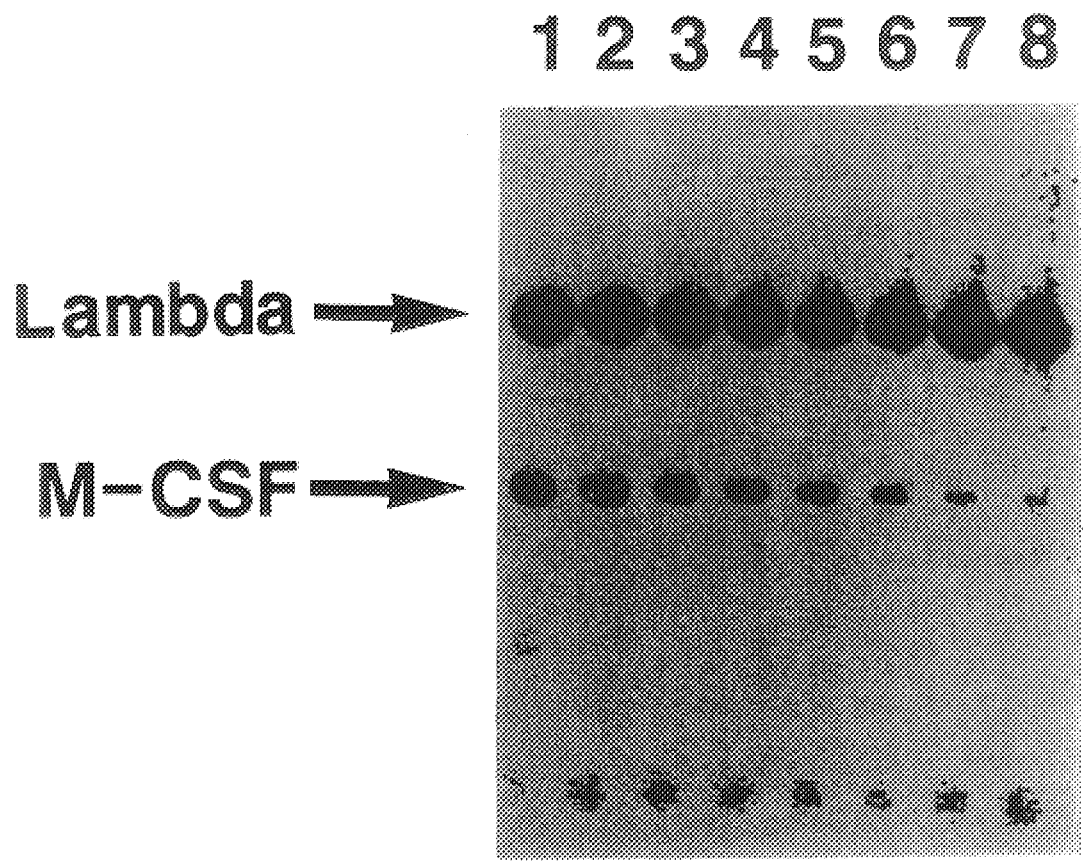
FIG. 41 is an autoradiogram of PCR reactions detecting varying amounts of M-CSF mRNA and a constant amount of lambda DNA.

To test the quantitative ability of the polymerase chain reaction, total RNA was isolated form U5637 bladder carcinoma cells and diluted in two-fold serial steps to yield samples ranging from 4 to 0.05 micrograms. These RNA samples were used to generate cDNA using random primers and then mixed with a constant amount of phage lambda DNA (0.2 ng) as a control for amplification efficiency. Alpha-$^{32}$P-dATP was included in the PCR buffer to allow quantitation of the amplified products. The M-CSF specific PCR oligonucleotides describe above were added to the standard reaction mixture (2 pmoles per sample) and PCR carried out for 35 cycles in a Perkin-Elmer-Cetus thermal cycler. The products of the reaction were electrophoresed on a 3% NuSieve agarose gel. The gel was dried and used to expose Kodak X-OMAT AR film. The resulting autoradiogram is shown in FIG. 41. This autoradiogram was quantitated using an LKB laser densitometer, the data are shown in FIG. 42. The graph plots the amount of M-CSF specific product divided by the constant lambda DNA signal. The reaction was clearly quantitative for the RNA samples between 0.05 and 1 microgram (total RNA), and proved to be a very sensitive assay for M-CSF mRNA, which is barely detectable in this cell line by conventional S1 analysis (not shown).

TABLE 1

SUMMARY OF HIGH-THROUGHPUT SCREEN I

Number (%) of Chemicals Which Activate Expression:

| Total | 2–3X | 3–5X | 5–7X | 7–10X | >10X |
|---|---|---|---|---|---|
| G-CSF 38 | NA | 23 | 10 | 3 | 2 |
| (1.9%) | | (1.1%) | (0.5%) | (0.15%) | (0.10%) |
| MMTV 18 | 15 | 1 | 0 | 1 | 1 |
| (0.9%) | (0.7%) | (0.05*) | (0%) | (0.05%) | (0.05%) |
| hGH 23 | NA | NA | 12 | 5 | 6 |
| (1.14%) | | | (0.6%) | (0.03%) | (0.03%) |

Number (%) of Chemicals Which Inhibit Expression >3 Fold

| Promoter | |
|---|---|
| G-CSF | 7 (0.35%) |
| MMTV | 1 (0.05%) |
| hGH | 42 (2.1%) |

TABLE 2

| Chemical # | Chemical Name | GCSF | hGH | MMTV |
|---|---|---|---|---|
| A) TRANSCRIPTIONAL ACTIVATORS | | | | |
| G-CSF: | | FOLD INDUCTION RELATIVE TO SOLVENT CONTROL | | |
| 40 | 3-Acetyl-2-6-Bis(tertiary butyl amino)-4-methyl-pyridine | 5.62 | 0.62 | 0.27 |
| 58 | 1-Acetylimidazole | 6.03 | 0.17 | 0.42 |
| 237 | N-Carbethoxy-phthalimide | 4.77 | 0.06 | 0.62 |
| 254 | 1-(2-Chloroethyl) piperidine | 4.09 | 0.90 | 0.98 |
| 364 | Melamine | 3.67 | 1.18 | 1.07 |
| 473 | 1,3,5,-Triazine | >3 | 0.50 | 0.87 |
| 542 | 5-Bromo-2'-deoxycytidine | 6.28 | 1.08 | 1.26 |
| 543 | 5-Bromo-2'-deoxyuridine | 7.17 | 0.72 | 0.98 |
| 878 | Blueberry leaf extract | 3.84 | 1.17 | 0.78 |
| 1025 | Culvers Root extract | 4.09 | 0.98 | 1.24 |
| 1234 | 4-Aminocinnamic Acid hydrochloride | 4.97 | 0.51 | 1.03 |
| 1255 | 1-Bromo-3,5-dichloro-benzene | 6.74 | 0.43 | 1.09 |
| 1374 | 4'-Amino-N-methyl-acetanilide | 11.03 | 0.05 | 1.05 |
| 1375 | 4'-(aminomethyl)benzene sulfonamide hydrochloride | 8.94 | 0.04 | 1.37 |
| 1376 | 2-Amino-5-Methyl benzene sulfonic acid | 6.37 | 0.04 | 1.32 |
| 1397 | 5-Amino-3-methylisothi-azole hydrochloride | 3.63 | 0.57 | 1.13 |
| 1482 | 2-Aminophenyl disulfide | 3.99 | 0.54 | 1.07 |
| 1483 | 4-Aminophenyl disulfide | 4.64 | 0.38 | 1.09 |
| 1521 | 2-Amino-6-purinethiol | 3.59 | 0.73 | 0.92 |
| 1583 | 8-Bromoadenosine | 5.82 | 0.12 | 0.88 |

TABLE 2-continued

| Chemical # | Chemical Name | GCSF | hGH | MMTV |
|---|---|---|---|---|
| 1592 | Bis(2,2,3,3,4,4,5,5,6,6,7,7,) dodecafluoroheptyl-(+)-camphorate | 3.20 | 0.74 | 1.34 |
| 1783 | Cupferron | 6.55 | 0.32 | 0.89 |
| 1793 | Cyanomethyl-N,N-dimethyl dithiocarbamate | 9.50 | 0.52 | 1.21 |
| 1994 | 3-Bromobiphenyl | 3.29 | 0.34 | 0.63 |
| 2001 | 1-Bromo-4-tertiary butyl benzene | 3.11 | 0.74 | 1.12 |
| 2030 | 4-Bromo-2-fluoro-6-nitroanizol | 5.53 | 0.67 | 0.87 |
| 2096 | (+)-1-Bromo-3-Chloro-2methyl propane | 3.27 | 0.61 | 0.89 |
| 2097 | 1-Bromo-5-Chloro pentane | 5.09 | 0.88 | 1.22 |
| 2129 | 4-Chlorobenzyl Chloride | 3.23 | 0.75 | 0.95 |
| GROUP A: | | | | |
| 378 | 7-Oxo-7H-benzo[e]pyrimidine 4-carboxylic acid | 4.12 | 0.26 | 0.59 |
| 423 | Quinacrine dihydrochloride hydrate | 2.39 | 0.56 | 0.64 |
| 427 | Resazurin | 3.14 | 0.43 | 0.71 |
| 836 | Thionin | 3.20 | 0.23 | 0.58 |
| 1776 | Cresyl Violet Acetate | 3.50 | 0.15 | 1.36 |
| 1904 | 9-Aminoacridine hydrochloride | 4.12 | 0.54 | 0.82 |
| GROUP B: | | | | |
| 670 | Methyl Green | >3 | 0.52 | 0.79 |
| 1780 | Crystal Violet | 20.39 | 0.38 | 1.15 |
| GROUP A AND B: | | FOLD INDUCTION | | |
| 80 | Acridine Orange | 5.87 | 0.66 | 0.83 |
| hGH: | | | | |
| 70 | 2-Acetylpyrrole | 0.43 | 9.26 | 0.85 |
| 299 | 10,11-Dihydrocarbamazepine | 0.53 | 5.46 | 0.47 |
| 322 | 1-ethyl-2-benzimidazolinone | 0.60 | 11.18 | 1.12 |
| 325 | Fisetin | 0.14 | 5.42 | 1.0 |
| 552 | 3-(4-chlorophenyl)-1-methoxy-1-methyl urea | 0.81 | 5.31 | 0.86 |
| 790 | Rivanol | 0.01 | 5.94 | 0.58 |
| 792 | Rose Bengal | 0.94 | 5.31 | 1.21 |
| 856 | Tripa mitin | 0.28 | 6.49 | 0.42 |
| 1004 | Arnica 4x | 0.85 | 6.48 | 1.22 |
| 1160 | Rochester #6180 | 0.38 | 5.79 | 0.80 |
| 1251 | Bromocresol Green | 0.14 | 15.19 | 0.33 |
| 1337 | 4-Amino-5-hydroxy-1-naphthalene sulfonic acid | 0.07 | 15.87 | 0.23 |
| 1499 | 2-Amino-4-phenylthiazole hydrobromide monohydrate | 0.24 | 5.55 | 0.61 |
| 1550 | 2-Aminothiazole | 0.04 | 5.44 | 0.87 |
| 1552 | 2-amino-2-thiazoline | 1.23 | 7.26 | 0.52 |
| 1561 | 4-Amino-3,5,6-trichloro-picolinic acid | 0.23 | 8.05 | 0.48 |
| 1598 | N,N'-Bis-[3-(4,5-dihydro-1H-imidizol-2-yl)phenyl] urea dipropanoate | 0.72 | 5.32 | 1.27 |
| 1678 | 4'8-Bis(hydroxymethyl)-tricyclo [5,2,1,0$^{2\cdot 6}$] decane | 0.36 | 7.08 | 0.89 |
| 1740 | 5-carbethoxy-2-thiouracil | 0.74 | 17.77 | 0.87 |
| 1747 | N$_6$-carbobenzyloxy-L-lysine | 0.78 | 6.16 | 0.86 |
| 1804 | Cyclobutane carboxylic acid | 1.05 | 9.41 | 0.49 |
| 1876 | Alec Blue | 0.87 | 11.91 | 0.40 |
| 1881 | Alizarin Blue Black B | 0.21 | 18.87 | 0.69 |
| MMTV: | | | | |
| 189 | Bathocuproinedisulfonic Acid disodium salt hydrate | 1.06 | 1.47 | 2.80 |
| 453 | 2,2',6',2"-Terpyridine | 0.79 | 0.58 | 13.30 |
| 519 | b-Apo-8'-carotenal | 1.15 | 0.68 | 2.76 |
| 562 | Copaiva Balsam | 1.10 | 0.15 | 2.34 |
| 629 | Homoveratric acid | 0.85 | 1.05 | 2.48 |
| 633 | 5-Iodorotic acid | 1.02 | 0.86 | 2.46 |
| 765 | Prednisolone-21-Acetate | 0.96 | 1.30 | 2.66 |
| 828 | 2,4,5,4'-Tetrachloro-diphenylsulfide | 1.47 | 1.34 | 2.20 |
| 848 | Triamcinolone acetonide | 0.75 | 1.28 | 2.43 |
| 944 | Peanut | 1.15 | 0.91 | 2.10 |
| 1269 | 5-Amino-4,6-dichloro-pyrimidine | 0.72 | 0.91 | 2.18 |
| 1316 | 2-Aminofluorene | 0.74 | 1.39 | 2.33 |
| 1318 | 2-Amino-9-fluorenone | 1.13 | 0.85 | 2.41 |
| 1384 | 2-Amino-4'-methylbensophenone | 1.33 | 0.50 | 2.43 |
| 1573 | 5-Bromoacenapthene | 1.49 | 0.34 | 4.30 |
| 2064 | 4-(Bromomethyl)-6,7-dimethoxy coumarin | 0.82 | 1.10 | 2.53 |
| 2148 | 2-chlorocyclohexanone | 0.45 | 0.92 | 2.82 |
| 2191 | Chloramphenicol | 0.37 | 0.35 | 7.32 |
| B) TRANSCRIPTIONAL INHIBITORS | | | | |
| | | FOLD INHIBITION RELATIVE TO SOLVENT CONTROL | | |
| G-CSF: | | | | |
| 209 | 4-Benzoylpyridine | 6.66 | 1.08 | 0.81 |
| 371 | Morin hydrate | 11.11 | 0.41 | 0.89 |
| 660 | Maclurin | 10.0 | 0.34 | 1.04 |
| 798 | Salicylamide | 4.76 | 0.90 | 0.68 |
| 2009 | 4-Bromo-3,5-dimethyl-pyrazole | 3.70 | 0.57 | 0.64 |
| 2082 | 4-Bromo-3-Methyl-pyrazole | 5.26 | 0.65 | 1.23 |
| 2121 | 3-Chlorobenzyl alcohol | 4.76 | 0.40 | 1.14 |
| hGH: | | | | |
| 183 | Auramine O | 0.72 | 4.00 | 0.70 |
| 240 | Carminic acid | 0.63 | 5.26 | 0.80 |
| 443 | Sulfamethazine | 0.60 | 4.76 | 0.79 |
| 512 | Amaranth | 0.81 | 5.26 | 0.68 |
| | | FOLD INHIBITION | | |
| 541 | 5-Bromo-4-Chloro-3-indoxy-phosphate K-salt | 0.90 | 6.25 | 0.86 |
| 556 | Chromazurol S | 0.73 | 33.33 | 0.87 |
| 561 | Clove Oil | 0.62 | 5.00 | 0.05 |
| 577 | Na-Ne-Diacetyl-L-lysine | 0.64 | 4.00 | 0.68 |
| 578 | Dibenzoyl-D-tartaric acid | 0.65 | 4.00 | 0.91 |
| 630 | Hydantoin-5-acetic acid | 0.70 | 3.57 | 0.74 |
| 640 | Kernechtrot | 0.64 | 5.00 | 0.59 |
| 759 | Piperidine | 0.64 | 5.88 | 0.95 |
| 764 | Prednisolone | 0.82 | 4.54 | 0.59 |
| 675 | Black Walnut extract | 0.69 | 6.25 | 0.80 |
| 892 | Colts Foot Leaves extract | 0.68 | 11.11 | 0.87 |
| 893 | Comfrey Leaf extract | 0.74 | 11.11 | 0.90 |
| 920 | Horehound Herb extract | 0.56 | 3.84 | 0.84 |
| 921 | Horsetail Grass extract | 0.72 | 3.44 | 0.86 |
| 942 | Pau D'Arco extract | 0.80 | 6.25 | 0.63 |
| 970 | Thyme extract | 0.57 | 4.34 | 1.07 |
| 1591 | 1,2-Bis(di-p-tolylphosphino)-ethane | 0.56 | 5.55 | 0.96 |
| 1604 | 2,4-Bis[5,6-bis(4-sulfophenyl)-1,2,4-Triazine-3-yl)-pyridine, tetrasodium salt hydrate | 0.77 | 5.00 | 0.97 |
| 1635 | [(1S)-endo]-(−)-Borneol | 0.71 | 9.09 | 0.99 |
| 1640 | 1,2-Bis(2-pyridyl)-ethylene | 0.79 | 5.00 | 0.59 |
| 1641 | 2,3-Bis(2-pyridyl)-pyrazine | 0.83 | 5.55 | 0.60 |

TABLE 2-continued

| Chemical # | Chemical Name | GCSF | hGH | MMTV |
|---|---|---|---|---|
| 1648 | 2-[5,6-Bis(4-sulfo-phenyl)-1,2,4-triazine-3-yl]-4-(4-sulfophenyl)-pyridine, trisodium salt | 0.86 | 7.69 | 1.00 |
| 1651 | Bis(2,2,2-trifluoroethyl)(methocarbonyl-methyl)-phosphonate | 0.69 | 3.57 | 0.70 |
| 1655 | 2,5-Bis(trifluoro-methyl)benzoic acid | 0.54 | 4.76 | 0.81 |
| 1703 | 3-Bromobenzonitrile | 0.76 | 10.00 | 0.90 |
| 1704 | 4-Bromobenzonitrile | 0.77 | 4.16 | 0.94 |
| 1705 | 4-Bromobenzophenone | 0.54 | 14.28 | 0.62 |
| 1712 | Calcein Blue | 0.74 | 8.33 | 0.94 |
| 1720 | (15)-(−)-Camphor | 0.65 | 4.76 | 0.66 |
| 1764 | 7-(Carboxymethoxy)-4-Methylcoumarin | 0.55 | 7.14 | 0.82 |
| 1770 | Carminic acid | 0.54 | 10.00 | 0.57 |
| 1771 | L-Carnosine | 0.71 | 10.00 | 0.72 |
| 1773 | O-Cresolphthalein Complexone | 0.62 | 10.00 | 0.67 |
| 1890 | Alloxazine | 0.80 | 5.26 | 0.58 |
| 2035 | 5-Bromofuroic acid | 0.57 | 7.14 | 0.89 |
| 2036 | 8-Bromoguanosine | 0.58 | 4.34 | 0.81 |
| 2037 | 1-Bromohexadecane | 0.51 | 4.00 | 0.50 |
| MMTV: | | | | |
| 2010 | 2-Bromo-4,6-dinitroaniline | 0.80 | 0.63 | 3.57 |

TABLE 3

SUMMARY OF HIGH THROUGHPUT SCREEN II
Number (%) of Chemicals Which Activate Expression:

| | 2–3X | 3–5X | 5–7X | 7–10X | >10X | Total |
|---|---|---|---|---|---|---|
| G-CSF | 0 (0%) | 2 (0.4%) | 0 (0%) | 0 (0%) | 0 (0%) | 2 (0.4%) |
| MMTV | 2 (0.4%) | 2 (0.4%) | 3 (0.6%) | 1 (0.2%) | 1 (0.2%) | 9 (1.8%) |

CYTOTOXIC COMPOUNDS: 5 (1%)

REFERENCES

1. Ylä-Herttuala, S., et al., (1990), Proc. Natl. Acad. Sci. USA, 87:6959–6963.
2. Cybulsky, M. I., et al., (1991), Proc. Natl. Acad. Sci. USA, 88:7859–7863.
3. Cushing, S. D., et al., (1990), Proc. Natl. Acad. Sci. USA, 87:5134–5138.
4. Ross, R. (1986), N. Engl. J. Med., 314:488–500.
5. Linder, V. and Reidy, M. A. (1991), Proc. Natl. Acad. Sci. USA, 88:3739–3743.
6. Bonin, P. D., et al., (1989), Exp. Cell Res., 181:475–482.
7. Ferns, G. A. A., et al., (1991), Science, 253:1129–1132.
8. Rajavashisth, T. B., et al., (1990), Nature, 344:254–257.
9. Ross, R., et al., (1990), Science, 248:1009–1012.
10. Rubin, K., et al., (1988), Lancet, 8599:1353–1356.
11. Ku, George, et al. (1988), Am. J. Cardiol. 62:77B–81B.
12. Soboleva, E. L. and Popkova, V. M. (1989), Biull. Eksp. Biol. Med, 107(5):600–604.
13. Smith, E. B., (1989), Human Atherosclerotic Lesion: An Overview. In *Atherosclerosis VIII* (G. Crepaldi et al., eds.) Elsevier Science Publishers B. V., Amsterdam, pp. 13–19.
14. Grundy, S. M. (1991), Arteriosclerosis and Thrombosis, 11: 1619–1635.
15. Brown, G., et al., (1990), N. Engl. J. Med., 323:1289–1298.
16. Nimer, S. D., et al., (1988), JAMA, 260:3297–3300.
17. Yamada, S. H., et al., (1990), Ann. N. Y. Acad. Sci., 587:362–370.
18. Rubin, E. M., et al., (1991), Nature, 353:265–267.
19. Johnson, W. J., et al., (1991), J. Lip. Res., 32:1993–2000.
20. Warden, C. H., et al., (1989), J. Biol. Chem., 264:21573–21581.
21. Inazu, A., et al., (1990), N. Engl. J. Med., 323:1234–1238.
22. Mendez, A. J., et al., (1991), J. Biol. Chem., 266:10104–10111.
23. Krause, B. R. and Newton, R. S. (1989), ACAT Inhibitors: Preclinical Pharmacologic Profiles and Implications for Plasma Lipid and Prevention of Atherosclerosis. In *Atherosclerosis VII* (G. Crepaldi et al., eds.) Elsevier Science Publishers B. V., Amsterdam, pp. 707–710.
24. Noshiro, M. and Okuda, K. (1990), FEBS Lett., 268:137–140.
25. Hadie, D. G., et al., (1989), TIBS 14, January, pp. 20–23.
26. Spence, J. D. (1989), Effects of Antihypertensive Drugs on Blood Flow Disturbances. In *Atherosclerosis VIII* (G. Crepaldi et al., eds.) Elsevier Science Publishers B. V., Amsterdam, pp. 575–579.
27. Sarzani, R., et al., (1991), Hypertension, 17:888–895.
28. Hsieh, H. J., et al., (1991), Am. J. Physiol., 260:642–646.
29. DeFeudis, F. V. (1991), Life Sciences, 49:689–705.
30. Fingerle, J., et al., (1989), Cell Biol., 86:8412–8416.
31. Sato, Y., et al., (1991), Biochem. Biophys. Res. Commun., 174:1260–1266.
32. Majesky, M. W., (1990), J. Cell. Biol., 111:2149–2158.
33. Meade, T. W. (1989), Haemostatic Function and Ischaemic Heart Disease. In *Atherosclerosis VIII* (G. Crepaldi et al., eds.) Elsevier Science Publishers B. V., Amsterdam, pp. 449–456.
34. Minno, G. D. and Cerbone, A. M., (1989), Fibronogen. A Coagulation Protein in the Cardiovascular Risk Factor Profile. In *Atherosclerosis VIII* (G. Crepaldi et al., eds.) Elsevier Science Publishers B. V., Amsterdam, pp. 469–474.
35. Blomback, M. and Hamsten, A. (1989), Haemostatic Function in Patient with Coronary Atheromatosis. In *Atherosclerosis VIII* (G. Crepaldi et al., eds.) Elsevier Science Publishers B. V., Amsterdam, pp. 475–478.
36. Loskutoff, D. J. and Curriden, S. A. (1990), Ann. N. Y. Acad. Sci., 598:238–247.
37. Reilly, C. F. and McFall, R. C. (1991), J. Biol. Chem., 266:9419–9427.
38. McLean, J. W., et al., (1987), Nature, 330:132–137.
39. Knott, T. J., et al., (1986), Nature, 323:734–738.
40. Smith, J. r., et al., (1990), J. Biol. Chem., 265:2306–2310.
41. Matsumoto, A., et al., (1990), Proc. Natl. Acad. Sci. USA, 87:9133–9137.
42. Tischer, E., et al., (1991), J. Biol. Chem., 266, 11947–11954.
43. Noy, S. N., et al., (1990), J. Biol. Chem., 265:6389–6393.
44. Burt, D. W., et al., (1989), J. Biol. Chem., 264:7357–7362.
45. Herr, W., (1991), Regulation of Eucarotic RNA polymerase II transcription by sequence specific DNA-binding proteins in *Hormonal Control of Gene Transcription*. (Cohen, P. and Foulkes, G. J., eds.), Elsevier Science Publishers, B. V., Amsterdam, p 333.
46. Yanofsky, C. and Crawford, I. P., (1987), in *Escherichia coli and Salmonella typhimurium: Cellular and Molecular Biology* (F. C. Neidhardt et al., eds.) Vol. 2, p. 1453.
47. Schlief, R. (1987), in *Escherichia coli and Salmonella typhimurium: Cellular and Molecular Biology* (F. C. Neidhardt et al., eds.) Vol. 2, p. 1473.

48. McClure (1985), Ann. Rev. Biochem., 54:171.

49. Hoopes, B. C. and McClure, W. R. (1987), in *Escherichia coli and Salmonella Typhimurium: Cellular and Molecular Biology* (F. C. Neidhardt et al., eds.) Vol. 2, p. 1231.

50. Matthews, B. W. (1987), Cro repressor structure and its interaction with DNA. In *DNA: Protein Interactions and Gene Regulation* (E. B. Thompson and J. Papaconstantinou, eds.) University of Texas Press, Austin.

51. Schlief, R. (1988), Science, 241:1182.

52. Evans, R. M. and Hollenberg, S. M. (1988), Cell, 52:1.

53. Landschulz, W. H., et al., (1988), Science, 240:1759.

54. Levine, M. and Hoey, T. (1988), Cell, 55:537.

55. Krainer, A. R. and Maniatis, T. (1988) RNA splicing. In *Transcription and Splicing* (Hames, B. D. and Glover, D. M., eds.) IRL Press, Washington, D.C., Vol. 1.

56. Proudfoot, N. J. and Whitelaw, E. (1988), Termination and 3' end processing of eucaryotic RNA. In *Transcription and Splicing* (Hames, B. D. and Glover, D. M., eds.) ERL Press, Washington, D.C., Vol. 1, p. 97.

57. La Thangue, N. B. and Rigby, P. W. J. (1988), Trans-acting protein factors and the regulation of eukaryotic transcription. In *Transcription and Splicing* (Hames, B. D. and Glover, D. M., eds) IRL Press, Washington, D.C., Vol. 1.

58. Yamamoto, K. R. (1985), Ann. Rev., Genet., 19:209.

59. Denison, M. S., et al., (1988), Proc. Natl. Acad. Sci. USA, 85:2528.

60. Hoeffler, J. P., et al., (1988), Science, 242:1430.

61. Angel, P., et al., (1987), Mol. Cell. Biol., 7:2256.

62. Angel, P., et al., (1987), Cell, 49:729.

63. Edelman, A. M., et al., (1987) Protein Serine/Threonine Kinases Ann. Rev. 56:567–613.

64. Gunter, K. C., et al., (1989), J. Immunol., 142:3286–3291.

65. Tocci, M. J., et al., (1989), J. Immunol., 143:718–726.

66. Wu, K. K., et al., (1990), Proc. Natl. Acad. Sci. USA, 88:2384–2387.

67. Yamamoto, K. K., et al., (1988), Nature, 334:494.

68. De Wet, J. R., et al., (1985), Proc. Natl. Acad. Sci. USA, 82:7870.

69. Engebrecht, J. M., et al., (1985), Science, 227:1345.

70. Bottenstein, J., et al., (1979), Methods in Enzymology, 58:94.

71. Higuchi, K., et al., (1988), J. Biol. Chem., 263:18530–18536.

72. Ladias, J. A. A. and Karathanasis, S. K., (1991), Science, 251:561–565.

73. Jelinek, D. F., et al., (1990), J. Biol. Chem. 265:8190–8197.

74. Rambaldi, A., et al., (1987), Blood., 69:1409–1413.

75. Leonard, E. J. and Yoshimura, T., (1990), Immunol. Today., 11:97–101.

76. Huber, P., et al., (1990), J. Biol. Chem., 265:5695–5701.

77. Maniatis, T., et al. (1982), *Molecular Cloning: A Laboratory Manual* Cold Spring Harbor Labs C.S.H. New York.

78. Ow, D. W., et al., (1986), Science 234:856–859.

79. McKnight, S. L. (1982), Cell, 31:355.

80. Gorman, C. (1985) Vectors used in mammalian cell expression. In *DNA Cloning*, Vol. II (D. M. Glover, ed). IRL Press, Washington, D.C.

81. Hudson, L. G., et al., (1990), J. Biol. Chem. 265:4389–4393.

82. Jordando, J. and Perucho, M. (1988) Oncogene 2: 359–366.

83. Liu, B., et al., (1991), J. Virol. 65:897–90.

84. Pouwels, Ph.H., Enger-Valk, B. E., and Brammar, W. J. (1985) *Cloning Vectors*. Elsevier Science Publishers, B. V., Amsterdam.

85. Graham, F. L. and Van der Ed, A. J. (1973), Virology, 52:456.

86. Sastry, K. N., et al., (1988), Mol. Cell. Biol., 8:605–614.

87. Sudhof, T. C., et al., (1985), Science, 228:815–822.

88. O'Farrel et al., (1977), Cell, 12:1133–1142.

89. Ladner, M. B., et al., (1987), EMBO J., 6:2693.

90. Rollins, B. J., et al., (1989), Mol. Cell Biol., 9:4687–4695.

91. Huber, P., et al., (1987), Nuc. Acids. Res., 15:1615–1625.

92. Minvielle, S., et al, (1991) J. Biol. Chem. 266:24627–24631,

93. Rosenfeld, M. G., et al., (1984) Science 225: 1315–1320.

94. Amara, S. G., et al., (1984) Mol. Cell. Biol. 4:2151–2160.

95. de Bustros, et al., (1985) J. Biol. Chem. 98–104.

96. Segond, N., et al. (1985) FEBS Lett. 184: 268–272.

97. Cote, G. J. and R. F. Gagel (1986) J. Biol. Chem. 15524–15528.

98. Shi, X. Y., et al., (1990) Chung Hua Nei Tsa Chih (China) 29: 616–639.

99. Fujioka, S., et al., (1991) J. Hypertens. (England) 9: 175–179.

100. Tang, J. A., et al. (1989) Chin. Med. J. (Engl) 102:897–901.

101. Broad, P. M., et al., (1989) Nucl. Acid. Res. 17: 6999–7011.

102. Das, H. K., et al., (1988), J. Biol. Chem., 263:11452–11459.

103. Auwerx, J. H., et al., (1989), Mol. Cell. Biol., 9:2298–2302.

104. Pandak, W. M., et al., (1991), J. Biol. Chem., 266:3416–3421.

105. Keck, P. J., et al., (1989), Science, 246:1309–1312.

106. Leung, D. W., et al., (1989), Science, 246:1306–1309.

107. Myoken, Y., et al., (1991), Proc. Natl. Acad. Sci. USA, 88:5819–5823.

108. Bottalico, L. A., et al., (1991), J. Biol. Chem., 266: 22866–22871.

109. Novak, E., et al., (1992), J. Cell. Biochem., January 13–26, p. 5.

110. Duncan, K. G., et al., (1990), Proc. Natl. Acad. Sci. USA, 87:7588–7592.

What is claimed is:

1. A method of determining whether a chemical not previously known to be a modulator of protein biosynthesis is capable of specifically transcriptionally modulating the expression of a gene encoding a protein of interest associated with the treatment of one or more symptoms of a cardiovascular disease which comprises:

(a) contacting a sample which contains a predefined number of identical eucaryotic cells with a predetermined concentration of the chemical to be tested, each such cell comprising a DNA construct consisting essentially of in 5' to 3' order (i) a modulatable transcriptional regulatory sequence of the gene encoding the protein of interest, (ii) a promoter of the gene encoding the protein of interest, and (iii) a reporter gene which expresses a polypeptide capable of producing a detectable signal, coupled to, and under the control of, the promoter, under conditions such that the chemical if capable of acting as a transcriptional modulator of the gene encoding the protein of interest, causes a measurable detectable signal to be produced by the polypeptide expressed by the reporter gene;

(b) quantitatively determining the amount of the signal so produced; and (c) comparing the amount so determined with the amount of produced signal detected in the absence of any chemical being tested or upon contacting the sample with other chemicals so as to thereby identify the chemical as a chemical which causes a change in the detectable signal produced by the polypeptide, and determining whether the chemical specifically transcriptionally modulates expression of the gene associated with the treatment of one or more symptoms of the cardiovascular disease.

2. A method of determining whether a chemical not previously known to be a modulator of protein biosynthesis is capable of specifically transcriptionally modulating the expression of a gene encoding a protein of interest associated with the treatment of one or more symptoms of a cardiovascular disease which comprises:

(a) contacting a sample which contains a predefined number of identical eucaryotic cells with a predetermined concentration of the chemical to be tested, each such cell comprising a DNA construct consisting essentially of in 5' to 3' order (i) a modulatable transcriptional regulatory sequence of the gene encoding the protein of interest, (ii) a promoter of the gene encoding the protein of interest, and (iii) a DNA sequence transcribable into mRNA coupled to, and under the control of, the promoter, under conditions such that the chemical if capable of acting as a transcriptional modulator of the gene encoding the protein of interest, causes a measurable difference in the amount of mRNA transcribed from the DNA sequence;

(b) quantitatively determining the amount of the mRNA so produced; and (c) comparing the amount so determined with the amount of mRNA detected in the absence of any chemical being tested or upon contacting the sample with other chemicals so as to thereby identify the chemical as a chemical which causes a change in the detectable mRNA amount, and determining whether the chemical specifically transcriptionally modulates expression of the gene of interest associated with the treatment of one or more symptoms of the cardiovascular disease.

3. A screening method according to any one of claims 1 or 2, which comprises separately contacting each of a plurality of identical samples, each sample containing a predefined number of identical cells under conditions wherein said contacting is effected with a predetermined concentration of each different chemical to be tested.

4. A screening method of claim 3, wherein the plurality of samples comprises more than about $10^4$ samples.

5. A screening method of claim 4, wherein the plurality of samples comprises more than about $5 \times 10^4$ samples.

6. A screening method of claim 3, where more than about $10^3$ samples per week are contacted with different chemicals.

7. A method of claim 2, wherein the amount of mRNA is determined by quantitative polymerase chain reaction.

* * * * *

SEQUENCE LISTING ( 1 ) GENERAL INFORMATION:

( i i i ) NUMBER OF SEQUENCES: 93

( 2 ) INFORMATION FOR SEQ ID NO:1:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TCGACCCGGG  CGGCCGCTGA  TCAGACGTCG  GGCCCGGTAC  CGTGCACTAC  GTAAGATCTA        60

AGCTT                                                                        65
```

( 2 ) INFORMATION FOR SEQ ID NO:2:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
ACTAGTCTGC  AGGCTAGCAC  TCTTCTGGTC  CCCACAGACT  CAGAGAGAAC  CCACCATGGA        60
```

( 2 ) INFORMATION FOR SEQ ID NO:3:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
AGACGCCAAA  AACATCAAGA  AAGGCCCGGC  GCCATTCTAT  CCTCTAGAGG  GGATCCAGCT        60

G                                                                            61
```

( 2 ) INFORMATION FOR SEQ ID NO:4:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
TAGATCTTAC  GTAGTGCACG  GTACCGGGCC  CGACGTCTGA  TCAGCGGCCG  CCCGGG          56
```

( 2 ) INFORMATION FOR SEQ ID NO:5:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GGTGGGTTCT CTCTGAGTCT GTGGGGACCA GAAGAGTGCT AGCCTGCGAC TAGTAAGCT    59

( 2 ) INFORMATION FOR SEQ ID NO:6:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AATTCAGCTG GATCCCCTCT AGAGGATAGA ATGGCGCCGG GCCTTTCTTG ATGTTTTTGG    60

CGTCTTCCAT    70

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GATCGGCCCC TAGGGCCGCG GCCGCAT    27

( 2 ) INFORMATION FOR SEQ ID NO:8:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

ATGCGGCCGC GGCCCTAGGG GCC    23

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GATCGGCCCT AGGGGCGGCC GCAT    24

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

ATGCGGCCGC GGCCCCCTAG GGCC                                                      24

(2) INFORMATION FOR SEQ ID NO:11:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCTTGGCCC CTAGGGCCAC TAGTCTGCAG CTATGATGAC ACAAACCCCG CCCAGCGTCT              60

TGTCATTGGC GA                                                                   72

(2) INFORMATION FOR SEQ ID NO:12:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TCGAATTCGC CAATGACAAG ACGCTGGGCG GGGTTTGTGT CATCATAGCT CAGACTAGTG              60

GCCCTAGGGG CCA                                                                  73

(2) INFORMATION FOR SEQ ID NO:13:

(i) SEQUENCE CHARACTERISTICS:
        (A) LENGTH: 73 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

ATTCGAACAC GCAGATGCAG TCGGGGCGGC GCGGTCCGAG GTCCACTTCG CATATTAAGG              60

TGACGCGTGT GGG                                                                  73

(2) INFORMATION FOR SEQ ID NO:14:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CTAGCCCACA CGCGTCACCT TAATATGCGA AGTGGACCTC GGACCGCGCC GCCCGACTG              60

CATCTGCGTG T                                                                    71

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (  i i  ) MOLECULE TYPE: DNA (genomic)

( x i ) SEQUENCE DESCRIPTION: SEQ ID NO:15:

GATCGGCCCC TAGGGCCATT T  21

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

AAATGGCCCT AGGGGCC  17

( 2 ) INFORMATION FOR SEQ ID NO:17:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

TATTTCTGAA ATCAGCAGCA CCTGAGCAAA  30

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

TGGAACATAA GGAAGTGGTT CTTCTACTTC  30

( 2 ) INFORMATION FOR SEQ ID NO:19:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:19:

CATGTGGTCC AGGATTGCTA CCATGGTGAT GG  32

( 2 ) INFORMATION FOR SEQ ID NO:20:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:20:

GGCCAGTCCC AA  12

( 2 ) INFORMATION FOR SEQ ID NO:21:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

CATTTGGGAC T        11

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GCTGCGGTGC TGACCTTGGC CGTGCTCTTC CTGACGGGTA    40

( 2 ) INFORMATION FOR SEQ ID NO:23:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

GGTGTCCCCT AACCTAGGGA GCCAACCATC GGG    33

( 2 ) INFORMATION FOR SEQ ID NO:24:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GGGCCTTCTC CCTAAATCCC CGTGGCCACC TCCTG    35

( 2 ) INFORMATION FOR SEQ ID NO:25:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

CTGAGGTCTT CTCCGCTCT GTGCCCTTCT CCTCACCTGG CTGCAACTGA GTTCGGGGAG    60

CACGGGGCTT C    71

( 2 ) INFORMATION FOR SEQ ID NO:26:

( i ) SEQUENCE CHARACTERISTICS:
    ( A ) LENGTH: 79 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:26:

```
TGCAGAAGCC  CCGTGCTCCC  CGAACACAGT  TGCAGCCAGG  AGAGGAGAAG  GGCACAGAGC        60
GGGAGAAGAC  CTCAGGTAC                                                        79
```

( 2 ) INFORMATION FOR SEQ ID NO:27:

( i ) SEQUENCE CHARACTERISTICS:
        ( A ) LENGTH: 82 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
TGCATGCTGA  AGGCACCCAC  TCAGCCAGGC  CCTTCTTCTC  CTCCAGGTCC  CCCACGGCCC        60
TTCAATGGTC  CCGGCCGGCA  TG                                                   82
```

( 2 ) INFORMATION FOR SEQ ID NO:28:

( i ) SEQUENCE CHARACTERISTICS:
        ( A ) LENGTH: 74 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
CCGGCCGGGA  CCATTGAAGG  GCCGTGGGGG  ACCTGGAGGA  GAAGAAGGGC  CTGCCTGAGT        60
GGGTGCCTTC  AGCA                                                             74
```

( 2 ) INFORMATION FOR SEQ ID NO:29:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

```
GGCCGCAGCC  CAGGAGCCGC  CCCACCGCAG                                           30
```

( 2 ) INFORMATION FOR SEQ ID NO:30:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
TGAGTGCCCT  TCTCGGTTGC  TGCCGCTGAG  GAG                                      33
```

( 2 ) INFORMATION FOR SEQ ID NO:31:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

CTGGCGATGG ACCCGCCGAG GCCCGCGCTG CTGGCG    36

( 2 ) INFORMATION FOR SEQ ID NO:32:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

CTGGCGATGG AAGACGCCAA AAACATCAAG AAAGGCCCGG CGCCATTCTA TCCT    54

( 2 ) INFORMATION FOR SEQ ID NO:33:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

CTAGAGGATA GAATGGCGCC GGGCCTTTCT TGATGTTTTT GGCGTCTTCC ATCGCCAG    58

( 2 ) INFORMATION FOR SEQ ID NO:34:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GGGCCCTGGG GCTGGAAATT GCGCTGGACC GTCGCCTTGC TC    42

( 2 ) INFORMATION FOR SEQ ID NO:35:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GGGCGACAGA TGTGAAAGAA ACGAGTTCCA GTGCCAAGAC GGG    43

( 2 ) INFORMATION FOR SEQ ID NO:36:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:36:

CGAGTGCAAT CGCGGGAAGC CAGGGTTTCC 30

( 2 ) INFORMATION FOR SEQ ID NO:37:

( i ) SEQUENCE CHARACTERISTICS:
 ( A ) LENGTH: 74 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:37:

CTAGGACACA GCAGGTCGTG ATCCGGGTCG GGACACTGCC TGGCAGAGGC TGCGACATGG 60

TCCCGGCCGG CATG 74

( 2 ) INFORMATION FOR SEQ ID NO:38:

( i ) SEQUENCE CHARACTERISTICS:
 ( A ) LENGTH: 70 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:38:

CCGGCCGGG ACCATGTCGCA GCCTCTGCCA GGCAGTGTCC CGACCCGGAT CACGACCTGC 60

TGTGTCCTAG 70

( 2 ) INFORMATION FOR SEQ ID NO:39:

( i ) SEQUENCE CHARACTERISTICS:
 ( A ) LENGTH: 42 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:39:

ATGATGACCA CATCTTTGAT TTGGGGGATT GCTATAGCAG CA 42

( 2 ) INFORMATION FOR SEQ ID NO:40:

( i ) SEQUENCE CHARACTERISTICS:
 ( A ) LENGTH: 35 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO: 40:

GATTTTCTTC CTCAGAGATT TTGGCCTAGA TTTGC 35

( 2 ) INFORMATION FOR SEQ ID NO:41:

( i ) SEQUENCE CHARACTERISTICS:
 ( A ) LENGTH: 45 base pairs
 ( B ) TYPE: nucleic acid
 ( C ) STRANDEDNESS: single (D) TOPOLOGY: linear (i i) MOLECULE TYPE: DNA (genomic)

(x i) SEQUENCE DESCRIPTION: SEQ ID NO:41:

GCTGTTGTCT ATGGCTTATT CTTGGAATTA GGAGAAGGCA AACGG                45

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:42:

CCTAGATTTG CAATGGTCCC GGCCGGCATG                                 30

(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:43:

CCGGCCGGGA CCATTGCAAA TCTAGG                                     26

(2) INFORMATION FOR SEQ ID NO:44:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:44:

ATGAACTTTC TGCTGTCTTG GGTGCATTGG AGC                             33

(2) INFORMATION FOR SEQ ID NO:45:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:45:

TTGCCTTGCT GCTCTACCTC CACCATGCCA AG                              32

(2) INFORMATION FOR SEQ ID NO:46:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:46:

TCGCGGAGGC TTGGGGCAGC CGGGTAGCTC GGAGGT                                        36

( 2 ) INFORMATION FOR SEQ ID NO:47:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

CGCCGAGGAG AGCGGGCCGC CCCACAGCCC GAGCCGGAGA GGGA                                44

( 2 ) INFORMATION FOR SEQ ID NO:48:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

CCGGCTCGGG CTGTGGGGCG GCCCGCTCTC CTCGG                                         35

( 2 ) INFORMATION FOR SEQ ID NO:49:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

GCGCGAGCCG CGCCGGCCCC GGTCGGGCCT CCGAAACCAT GGTCCCGGCC GGCATG                   56

( 2 ) INFORMATION FOR SEQ ID NO:50:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

CCGGCCGGGA CCATGGTTTC GGAGGCCCGA CCGGGGCCGG CGCGGCTCGC GCTCCCTCT               59

( 2 ) INFORMATION FOR SEQ ID NO:51:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

CCGGCGCGGT CATACGGGCA GCTGG                                                    25

( 2 ) INFORMATION FOR SEQ ID NO:52:

( i ) SEQUENCE CHARACTERISTICS:
    ( A ) LENGTH: 13 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:52:

CTGCCCGTAT GGA 13

( 2 ) INFORMATION FOR SEQ ID NO:53:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

AGAAACATCC AATTCTCAAA CTGAAGCTCG CACTCTCGCC TCCA 44

( 2 ) INFORMATION FOR SEQ ID NO:54:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

ATGAAAGTCT CTGCCGCCCT TCTGTGCCTG CTGCTCAT 38

( 2 ) INFORMATION FOR SEQ ID NO:55:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

GCAGCCACCT TCATTCCCCA AGGGCTCGCT CAGCCAG 37

( 2 ) INFORMATION FOR SEQ ID NO:56:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

GTCCCGGCCG GC 12

( 2 ) INFORMATION FOR SEQ ID NO:57:

( i ) SEQUENCE CHARACTERISTICS:
        ( A ) LENGTH: 19 base pairs
        ( B ) TYPE: nucleic acid
        ( C ) STRANDEDNESS: single (D) TOPOLOGY: linear (ii) MOLECULE TYPE: DNA (genomic)

(xi) SEQUENCE DESCRIPTION: SEQ ID NO:57:

TGAGCCGGCC GGGACTGCA 19

(2) INFORMATION FOR SEQ ID NO:58:

(i) SEQUENCE CHARACTERISTICS:
(A) LENGTH: 44 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:58:

ATGAAAAGGA TGGTTTCTTG GAGCTTCCAC AAACTTAAAA CCAT 44

(2) INFORMATION FOR SEQ ID NO:59:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:59:

CTATTATTGC TACTATTGTG TGTTTTCTA GTTAAGTCCC AAGGTGT 47

(2) INFORMATION FOR SEQ ID NO:60:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:60:

GAGTCACGAT TTAGTGGTT GCCTTGTGAG TAGGTCAAAT T 41

(2) INFORMATION FOR SEQ ID NO:61:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:61:

CTACATGAAA AGGATGGATT CTTGGAGCTT CCACAAACTT AAAACCATGG AAGACGCCAA 60

AAACATCAAG AAAGGCCCGG 80

(2) INFORMATION FOR SEQ ID NO:62:

(i) SEQUENCE CHARACTERISTICS:
(A) LENGTH: 80 base pairs
(B) TYPE: nucleic acid
(C) STRANDEDNESS: single
(D) TOPOLOGY: linear (ii) MOLECULE TYPE: DNA (genomic)

(x i) SEQUENCE DESCRIPTION: SEQ ID NO:62:

CGCCGGGCCT TTCTTGATGT TTTTGGCGTC TTCCATGGTT TTAAGTTTGT GGAAGCTCCA 60

AGAATCCATC CTTTTCATGT 80

(2) INFORMATION FOR SEQ ID NO:63:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:63:

CCGAATTCAT AAATCAGTGC TGCTTTC 27

(2) INFORMATION FOR SEQ ID NO:64:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:64:

CCGAATTCAA GAAGTATGGA GCAGTGG 27

(2) INFORMATION FOR SEQ ID NO:65:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:65:

CCGGATCCAA ACACGAGGAG GTAAAG 26

(2) INFORMATION FOR SEQ ID NO:66:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:66:

CCGGATCCTT ATATCATTTG CATTAGTTG 29

(2) INFORMATION FOR SEQ ID NO:67:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:67:

CCGGATCCAT TTCCTTTTCC CGTGAG 26

( 2 ) INFORMATION FOR SEQ ID NO:68:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

GTATGGAGCA GTGGGATCAC TTTCACAATC AACAGGAGGA 40

( 2 ) INFORMATION FOR SEQ ID NO:69:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

AGGACACTGA TAGCTGCTCC GAATCTGTGA AATTTGATGC 40

( 2 ) INFORMATION FOR SEQ ID NO:70:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:70:

GCTTTTTGTT CCAACCCCCC TGCATT 26

( 2 ) INFORMATION FOR SEQ ID NO:71:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:71:

CCCTGCATTG TCTTGGACAC CAAAT 25

( 2 ) INFORMATION FOR SEQ ID NO:72:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

GCGCTCCAGG AGAAGCTGGT GAGT 24

( 2 ) INFORMATION FOR SEQ ID NO:73:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:73:

AAGCTGATGG GTGAGTGTCT TGGC 24

( 2 ) INFORMATION FOR SEQ ID NO:74:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:74:

ATCAGCGGCT CAGCCTTCTT 20

( 2 ) INFORMATION FOR SEQ ID NO:75:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:75:

GGTGACCACA AAATGCCAGG GAGGCGGG 28

( 2 ) INFORMATION FOR SEQ ID NO:76:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:76:

GCAGGCCACA GTGCCCAAGA GACAGCAGCA GGCT 34

( 2 ) INFORMATION FOR SEQ ID NO:77:

( i ) SEQUENCE CHARACTERISTICS:
    ( A ) LENGTH: 44 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:77:

CAGAACCTCA GTGGATCTCA GAGAGAGCCC CAGACTGAGG GAAG 44

( 2 ) INFORMATION FOR SEQ ID NO:78:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear (i i) MOLECULE TYPE: DNA (genomic)

(x i) SEQUENCE DESCRIPTION: SEQ ID NO:78:

ATGGATGGAG AAGGATGCCT CGCTGGGGAC TGCTGCTGCT 40

(2) INFORMATION FOR SEQ ID NO:79:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:79:

CTGCTCTGGG GCTCCTGTAC CTTTGGTCTC CCGACAGACA 40

(2) INFORMATION FOR SEQ ID NO:80:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:80:

TGGAGTGTAT AAAAGGGGAA GGGCTAAGGG AGCCA 35

(2) INFORMATION FOR SEQ ID NO:81:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:81:

TCTGTGGCTC CCTTAGCCCT TCCCCTTTTA TACACTCCAT GCA 43

(2) INFORMATION FOR SEQ ID NO:82:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:82:

CAGAACCTCA GTGGATCTCA GAGAGAGCCC CAGACTGAGG GAAG 44

(2) INFORMATION FOR SEQ ID NO:83:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:83:

CATGCTTCCC TCAGTCTGGG GCTCTCTCTG AGATCCACTG AGGT 44

( 2 ) INFORMATION FOR SEQ ID NO:84:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:84:

GGAGATGGTG GAGACGCTGA AAAGCTTCTT 30

( 2 ) INFORMATION FOR SEQ ID NO:85:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:85:

GACACCTCTC TGCAAGGGAA GAATGAGATA AAC 33

( 2 ) INFORMATION FOR SEQ ID NO:86:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:86:

AGGCTCAGGA ACCTGGGTTT AAAAGACTCC 30

( 2 ) INFORMATION FOR SEQ ID NO:87:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:87:

TCTTGCAATG GTGTGGAGAG AGGCAGCGAC 30

( 2 ) INFORMATION FOR SEQ ID NO:88:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:88:

TGGCGCAGCG CTCCAGGAGA AGCTG 25

( 2 ) INFORMATION FOR SEQ ID NO:89:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:89:

CGCTATGGAG TTGGCTCAAG CAGCCTGC        28

(2) INFORMATION FOR SEQ ID NO:90:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:90:

GAGTAGAGAC ACTGCTGCTG AGATG        25

(2) INFORMATION FOR SEQ ID NO:91:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:91:

GGCGGGTCTG TAGGCAGGTC GGCTC        25

(2) INFORMATION FOR SEQ ID NO:92:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:92:

CTCCAGCCCG CAGCTCCAGG AGTCTG        26

(2) INFORMATION FOR SEQ ID NO:93:

(i) SEQUENCE CHARACTERISTICS:
    (A) LENGTH: 25 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:93:

CCCTCTACAC TGGCAGTTCC ACCTG        25